United States Patent
Ke et al.

(10) Patent No.: US 9,937,272 B2
(45) Date of Patent: Apr. 10, 2018

(54) ANTHRACENYL-TETRALACTAM MACROCYCLES AND THEIR USE IN DETECTING A TARGET SACCHARIDE

(71) Applicant: University of Bristol, Bristol (GB)

(72) Inventors: Chenfeng Ke, Bristol (GB); Anthony P. Davis, Bristol (GB)

(73) Assignee: University of Bristol, Bristol (GB)

( * ) Notice: Subject to any disclaimer, the term of this patent is extended or adjusted under 35 U.S.C. 154(b) by 0 days.

(21) Appl. No.: 15/445,710

(22) Filed: Feb. 28, 2017

(65) Prior Publication Data

US 2017/0266321 A1 Sep. 21, 2017

Related U.S. Application Data

(63) Continuation of application No. 14/397,254, filed as application No. PCT/GB2013/051079 on Apr. 26, 2013, now Pat. No. 9,610,365.

(30) Foreign Application Priority Data

Apr. 27, 2012 (GB) .................................. 1207392.0

(51) Int. Cl.
| | | |
|---|---|---|
| A61K 49/00 | (2006.01) | |
| C07D 257/10 | (2006.01) | |
| G01N 33/66 | (2006.01) | |
| G01N 33/52 | (2006.01) | |
| A61B 5/145 | (2006.01) | |
| A61B 5/1455 | (2006.01) | |

(52) U.S. Cl.
CPC ........ A61K 49/0004 (2013.01); A61B 5/1455 (2013.01); A61B 5/14532 (2013.01); C07D 257/10 (2013.01); G01N 33/52 (2013.01); G01N 33/66 (2013.01); *G01N 2800/042* (2013.01)

(58) Field of Classification Search
CPC ..... A61K 49/00; C07D 245/00; C07D 513/00
See application file for complete search history.

(56) References Cited

U.S. PATENT DOCUMENTS

| | | | |
|---|---|---|---|
| 7,179,616 B1 | 2/2007 | Smith | |
| 2004/0142475 A1* | 7/2004 | Barman ............... | A61K 9/1617 435/459 |
| 2010/0266507 A1* | 10/2010 | Terpetschnig ..... | A61K 49/0032 424/9.6 |

FOREIGN PATENT DOCUMENTS

| | | |
|---|---|---|
| JP | 2003-73399 | 3/2003 |
| WO | WO-2011059457 A1 | 5/2011 |
| WO | WO-2011087521 A1 | 7/2011 |
| WO | WO-2013160701 A1 | 10/2013 |

OTHER PUBLICATIONS

Jeremiah Gassensmith et al., Self-Assembly of Fluorescent Inclusion Complexes in Compettitive Media Including the Interior of Living cells, JACS, 2007, 129, 15054-15059.*
Barwell et al., "A Synthetic Lectin for β-Glucosyl", Angew. Chem. Int. Ed., 2009, pp. 7673-7676, vol. 48, No. 41.
Baumes et al., "Storable, thermally activated, near-infrared chemiluminescent dyes and dye-stained microparticles for optical imaging", Nature Chemistry, 2010, pp. 1025-1030, vol. 2.
Baumes et al., "Using the Rotaxane Mechanical Bond to Enhance Chemical Reactivity", Organic Letters, 2010, pp. 4980-4983, vol. 12, No. 21.

(Continued)

*Primary Examiner* — Michael G Hartley
*Assistant Examiner* — Jagadishwar R Samala
(74) *Attorney, Agent, or Firm* — McCarter & English, LLP; Elizabeth A. Hanley

(57) ABSTRACT

A water-soluble compound of the formula (I):

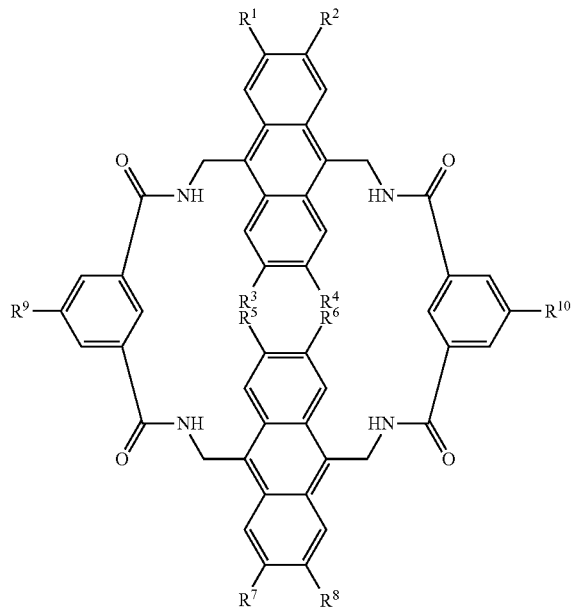

wherein $R^9$ and $R^{10}$ are suitably hydrophilic substituents, which may be used to selectively bind to a target saccharide such as glucose and which exhibits a detectable spectroscopic response to such binding, thus enabling its use in the detection and correction of blood glucose concentrations in vivo.

13 Claims, 30 Drawing Sheets

(56) References Cited

OTHER PUBLICATIONS

Collins et al., "Thermally-activated chemiluminescent squaraine rotaxane endoperoxide with green emission", Chem. Commun., 2011, pp. 12352-12354, vol. 47.
Ferrand et al., "A Synthetic Lectin for 0-Linked β-N-Acetylglucosamine", Angew. Chem. Int. Ed., 2009, pp. 1775-1779, vol. 48.
Gassensmith et al., "Self-Assembly of Fluorescent Inclusion Complexes in Competitive Media Including the Interior pf Living Cells", Journal of the American Chemical Society, 2007, pp. 15054-15059, vol. 129, No. 48.
Gassensmith et al., "Synthesis and Photophysical Investigation of Squaraine Rotaxanes by "Clicked Capping"", Organic Letters, 2008, pp. 3343-3346, vol. 10, No. 15.
Gassensmith et al., "Discovery and early development of squaraine rotaxanes", Chem. Commun., 2009, pp. 6329-6338.
Gassensmith et al., "Cycloaddition to an anthracene-derived macrocyclic receptor with supramolecular control of regioselectivity", Chem. Commun., 2009, pp. 2517-2519, vol. 18.
Gunnlaugsson et al., "Fluorescent Sensing of Pyrophosphate and Bis-carboxylates with Charge Neutral PET Chemosensors", Organic Letters, 2002, pp. 2449-2452, vol. 4, No. 15.
International Search Report and Written Opinion from related International Application No. PCT/GB2013/051079, dated Jul. 2, 2013; 12 pgs.
International Preliminary Report on Patentability from related International Application No. PCT/GB2013/051079, dated Oct. 28, 2014; 7 pages.

Katsuta et al., "Synthesis, Properties, and Ambipolar Organic Field-Effect Transistor Performances of Symmetrically Cyanated Pentacene and Naphthacene as Air-Stable Acene Derivatives", Organic Letters, 2011, pp. 1454-1457, vol. 13, No. 6.
Ke et al., "A simple and accessible synthetic lectin for glucose recognition and sensing", Nature Chemistry, 2012, pp. 718-723, vol. 4.
Klein et al., "Carbohydrate Recognition in Water by a Tricyclic Polyamide Receptor", Angew. Chem. Int. Ed., 2005, pp. 298-302, vol. 44.
Lee et al., "Singlet Oxygen Release and Cell Toxicity of a Chemiluminescent Squaraine Rotaxane Dye: Implications for Molecular Imaging", Aust. J. Chem., 2011, pp. 604-610, vol. 64.
Lee et al., "Squaraine [2]catenanes: synthesis, structure and molecular dynamics", Chem. Commun., 2011, pp. 7188-7190, vol. 47, No. 25.
M0djewski et al., "Isolation and X-ray structural characterization of a dicationic homotrimer of 2,3,6,7-tetramethoxy-9,10-dimethylanthracene cation radical", Tetrahedron Letters, 2009, pp. 6687-6690, vol. 50.
Murgu et al., "Macrocycle Breathing in [2]Rotaxanes with Tetralactam Macrocycles", The Journal of Organic Chemistry, 2011, pp. 688-691, vol. 76, No. 2.
Shapiro et al., "Measuring Binding of Protein to Gel-Bound Ligands Using Magnetic Levitation", Journal of the American Chemical Society, 2012, pp. 5637-5646, vol. 134.
Yamada et al., "Photochemical Synthesis of Pentacene and its Derivatives", Chem. Eur. J., 2005, pp. 6212-6220, vol. 11.

* cited by examiner

FIG. 2A
FIG. 2B
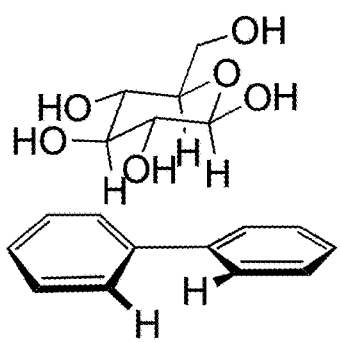
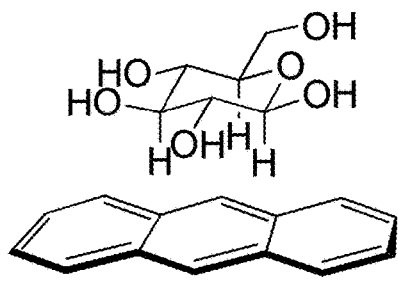
FIG. 2C
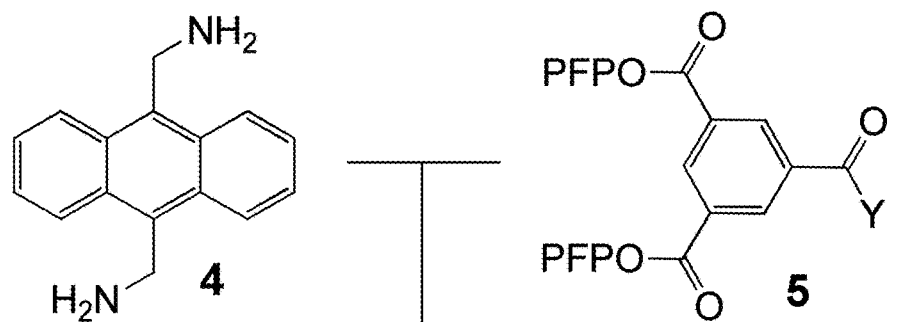
i, high dilution
ii, CF$_3$CO$_2$H, then NaOH
Y = NHC(CH$_2$OCH$_2$CH$_2$CO$_2$Bu$^t$)$_3$
PFP = pentafluorophenyl
3

G2-NH₂

G2-Linker

AnR-G2-tBu

AnR-G2-Na

G3-NO₂

G3-NH₂

G3-Linker

AnR-G3-tBu

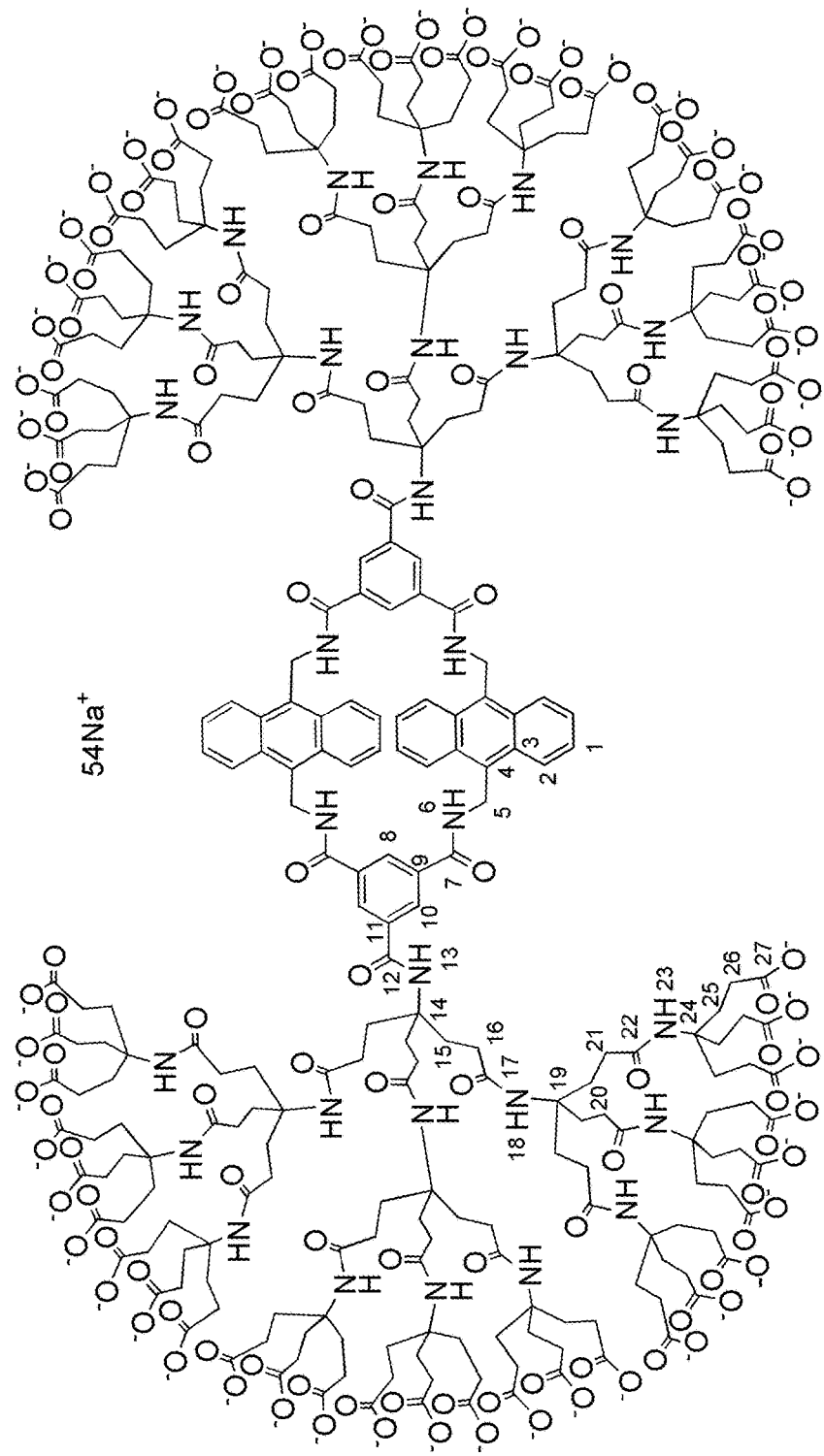
FIG. 14I AnR-G3-Na c) Selectivity

| Sugar | NMR $K_a$ (M$^{-1}$) | Fluorescence $K_a$ (M$^{-1}$) |
|---|---|---|
| D-Glucose | 89 | 87 |
| Methyl-β-Glucoside | 115 | 105 |
| D-Mannose | 1 | n/a |

ANTHRACENYL-TETRALACTAM MACROCYCLES AND THEIR USE IN DETECTING A TARGET SACCHARIDE

RELATED APPLICATIONS

This application is a continuation of and claims priority under 35 U.S.C. § 120 to U.S. application Ser. No. 14/397,254 filed on Oct. 27, 2014, which is § 371 of International Application No. PCT/GB2013/051079 filed on Apr. 26, 2013, which claims priority to U.K. Application Serial No. GB 1207392.0 filed on Apr. 27, 2012, the entire disclosures of each of which are incorporated herein by reference in their entirety.

FIELD OF THE INVENTION

This invention relates to novel compounds, which can be of use in detecting saccharides, in particular glucose, in an aqueous environment such as blood. The invention also relates to methods for preparing and using such compounds, and to products which contain them.

BACKGROUND TO THE INVENTION

For a number of medical reasons, it can be desirable to monitor the level of sugars, in particular glucose, in the bloodstream. This is particularly important in the diagnosis and treatment of diabetics, and also for patients in intensive care, where it has been found that changes in blood glucose levels can provide vital information about potential health complications.

Diabetes is a growing medical problem, currently thought to affect about 5% of the global population. Although control is possible through lifestyle management and/or insulin injections, serious issues remain. A low blood glucose concentration, caused by excess insulin, can be fatal, whilst high glucose levels can lead to long term complications such as heart disease, blindness, kidney damage, stroke and nerve damage.

Close control of blood glucose levels is therefore desirable for both diabetics and intensive care patients. Ideally, such control would involve the accurate and continuous (or at least timely) measurement of blood glucose concentrations. However, whilst periodic analyses of withdrawn blood samples are routine, continuous monitoring remains an unsolved problem. Some systems have reached the marketplace, but their reliance on enzyme-based detection technology imposes limitations: in particular, they only measure glucose concentrations in interstitial fluid, just beneath the skin, and these lag behind the more important blood glucose concentrations.

Were such problems to be solved in a practical manner, this could assist in the design of an "artificial pancreas", which could continuously supply insulin to a patient's bloodstream in response to changes in blood glucose levels, in order to maintain those levels within a desired, safe range. Such systems could prove life-changing for diabetics and their carers. The ability to monitor blood glucose levels continuously, in vivo, could also significantly improve the care of patients in intensive care, and potentially of other at-risk individuals.

Historically, the detection of saccharides in an aqueous environment such as blood has presented challenges. Saccharides are hydrophilic species, bearing hydromimetic hydroxyl groups, which makes them difficult to extract from water. For a chemical detection system, distinguishing between target molecule and solvent is a significant problem. Achieving selectivity for a specific target molecule is also non-trivial: the generic carbohydrate structure allows great scope for variation, but differences between individual saccharides are often subtle (for example, the configuration of a single asymmetric centre).

As referred to above, it is known to assay blood for glucose levels using enzymes, for example glucose oxidase, which bind selectively to glucose molecules and thereby generate a detectable electrochemical signal. Such techniques usually have to be carried out on isolated fresh blood samples withdrawn from a patient's body, rather than in vivo, and they also result in destruction of the glucose they detect; they do not therefore lend themselves to continuous blood glucose monitoring. Typically a power source is required for detection of the enzyme-glucose interaction, and moreover enzymes tend to have poor stability. Receptor-based approaches are therefore likely to prove more suitable for glucose monitoring, but none have yet been approved for general use.

Thus far, most work on receptor-based glucose sensing has employed boronic acids, which bind to carbohydrates through covalent B—O bonds. These receptors may also incorporate chromophore labelling moieties, to allow their detection for instance by fluorescence spectroscopy. It is already known to introduce such labelled boronic acid-based receptors into the bloodstream in the form of a coating on a probe such as a fibre optic cable, for use in the continuous monitoring of blood glucose levels. However, boronic acid-based receptors tend to have a relatively low selectivity for glucose: they can also bind to other carbohydrates, and to diols and lactates, which may be present in the bloodstream. They can also be sensitive to oxygen, which again can compromise their efficacy as glucose receptors in the bloodstream.

Lectins are naturally-occurring proteins which are capable of binding to saccharides, and as such they too have been used to assess blood glucose levels in particular in medical diagnostic techniques. Examples of lectins used in this way include Concanavalin A, *Lens culinaris* agglutinin and *Pisum aativum* agglutinin. Even these, however, tend to show low affinities for the target saccharides, and often quite modest selectivities. Research has therefore turned to the creation of synthetic analogues. Synthetic lectins are organic molecules which are capable of biomimetic saccharide recognition, ie binding to saccharides in aqueous systems using the non-covalent interactions employed by natural lectins.

Perhaps unsurprisingly, due to the hydrophilicity and stereochemical complexity of carbohydrates, the design of synthetic lectins has proved to be less than straightforward. Although progress has been made, binding affinities have been mostly low and good selectivities rare. Moreover, success usually comes at the cost of structural complexity.

The octalactam 2 shown in FIG. 1A, reported previously by Barwell et al [*Angew Chem, Int Ed,* 48; 7673-7676 (2009)], is an example of a synthetic lectin analogue proposed for use in the detection of carbohydrates. This tricyclic system is able to surround a β-D-glucose molecule 1, providing polar and apolar surfaces which complement the all-equatorial substitution pattern of the carbohydrate. Complex formation is thought to be driven by hydrophobic CH-π interactions between saccharide CH and biphenyl surfaces, and by polar interactions between saccharide OH groups and isophthalamide groups in compound 2. The propoxy groups (—OPr) appear to be required for optimal glucose selectivity.

The compound 2 shows excellent selectivity for glucose; for example, ratios of binding constants are 20:1 for glucose vs galactose, and 60:1 for glucose vs mannose. The affinity of the lactam for glucose is 60 $M^{-1}$, which may seem low, but is actually state-of-the-art for a synthetic system operating in water through non-covalent interactions: the well-studied lectin Concanavalin A is just one order of magnitude stronger. Furthermore, the affinity is not too low to be useful, in particular in the detection of glucose in blood: as blood glucose levels are relatively high (~2-13 mM), binding affinities need to be moderate to avoid receptor saturation.

Synthetic lectins such as 2 are therefore promising, but their elaborate structures can impose a barrier to further development. The oligoamide 2 is designed to enclose its carbohydrate target, providing complementary surfaces as shown in FIG. 1A. Though apparently the key to success, this results in a complex cage architecture, requiring a 20-step synthesis with an overall yield of just ~0.1%. Preparing substantial quantities can be difficult, and further modification (for example to link the receptor to a substrate surface) represents a major undertaking.

The synthetic lectin 2 possesses a further potential disadvantage for practical glucose sensing. Receptor-based sensing requires a signalling system, to allow measurement of the level of occupancy by the target molecule. Receptor 2 presents no clear opportunities in this respect.

We have now been able to create a novel class of glucose receptor compounds, which can overcome or at least mitigate the above described problems. Embodiments of the invention can allow the efficient and selective detection of blood glucose levels, in vivo, using optical signals. They can thus be of use in continuous blood glucose monitoring. Moreover, these new compounds can be significantly less complex than the previously reported synthetic lectins, making them more simple and inexpensive not only to prepare, but also to tailor for use in a specific environment or physical form, or for a specific purpose.

STATEMENTS OF THE INVENTION

According to a first aspect of the present invention there is provided a water-soluble compound of the formula (I):

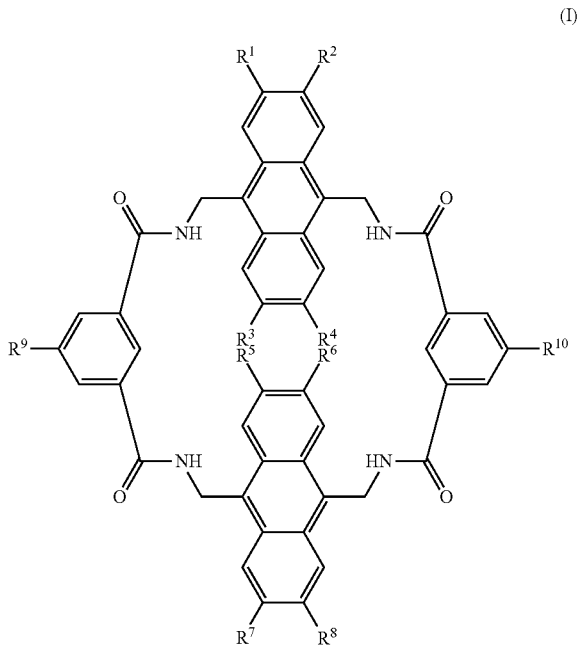

(I)

wherein $R^1$ to $R^8$ are each independently selected from hydrogen; optionally substituted alkyl groups; optionally substituted cycloalkyl groups; optionally substituted heterocyclyl groups; optionally substituted alkenyl groups; optionally substituted alkynyl groups; optionally substituted aryl groups; optionally substituted heteroaryl groups; alkoxyl groups; ketone and aldehyde groups; carboxylic acids and carboxylate ions; carboxylate esters; —$SO_3H$; —$SO_3^-$; —$OSO_3H$; —$OSO_3^-$; —$PO_3XY$ where X and Y are independently hydrogen, alkyl or a negative charge; —$OPO_3XY$ where X and Y are independently hydrogen, alkyl or a negative charge; amines; amides; halo groups; —CN; —$NO_2$; —OH; and imino and imido groups, provided that in any one or more of the pairs $R^1R^2$, $R^3R^4$, $R^5R^6$ and $R^7R^8$, the two substituents may be joined together to form part of an optionally substituted cyclic group; and $R^9$ and $R^{10}$ are each independently selected from hydrogen; optionally substituted alkyl groups; optionally substituted cycloalkyl groups; optionally substituted heterocyclyl groups; optionally substituted alkenyl groups; optionally substituted alkynyl groups; optionally substituted aryl groups; optionally substituted heteroaryl groups; alkoxyl groups; ketone and aldehyde groups; carboxylic acids and carboxylate ions; carboxylate esters; —$SO_3H$; —$SO_3^-$; —$OSO_3H$; —$OSO_3^-$; —$PO_3XY$ where X and Y are independently hydrogen, alkyl or a negative charge; —$OPO_3XY$ where X and Y are independently hydrogen, alkyl or a negative charge; amines; amides; halo groups; —CN; —$NO_2$; —OH; and imino and imido groups.

It has been found that these relatively simple, usually monocyclic, molecules can be capable of associating with saccharide molecules, in particular all-equatorial saccharides such as glucose. They can be synthesised in a relatively straightforward manner, often (as described below) in just a few steps from commercially available starting materials, and with relatively high yields. They can thus be relatively inexpensive to produce, and have also been found to have good stability.

Compounds of formula (I) can also, despite their improved simplicity and accessibility relative to the known synthetic lectin 2, show surprisingly good selectivity for specific carbohydrate molecules, in particular glucose (which in this document is used to mean D-glucose). The two condensed aromatic moieties, based on anthracene, have been found to provide the hydrophobic planar surfaces which appear to be necessary for selective binding to glucose. The binding between a compound (I) and glucose appears not to involve covalent bonds, as in the prior art boronic acid-based receptors, but instead a rapid equilibrium which allows glucose molecules to enter and leave the cavity defined by the cyclic structure of the molecule. This means that the binding, when used to detect blood glucose levels, would not significantly reduce the availability of the glucose in the blood.

Also importantly, the presence of the bis-anthracenyl units means that the compound (I) contains a built-in detection system. These conjugated groups tend to absorb and fluoresce strongly; they will naturally fluoresce on interrogation with radiation of an appropriate wavelength, and the intensity and/or wavelength of the emitted radiation will typically change when the compound associates with a saccharide molecule. This change in the emission spectrum can therefore be used to detect the presence or absence of a target saccharide such as glucose. Moreover, by adjusting the natures and/or positions of the substituents $R^1$ to $R^8$, the excitation and emission spectra of the compound (I) can be tailored so as to provide a response in a desired region of the electromagnetic spectrum (for example, in the visible region). Compounds of formula (I) can thus possess improved, or at least more adaptable, signalling properties compared to known receptors such as boronic acid-based receptors and the synthetic lectin 2.

The compounds of the present invention can therefore be expected to be of great value in blood glucose monitoring systems, including for continuous use.

In a compound of formula (I), the two aromatic, anthracene-based moieties and the two isophthaloyl moieties, together with the amide linking groups by which they are joined in a monocyclic structure, define a cavity which is capable of receiving a saccharide molecule, in particular glucose.

The anthracene moieties perform two functions. Firstly, they appear to contribute to the ability of the molecule to associate with—and its selectivity for—saccharide molecules, in particular those with one or preferably all equatorial groups, more particularly glucose. It is believed, although we do not wish to be bound by this theory, that the rigidity of the anthracene moieties helps to prevent collapse of the saccharide-receiving cavity of the molecule, thus maintaining a well-defined binding site. Secondly, these moieties provide a detectable response to electromagnetic radiation, which response can be affected by the presence of a saccharide molecule in the cavity, as explained in more detail below.

In an embodiment of the invention, the substituents $R^1$ to $R^8$ are each independently selected from hydrogen and polar groups. The presence of at least one polar group can help to increase the water solubility of the compound.

In an embodiment, at least one (suitably two or more, or four or more) of the substituents $R^1$ to $R^8$ is not hydrogen.

In an embodiment, $R^1$ to $R^8$ are each independently selected from hydrogen; optionally substituted heterocyclyl groups; optionally substituted alkenyl groups; optionally substituted alkynyl groups; optionally substituted aryl groups; optionally substituted heteroaryl groups; alkoxyl groups; ketone and aldehyde groups; carboxylic acids and carboxylate ions; carboxylate esters; —$SO_3H$; —$SO_3^-$; —$OSO_3H$; —$OSO_3^-$; —$PO_3XY$ where X and Y are independently hydrogen, alkyl or a negative charge; —$OPO_3XY$ where X and Y are independently hydrogen, alkyl or a negative charge; amines; amides; halo groups; —CN; —$NO_2$; —OH; and imino and imido groups, provided that in any one or more of the pairs $R^1R^2$, $R^3R^4$, $R^5R^6$ and $R^7R^8$, the two substituents may be joined together to form part of an optionally substituted cyclic group.

In an embodiment, the substituents $R^1$ to $R^8$ are each independently selected from hydrogen; alkoxyl groups; ketone and aldehyde groups; carboxylic acids and carboxylate ions; carboxylate esters; —$SO_3H$; —$SO_3^-$; —$OSO_3H$; —$OSO_3^-$; —$PO_3XY$ where X and Y are independently hydrogen, alkyl or a negative charge; —$OPO_3XY$ where X and Y are independently hydrogen, alkyl or a negative charge; amines; amides; halo groups; —CN; —$NO_2$; imino and imido groups; and cyclic groups fused to the anthracene unit to which they are attached.

In an embodiment, the substituents $R^1$ to $R^8$ are each independently selected from hydrogen, and substituents (including fused cyclic groups) which are capable of interacting electronically with the anthracene unit to which they are attached. Such electronic interactions typically involve the π-electrons of the anthracene rings. By way of example, a substituent which is capable of interacting electronically with an anthracene unit to which it is attached may be an electron-withdrawing substituent, and/or it may form a conjugated system with the thus-substituted anthracene unit, thereby extending conjugation through the chromophore moiety of the compound (I).

In this context, suitable electron-withdrawing substituents include for example alkoxyl groups; ketone and aldehyde groups; carboxylic acids and carboxylate ions; carboxylate esters; amides; halo groups; —CN; —$NO_2$; optionally substituted aryl groups, for example phenyl or naphthyl groups; optionally substituted alkenyl and alkynyl groups; optionally substituted heterocyclyl and heteroaryl groups; and imino and imido groups.

In an embodiment of the invention, one or more of $R^1$ to $R^8$—suitably two or more, or four or more—is a substituent which forms a conjugated system with the anthracene unit to which it is attached.

In an embodiment, the substituents $R^1$ to $R^8$ are each independently selected from hydrogen; carboxylate esters, in particular C1 to C4 esters such as methyl ester (—$CO_2CH_3$); alkoxyl groups, in particular C1 to C4 alkoxyl groups such as methoxyl, or in cases alkoxyl groups substituted with carboxylic acids, carboxylates or esters; optionally substituted cyclic imido groups; hydroxyl; and sulphonates such as —O—$SO_2$—$CF_3$. In an embodiment, the substituents $R^1$ to $R^8$ are each independently selected from hydrogen; carboxylate esters, in particular C1 to C4 esters such as methyl ester (—$CO_2CH_3$); alkoxyl groups, in particular C1 to C4 alkoxyl groups such as methoxyl; and optionally substituted cyclic imido groups. In an embodiment, the substituents $R^1$ to $R^8$ are each independently selected from hydrogen; carboxylate esters, in particular C1 to C4 esters such as methyl ester (—$CO_2CH_3$); and optionally substituted cyclic imido groups. A substituted cyclic imido group may in particular carry an optionally substituted alkyl group on the nitrogen atom of the ring: the alkyl group may for example be a methylene group —$CH_2$— which is itself substituted for instance with a carboxylate ester, in particular a C1 to C4 ester such as t-butyl ester.

In the present specification, substituents may be defined as follows.

An alkyl group may be either linear or branched. It may in particular be a C1 to C6 alkyl group, or a C1 to C4 alkyl group, or a C1 to C3 alkyl group, for example either methyl or ethyl. A C3 alkyl group may in particular be isopropyl. A C4 alkyl group may in particular be t-butyl.

A cycloalkyl group may be for example a C3 to C7 aliphatic hydrocarbon ring, in particular a 5- or 6-membered aliphatic hydrocarbon ring.

A heterocyclyl group is an aliphatic hydrocarbon ring which contains one or more heteroatoms selected from N, O, S and P, in particular from N, O and S. The ring may be a 3- to 7-membered ring, for example a 5- or 6-membered ring.

An alkenyl group contains one or more (for example two, or more particularly one) carbon-carbon double bonds. Again it may be either linear or branched, and/or may be or contain a cyclic moiety. It may in particular be a C2 to C6 alkenyl group, or a C2 to C4 alkenyl group, or a C2 to C3 alkenyl group.

An alkynyl group contains one or more (for example one) carbon-carbon triple bonds. It may be either linear or branched, and/or may be or contain a cyclic moiety. It may in particular be a C2 to C6 alkynyl group, or a C2 to C4 alkynyl group, or a C2 to C3 alkynyl group.

An aryl group is a group which contains one or more (for example one) aromatic hydrocarbon rings, for example phenyl, benzyl, tolyl, xylyl, naphthyl or anthracyl. It may for example be a C5 to C18 aryl group, or a C6 to C18 aryl group, or a C6 to C14 or C6 to C10 or C6 to C8 aryl group. It may in particular be phenyl or benzyl, more particularly phenyl.

A heteroaryl group is a group containing one or more (for example one) aromatic hydrocarbon rings, which rings each contain one or more heteroatoms selected from N, O, S and P, in particular from N, O and S. Such a ring may be a 3- to 7-membered ring, for example a 5- or 6-membered ring.

An alkoxyl group comprises the terminal group —O—$R^{11}$.

A ketone group comprises the terminal group —C(O)—$R^{11}$. An aldehyde group comprises the terminal group —C(O)—H.

A carboxylic acid group comprises the terminal group —$CO_2H$. It may for example comprise a C1 to C4 carboxylic acid, or a C1 to C2 carboxylic acid, such as —$CH_2CO_2H$ or —$CO_2H$. It is to be understood that such a group may be present, depending on its environment, in the form of the corresponding carboxylate ion —$CO_2^-$. A carboxylate ester comprises the terminal group —$CO_2R^{11}$.

An amine group comprises the group —$N(R^2)_2$. In general it may be a primary amine, in which both $R^{12}$ groups are hydrogen; a secondary amine, in which one of the $R^{12}$ groups is hydrogen; or a tertiary amine, in which neither of the $R^{12}$ groups is hydrogen. In some cases the nitrogen atom may form part of a heterocyclic or heteroaryl ring, for example a 5- or 6-membered ring.

An amide group comprises the group —C(O)—$N(R^2)_2$. In general it may be a primary amide, in which both $R^{12}$ groups are hydrogen; a secondary amide, in which one of the $R^{12}$ groups is hydrogen; or a tertiary amide, in which neither of the $R^{12}$ groups is hydrogen. In some cases the nitrogen atom may form part of a heterocyclic or heteroaryl ring, for example a 5- or 6-membered ring.

A halo group may for example be selected from fluoro, chloro, bromo and iodo groups, or from fluoro, chloro and bromo groups, or from fluoro and chloro groups.

An imino group comprises the group —C(=$NR^{13}$)$R^{12}$, which may be a terminal group or may form part of a longer chain or of a heterocyclic or heteroaryl ring, for example a 5- or 6-membered ring.

An imido group comprises the group —C(O)—$NR^{13}$—C(O)—$R^{12}$, which may be a terminal group or may form part of a longer chain or of a heterocyclic or heteroaryl ring, for example a 5- or 6-membered ring.

A sulphonate comprises the group —O—$SO_2$—$R^{11}$.

In the above definitions, any group $R^{11}$ (independently of any other $R^{11}$ group which is present) may be selected from optionally substituted alkyl, cycloalkyl, heterocyclyl, alkenyl, alkynyl, aryl and heteroaryl groups; carboxylic acids and carboxylate ions; carboxylate esters; alkoxyl groups; ketone and aldehyde groups; amine and amide groups; and halo groups. It may be selected from optionally substituted alkyl, cycloalkyl, heterocyclyl, alkenyl, alkynyl, aryl and heteroaryl groups. It may be selected from optionally substituted alkyl, cycloalkyl, alkenyl and aryl groups. It may in particular be optionally substituted (for example unsubstituted) alkyl, more particularly C1 to C4 alkyl or C1 to C3 alkyl or C1 to C2 alkyl, for example methyl. In particular in the context of alkoxyl groups useable as groups $R^1$ to $R^8$, $R^{11}$ may include a carboxylic acid or carboxylate ion or ester; it may for example be —$CH_2CO_2H$ or —$CH_2CO_2R^{27}$, where $R^{27}$ is an alkyl group, in particular a C1 to C4 alkyl group such as t-butyl. In particular in the context of carboxylate esters useable as groups $R^1$ to $R^8$, $R^{11}$ may be an optionally substituted, suitably unsubstituted, alkyl group, for example a C1 to C5 or C1 to C4 alkyl group such as methyl or ethyl.

Any group $R^{12}$ (independently of any other $R^{12}$ group which is present) may be selected from hydrogen; a group $R^{11}$ as defined above; and in certain cases, as appropriate, a bond by which the relevant substituent is linked to another part of the molecule.

Any group $R^{13}$ (independently of any other $R^{13}$ group which is present) may be selected from hydrogen; optionally substituted alkyl; —OH; alkoxyl; amine; and in certain cases, as appropriate, a bond by which the relevant substituent is linked to another part of the molecule. $R^{13}$ may in particular be selected from hydrogen and optionally substituted (for example ester-substituted) alkyl, or from hydrogen and unsubstituted alkyl.

An "optionally substituted" group may be substituted with one or more, for example one or two, substituents, which substituents may for example be selected from alkyl, cycloalkyl, heterocyclyl, alkenyl, alkynyl, aryl and heteroaryl groups; carboxylic acids and carboxylate ions; carboxylate esters; alkoxyl groups; ketone and aldehyde groups; amine and amide groups; halo groups; —OH; —CN; and —$NO_2$.

Such substituents may in particular be selected from alkyl, more particularly C1 to C4 alkyl or C1 to C3 alkyl or C1 to C2 alkyl, for example methyl; aryl, for example phenyl or benzyl, in particular phenyl; carboxylic acids and carboxylate ions, for example —$CH_2CO_2H$, —$CO_2H$ or the corresponding anions; alkoxyl, for example ethoxyl or methoxyl, in particular methoxyl; amine and amide groups, in particular primary amine and amide groups; halo groups; and —OH. More particularly, such substituents may be selected from alkyl, for example C1 to C4 alkyl or C1 to C3 alkyl or C1 to C2 alkyl, such as methyl; aryl, for example phenyl or benzyl, in particular phenyl; alkoxyl, for example ethoxyl or methoxyl, in particular methoxyl; and —OH. Yet more particularly, they may be selected from alkyl groups, for example C1 to C4 alkyl or C1 to C3 alkyl or C1 to C2 alkyl, such as methyl.

In particular in the context of $R^1$ to $R^8$, such optional substituents may in particular be electron-withdrawing substituents, and/or may be selected from alkoxyl groups; ketone and aldehyde groups; carboxylic acids and carboxylate ions; carboxylate esters; amines; amides; halo groups; —CN; —$NO_2$; optionally substituted aryl groups, for example phenyl, benzyl or naphthyl groups; optionally substituted alkenyl and alkynyl groups; optionally substituted heterocyclyl and heteroaryl groups; and imino and imido groups. Thus, for example, an optionally substituted alkenyl group may be substituted with one or more additional electron-withdrawing groups such as —CN, as in CH=CHCN.

An "optionally substituted" group may in particular be unsubstituted.

A substituent $R^1$ to $R^8$ may include a degree of unsaturation; it may for example include a carbon-carbon double bond, a carbonyl group C=O and/or an imino group C=N, in particular C=C. It may form a conjugated system with the anthracene unit to which it is attached, thereby extending conjugation through the chromophore moiety of the compound (I). In an embodiment of the invention, one or more (for example 2 or more, or 4 or more) of $R^1$ to $R^8$ is a substituent which includes a degree of unsaturation. In an embodiment, one or more (for example 2 or more, or 4 or more) of $R^1$ to $R^8$ is a substituent which extends conjugation through the relevant anthracene moiety.

A cyclic group containing a pair of substituents $R^1R^2$, $R^3R^4$, $R^5R^6$ or $R^7R^8$ may for example be an n-membered ring, in which n is typically from 3 to 7 or from 3 to 6 or from 4 to 6, such as either 5 or 6, in particular 5. n may represent the number of carbon atoms in the ring. Alternatively, the ring may contain one or more heteroatoms such as O and/or N, in particular N. It may contain one or more C=O groups. The ring may be substituted with one or more, for example one or two, substituents, for example selected from electron-withdrawing substituents such as those referred to above. Any two or more of such substituents may themselves be joined to form an additional fused cyclic group. However, in cases it may be preferred for a ring which is formed by a pair of substituents from $R^1$ to $R^8$ not to be further substituted.

The n-membered ring may be aliphatic or aromatic, suitably aromatic; again, it may extend conjugation through the relevant anthracene unit.

In an embodiment, at least one of, for example each of, the two pairs $R^1R^2$ and $R^3R^4$ forms an optionally substituted cyclic group. In an embodiment, at least one of, for example each of, the two pairs $R^5R^6$ and $R^7R^8$ forms an optionally substituted cyclic group. In an embodiment, at least one of, for example each of, the two pairs $R^1R^2$ and $R^7R^8$ forms an optionally substituted cyclic group. In an embodiment, each of the four pairs $R^1R^2$, $R^3R^4$, $R^5R^6$ and $R^7R^8$ forms an optionally substituted cyclic group. Such cyclic groups may be of the type just described.

Thus, either or both of the anthracene moieties in the compound (I) may comprise a tetracyclic or pentacyclic condensed ring system. In an embodiment, either or both (suitably both) of the anthracene moieties comprises a pentacyclic condensed ring system. Such condensed ring systems are suitably aromatic.

In an embodiment, one or more of the pairs of substituents $R^1R^2$, $R^3R^4$, $R^5R^6$ and $R^7R^8$ forms an optionally substituted cyclic imido group, in particular a 5-membered cyclic imide, in which the ring nitrogen atom may be substituted for example with a group $R^{11}$ or $R^{13}$ as defined above, in particular with an alkyl group such as a C1 to C4 alkyl group. Such alkyl groups may themselves be substituted with one or more electron-withdrawing substituents such as those discussed above, for example selected from carboxylic acids and carboxylate ions; alkoxyl groups; and esters, in particular esters. In an embodiment, either or both (suitably both) of the pairs $R^1R^2$ and $R^7R^8$ forms such a cyclic imide. In an embodiment, either or both (suitably both) of the pairs $R^3R^4$ and $R^5R^6$ forms such a cyclic imide. Thus, in a further embodiment, each of the four pairs may form such a cyclic imide.

In a specific embodiment, such a cyclic imide is a 5-membered ring of which the nitrogen atom is substituted with an ester-substituted alkyl group, for example of the formula —$(CH_2)_nCO_2$—$R^{11}$ where n is an integer from 1 to 3, suitably 1, and $R^{11}$ is as defined above and may in particular be a C1 to C5 or C1 to C4 alkyl group, for example t-butyl.

In an embodiment, either or both (suitably both) of $R^1$ and $R^7$ may be selected from groups of the formula —C(O)—$R^{11}$, where $R^{11}$ is as defined above and is in particular C1 to C4 alkyl. More particularly, either or both (suitably both) of $R^1$ and $R^7$ may be —C(O)CH$_3$.

In an embodiment, one or more (suitably all) of the groups $R^1$ to $R^8$ are selected from ester groups of the formula —$CO_2$—$R^{11}$, where $R^{11}$ is as defined above and is in particular C1 to C4 alkyl, for example methyl or ethyl, in particular methyl.

In an embodiment, $R^1$ to $R^4$ are all hydrogen. In an embodiment, $R^1$ to $R^8$ are all hydrogen.

In an embodiment of the invention, $R^1$=$R^7$, $R^2$=$R^8$, $R^3$=$R^5$ and $R^4$=$R^6$. Thus, the molecule may be symmetric as regards the natures of its two anthracene-based aromatic moieties. In an alternative embodiment, the molecule is asymmetric as regards the natures of the two anthracene moieties.

As mentioned above, the natures of the substituents $R^1$ to $R^8$ may be used to influence the wavelength at which the compound (I) absorbs and/or emits electromagnetic radiation, and thus to tailor it for use in a desired context. By way of example, the substituents $R^1$ to $R^8$ may be chosen so that the compound fluoresces in response to electromagnetic radiation. The substituents may be such that the compound absorbs and/or emits (suitably emits) radiation in the visible region of the electromagnetic spectrum (for example from about 400 to 700 nm), in particular in the red region (for example from about 580 to 700 nm), and/or in the near-infrared region (for example from about 700 to 1000 nm). They may be such that the compound absorbs and/or emits (suitably emits) radiation in a region of the spectrum to which body tissue is at least partially transparent, thus making it possible to detect a spectroscopic response in the compound from outside the body, even when the compound is present within the bloodstream. Such detection is explained in more detail below, and can facilitate the continuous monitoring of blood glucose levels using the compounds of the invention.

In an embodiment, the peak emissions wavelength for the compound (I) is greater than 450 nm, in order to avoid the main absorption wavelength of haemoglobin. Its peak emissions wavelength may be 500 nm or greater, or 550 or ideally 600 nm or greater, as in these regions the body absorbs relatively little electromagnetic radiation.

In this way, the natures of the two anthracene moieties of the compound (I) can influence its detectability. A substituent which extends the conjugation through the relevant anthracene moiety can thereby increase the wavelength of the electromagnetic radiation which the compound emits following excitation. The tailoring of the compound, via its substituents $R^1$ to $R^8$, can be achieved relatively easily using the preparation methods described below. Structural and binding studies, such as are described in the examples below, indicate that a saccharide molecule which complexes with the compound (I) will reside in the cavity defined by its macrocyclic structure, and be unlikely to make contact with substituents at the peripheries of the anthracene moieties: thus, modification of the substituents $R^1$ to $R^8$ is believed to be unlikely to limit the affinity of the compound for a target saccharide such as glucose, or its selectivity for such a target.

The substituents $R^1$ to $R^8$ may also be used to influence the photostability of the compound (I). For example, the presence of one or more electron-withdrawing groups may enhance photostability, thus making the compound better suited for medical applications.

In a compound of formula (I), the isophthaloyl moieties can perform two functions. Firstly, they link together the two anthracene moieties, in a manner suitable to create a space or cavity which can be occupied by a saccharide molecule. Secondly, their substituents $R^9$ and $R^{10}$ can be used to confer one or more additional functionalities on the molecule as a whole. $R^9$ and $R^{10}$ may for example contribute to the water solubility of the molecule, facilitating its use in an aqueous environment such as blood. Instead or in addition, they may contain polymerisable groups which, as described in more detail below, allow the molecule to be incorporated into a polymeric structure.

In an embodiment of the invention, at least one of $R^9$ and $R^{10}$ is a hydrophilic substituent. Suitably, $R^9$ and $R^{10}$ are each independently selected from hydrogen and hydrophilic substituents, provided that at least one of $R^9$ and $R^{10}$ is a hydrophilic substituent. In an embodiment, both $R^9$ and $R^{10}$ are hydrophilic substituents. Instead or in addition, one or more of the substituents $R^1$ to $R^8$ may be a hydrophilic substituent. What is important is that the substituents $R^1$ to $R^{10}$ are together chosen so that the compound (I) as a whole is water-soluble. It is suitably soluble in water to a level of at least 1 µM, preferably at least 1 mM.

In an embodiment of the invention, one or more of the substituents $R^1$ to $R^{10}$, in particular of $R^9$ and $R^{10}$, is a hydrophilic substituent. In an embodiment, $R^9$ and $R^{10}$ are each independently selected from hydrogen and hydrophilic substituents, and suitably at least one of $R^9$ and $R^{10}$ is a hydrophilic substituent. In an embodiment, either or both of $R^9$ and $R^{10}$ (preferably both) is a hydrophilic substituent.

A hydrophilic substituent is a substituent which contains one or more hydrophilic functional groups, for example selected from polar groups such as carboxylic acids, carboxylate ions, carboxylate esters, hydroxyl, amines, amides, ethers, ketone and aldehyde groups, $—NO_2$, sulphates, sulphonates, phosphates, phosphonates, and combinations thereof. Such hydrophilic functional groups may be selected from carboxylic acids, carboxylate ions, carboxylate esters, hydroxyl, amines, amides, ethers, ketone and aldehyde groups, and combinations thereof, or in particular from carboxylic acids, carboxylate ions, amides, ethers, and combinations thereof, more particularly from carboxylic acids and carboxylate ions.

Since a compound of formula (I) would otherwise (ie if all of $R^1$ to $R^{10}$ were hydrogen) be inherently hydrophobic, at least one of the substituents $R^1$ to $R^{10}$ (for example at least one of $R^9$ and $R^{10}$) suitably possesses strongly hydrophilic properties. For this reason, it may be preferred for a hydrophilic substituent to comprise more than one, for example 2 or 3 or more, suitably 5 or 7 or 9 or more, hydrophilic functional groups such as those listed above. In cases it may comprise 10 or 15 or 20 or more hydrophilic functional groups, or in cases 25 or 30 or more. A hydrophilic substituent may for example be selected from substituents comprising polycarboxylic acid, polycarboxylate, polyhydroxy, polyester, polyether, polyamine, polyamide, polyphosphate and/or polyoxyalkylene (in particular polyoxyethylene) units, or from substituents comprising polycarboxylic acid, polycarboxylate and/or polyamide units, or from substituents comprising polycarboxylic acid and/or polycarboxylate units.

In an embodiment, a hydrophilic substituent (for example $R^9$ and/or $R^{10}$) may be a hydrocarbyl group substituted with one or more, for example 2 or more, for example 3, hydrophilic terminal groups such as in particular carboxylic acids or carboxylate ions. Such a hydrocarbyl group may be substituted with 5 or 6 or more, or in cases 9 or more, hydrophilic terminal groups such as carboxylic acids or carboxylate ions. It may be substituted with 10 or 15 or 20 or 25 or 30 or more such hydrophilic functional groups. A hydrocarbyl group may be defined as any group containing both hydrogen and carbon atoms, and optionally also one or more heteroatoms such as O, N, S and/or P, in particular O, N and/or S. Such a hydrocarbyl group ideally also incorporates one or more non-terminal polar groups, for example selected from secondary and tertiary (in particular secondary) amines, secondary and tertiary (in particular secondary) amides, ethers, and combinations thereof.

In an embodiment, a substituent $R^9$ or $R^{10}$ may be selected from groups of the formula $—C(O)—R^{14}$, where $R^{14}$ is a hydrophilic substituent as defined above. In a preferred embodiment, either or both (suitably both) of $R^9$ and $R^{10}$ is independently selected from groups of the formula $—C(O)—R^{14}$.

In an embodiment, $R^{14}$ is a group $—NR^{15}C(R^{16}CO_2H)_3$ in which $R^{15}$ is selected from hydrogen and C1 to C4 alkyl, or from hydrogen and C1 to C2 alkyl, and in particular is hydrogen; and $R^{16}$ is a group $(CH_2)_n$, where n is an integer from 1 to 6 or from 2 to 4, for example 2 or 3, optionally containing an ether group $—O—$. The or each $R^{16}$ may for example be $—CH_2O—CH_2CH_2—$. In an embodiment, a hydrophilic substituent such as $R^9$ and/or $R^{10}$ is a group $—C(O)NHC(R^{16}CO_2H)_3$, or a group $—C(O)NR^{15}C(CH_2OCH_2CH_2CO_2H)_3$, in which $R^{15}$ and $R^{16}$ are as defined above. In particular, a hydrophilic substituent such as $R^9$ and/or $R^{10}$ is a group $—C(O)NHC(CH_2OCH_2CH_2CO_2H)_3$.

In an embodiment, $R^{14}$ is a group $—NR^{15}C(R^{17})_3$ in which $R^{15}$ is as defined above; $R^{17}$ is a group $—R^{18}C(O)NR^{15}—C(R^{18}CO_2H)_3$; and each $R^{18}$ is independently selected from groups $R^{16}$ as defined above. The or each $R^{18}$ may for example be $—CH_2O—CH_2CH_2—$, or it may for example be $—CH_2CH_2—$. The $R^{15}$ groups need not all be the same, though are suitably all hydrogen.

Thus, $R^{14}$ may be a group of formula (X) below:

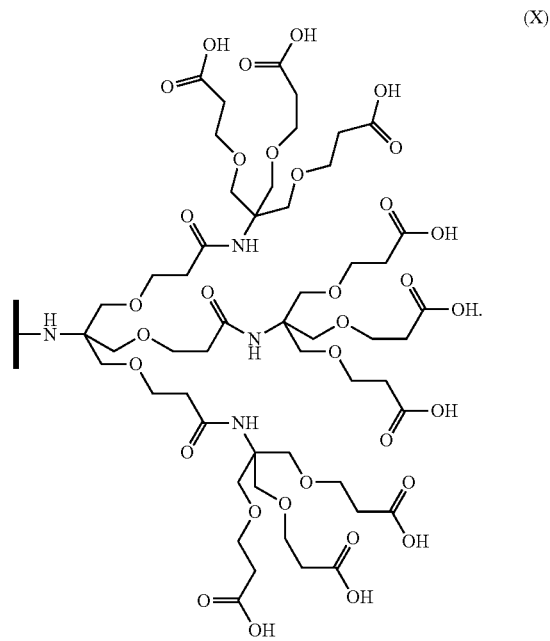

Alternatively R$^{14}$ may be a group of formula (XI) below:

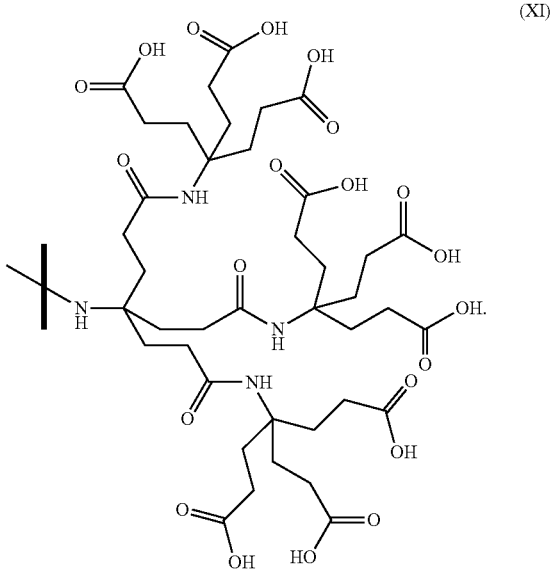

(XI)

In an embodiment, R$^{14}$ is a group —NR$^{15}$C(R$^{25}$)$_3$ in which R$^{15}$ is as defined above; R$^{25}$ is a group —R$^{18}$C(O)NR$^{15}$—C(R$^{26}$)$_3$; R$^{26}$ is a group —R$^{18}$C(O)NR$^{15}$—C(R$^{18}$CO$_2$H)$_3$; and each R$^{18}$ is independently selected from groups R$^{16}$ as defined above, for example —CH$_2$CH$_2$—. Again, the R$^{15}$ groups need not all be the same, though are suitably all hydrogen.

Thus, R$^{14}$ may be a group of formula (XII) below:

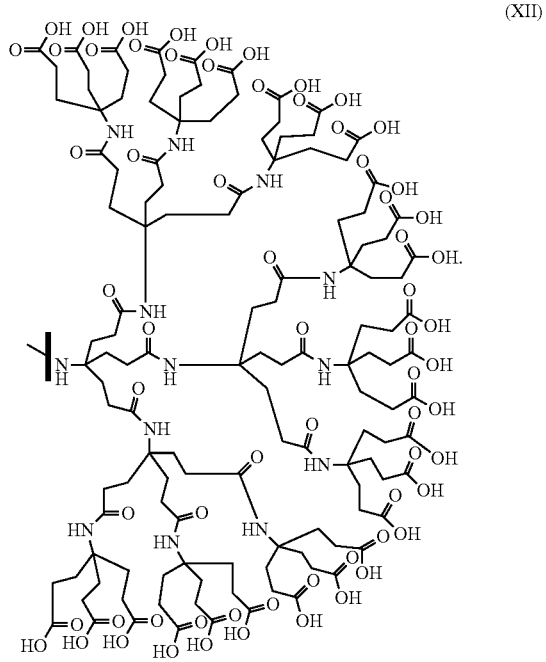

(XII)

In a group R$^{14}$, it is possible that each group R$^{16}$, and/or each group R$^{17}$, and/or each group R$^{18}$, and/or each group R$^{25}$, and/or each group R$^{26}$, is the same.

In a more specific embodiment of the invention, the compound (I) is a compound 3, 13 or 14 as described in the examples below. In particular it may be a compound 13 or 14, more particularly a compound 14. In each case, such a compound may be present in the form of a salt or a protected form such as an ester. In particular where terminal carboxylic acid groups are present, for example as part of a solubilising group R$^9$ or R$^{10}$, they may be present as acids or as carboxylate anions, or as corresponding esters such as C1 to C4 esters.

Any carboxylic acid-containing group R$^{14}$ may be used in the form of its carboxylate equivalent, in which the groups —CO$_2$H are present as the corresponding anions —CO$_2^-$.

In a carboxylic acid-containing group R$^{14}$ of the type described above, one or more (suitably one) of the groups —C(R$^{16}$CO$_2$H)$_3$, —C(R$^{18}$CO$_2$H)$_3$, —C(R$^{17}$)$_3$, —C(R$^{25}$)$_3$ or —C(R$^{26}$)$_3$ may be replaced by another moiety which introduces a specific functionality into the molecule. For example, such a moiety may be a polymerisable functional group, as described in more detail below. It has been found that the periphery of an R$^9$ or R$^{10}$ group can be modified without unduly compromising the saccharide binding, selectivity and spectroscopic responses of the compound (I), in particular when the group is a larger hydrophilic substituent, for example of formula (X), (XI) or more particularly (XII) above.

In an embodiment of the invention, R$^9$ and R$^{10}$ are the same. In an alternative embodiment, R$^9$ and R$^{10}$ are different.

Compounds which are structurally similar to compound (I) have been prepared in the past by Baumes et al [see for example *Nature Chemistry* advance online publication, 24 Oct. 2010, DOI: 10.1038/NCHEM.871]. Those compounds were, however, hydrophobic, and thus inherently unsuitable for use in an aqueous environment such as blood. They were disclosed for use in the preparation of squaraine rotaxane endoperoxides, intended for use as fluorescent and chemiluminescent dyes. Similar compounds, also hydrophobic and also for use in the preparation of chemical dyes, have been described by Gassensmith et al in *J Am Chem Soc* 2007, 129: 15054-15059; by Collins et al in *Chem Commun*, 2011, 47: 12352-12354; by Lee et al in *Chem Commun*, 2011, 47: 7188-7190; by Murgu et al in *J Org Chem*, 2011, 76: 688-691; by Baumes et al in *Org Lett*, 2010, 12 (no. 21): 4980-4983; and by Gassensmith et al in *Org Lett*, 2008, 10 (no. 15): 3343-3346 (see also Gassensmith et al in *Chem Commun*, 2009: 2517-2519, and WO-2011/087521).

A compound (I) according to the invention is suitably capable of complexing with a target saccharide. Such complexing ideally does not involve the formation of covalent bonds, but instead weaker interactions such as CH-π interactions and/or polar interactions between saccharide OH groups and polar regions of the compound (I) molecule. Ideally it results in a reversible, suitably equilibrium, association between the target saccharide and the compound (I) if both are present in the same aqueous environment. A reversible association is a particular advantage when continuously monitoring changing concentrations of the target saccharide, for example fluctuating blood glucose levels.

In particular, the compound (I) may be capable of complexing with a saccharide which carries one or more equatorial substituents, more particularly with an all-equatorial saccharide, yet more particularly with a saccharide which contains an all-equatorial β-glucosyl unit, and most particularly with glucose.

The compound (I) suitably exhibits a spectroscopic response on complexing with a target saccharide, in particular glucose. By "spectroscopic response" is meant a change in the ability of the compound to absorb, reflect, transmit and/or emit electromagnetic radiation, in particular in the region from about 300 to 1000 nm, more particularly in the near-infrared or visible region (for example from about 400 to 1000 nm), yet more particularly in the near-infrared and/or visible red region (for example from about 580 to 700 nm or from about 580 to 1000 nm). The spectroscopic response may for example comprise a change in the wavelength at which the compound emits electromagnetic radiation when excited using an applied electromagnetic wave, and/or the degree to which (ie the intensity with which) it emits electromagnetic radiation, at any given wavelength, following excitation. In both cases, the response can provide an indication of the presence or absence of complexing between the compound (I) and the target saccharide, and/or of the amount or degree of such complexing. In particular, the spectroscopic response may comprise a change in the intensity with which the compound (I) emits electromagnetic radiation, in particular at its peak emission wavelength, following excitation.

In an embodiment, the spectroscopic response is detectable in the visible (in particular the red) region of the electromagnetic spectrum, and/or in the infrared or near-infrared region. For example, the compound (I) may fluoresce in response to an applied electromagnetic wave, and the wavelength at which it fluoresces (suitably both in the presence and the absence of complexing with the target saccharide) may be in the visible and/or the near-infrared region of the electromagnetic spectrum.

Again, the substituents $R^1$ to $R^8$ may be tailored so as to influence the spectroscopic response of the compound (for example the wavelength at which, and/or the degree to which, the response occurs).

The compound (I) suitably has a binding affinity with the target saccharide, in particular with glucose, such that the binding constant $K_a$ is 10 $M^{-1}$ or greater. In an embodiment, $K_a$ is 20 or 30 $M^{-1}$ or greater, or 40 or 50 $M^{-1}$ or greater. It may for example be up to 200 $M^{-1}$, or up to 150 $M^{-1}$ or up to 130 or 100 or in cases 75 $M^{-1}$, such as from 10 to 200 $M^{-1}$ or from 30 to 100 $M^{-1}$ or from 50 to 100 $M^{-1}$ The binding affinity with the target saccharide, in particular glucose, is ideally such as to make the compound (I) suitable for detecting the target in the bloodstream of a human or animal (in particular mammalian, more particularly human) patient. Such detection suitably involves detection of the spectroscopic response of the compound (I) to complexing with the target saccharide, as described above. Too low a binding affinity, and the complexing will not be readily detectable. Too high a binding affinity, however, and the compound (I) may become saturated even at relatively low target concentrations, thus rendering it unsuitable for the detection of a wider range of target saccharide concentrations. In a "normal", healthy human patient, blood glucose concentrations range from 2 to 13 mM; ideally, the complex formed between the compound (I) and the target saccharide (in particular glucose) will be capable of detection, without saturation, at target saccharide concentrations up to about 50 mM, or up to about 30 mM, for example from about 0.1 to 20 mM or from 1 to 20 mM or from 2 to 20 mM.

In a preferred embodiment, the compound (I) is selective for glucose relative to other mono- and disaccharides, in particular relative to saccharides (such as galactose and/or fructose) which are likely also to be present in the bloodstream. The compound (I) may for instance have a binding affinity for glucose which is at least 1.5 times as great as its binding affinity for other mono- or disaccharides, or at least 1.75 or 2 times as great, or in cases at least 5 or 10 times as great. Suitably, the compound (I) is selective for glucose relative to other potentially competing analytes which are likely to be present in the bloodstream of a patient in which the compound is used to detect blood glucose levels: such competing analytes may include for example lactates and mannitol.

Binding affinities, and hence selectivities, may be measured using known methods such as NMR spectroscopy, fluorescence titration and/or isothermal titration calorimetry, for instance as described in the examples below. They are suitably measured in an aqueous environment, for example in blood. They may be measured at ambient temperature, or more suitably at a temperature which is at or close to body temperature, for example between 30 and 40° C. or between 35 and 40° C.

Suitably, the compound (I) exhibits a readily detectable spectroscopic response in the presence of the target saccharide, in particular glucose. In an embodiment, the intensity with which it emits electromagnetic radiation following excitation (ie the intensity with which it fluoresces), measured at its peak emission wavelength, changes by at least 5%, or by at least 10 or 25%, or in cases by at least 50 or 75 or even 100%, due to complexing with the target saccharide. In an embodiment, the intensity of the emitted radiation increases due to such complexing. In an embodiment, the wavelength at which the compound (I) emits electromagnetic radiation following excitation changes by at least 5%, or by at least 10 or 25%, or in cases by at least 50 or 75 or even 100%, due to complexing with the target saccharide.

Preferred compounds of formula (I) are those which are acceptable for pharmaceutical (which may include veterinary) use, in particular those which can be safely introduced into the bloodstream of a human or animal patient. Also preferred are those compounds which exhibit a reasonable degree of photostability under physiological conditions, ie when present in the bloodstream of a living human or animal patient.

According to a second aspect of the present invention, there is provided a compound of formula (Ia), which is a compound of formula (I) which additionally incorporates one or more polymerisable functional groups. Such a compound need not necessarily itself be water-soluble, so long as it can be incorporated into a water-soluble or hydratable polymer.

By "polymerisable functional group" is meant a group which can (following suitable activation, for example with a polymerisation initiator) react with another such group on another molecule, to form part of a polymer or copolymer with that other molecule. The "other molecule" in this context may be another molecule of the same formula (Ia), a molecule of a different formula (Ia), or a molecule of another monomer or polymer. Suitable polymerisable functional groups include for instance acrylamide and alkylacrylamide (for example methylacrylamide or dimethylacrylamide) groups, acrylate and alkylacrylate (for example methacrylate) groups, vinyl groups C=C, and combinations thereof.

In a compound (Ia), the polymerisable functional group(s) may be attached to, or incorporated as part of, any one or more of the substituents $R^1$ to $R^{10}$, in particular $R^9$ and $R^{10}$. Thus, in an embodiment of the invention, either or both (suitably both) of $R^9$ and $R^{10}$ incorporates a polymerisable functional group: the relevant substituent $R^9$ and/or $R^{10}$ need not necessarily be hydrophilic.

By way of example, in a compound (Ia) either or preferably both of the groups $R^9$ and $R^{10}$ may comprise an acrylamide group —NH—C(O)—CH=CH$_2$. The resulting compound may then be co-polymerised with acrylamide monomers and/or other ingredients (including, for example, linking units such as polyoxyalkylenes), to provide polymeric matrices—such as gels—which incorporate the saccharide-complexing ability of the compound of the invention.

The term "polymer" in this context embraces an oligomer. It also embraces a copolymer.

A polymer formed in this way may be insoluble in water, but hydratable (ie capable of being penetrated by water molecules, and hence by saccharide molecules present in an aqueous environment).

A third aspect of the invention provides a polymer which incorporates a compound according to either the first or the second aspect—ie a monomer of formula (I) or (Ia)—in its structure. The polymer is suitably water-soluble and/or hydratable. The compound (I) or (Ia) is suitably chemically linked to the remainder of the polymer via one or more polymerisable functional groups, which may form part of one or more groups $R^1$ to $R^{10}$, in particular of the groups $R^9$ and/or $R^{10}$.

In an embodiment, the polymer is water-soluble: it may for instance be soluble in water to a level of at least 1 µM, preferably at least 1 mM.

In an embodiment, the polymer is in the form of a gel, in particular a hydrogel, which may for example be used in the form of beads to immobilise the compound (I) or (Ia). The polymer may, for example, consist of cross-linked polyethylene glycol (PEG) and/or polyacrylamide chains, suitably solvated with water.

Incorporation of the compound (Ia) into a polymeric structure, via a suitable functional group, can provide a way of introducing the compound (I) into or onto a support or other form of carrier, and hence facilitate its delivery to a desired location. It may for example allow the compound to be used as part of the chemical structure of a gel-like polymer, for example a cross-linked polymer, such as a polyacrylamide. It may allow the compound to be bound to a polymeric surface, for instance of a probe or other device suitable for introduction into the bloodstream. Such uses for the invented compounds are described in more detail below.

In another embodiment, the compound (I) or (Ia) may be physically incorporated within the polymer structure, without being covalently bound to the polymer. Such a system may rely on non-covalent interactions between the compound (I) or (Ia) and the polymer, for example hydrogen bonding and/or ionic bonds, in order to retain the desired physical structure. In cases, it may remove the need to chemically modify the compound (I) with polymerisable functional groups.

According to a fourth aspect, the present invention provides a composition for use in the detection of a target saccharide in an aqueous environment, the composition comprising a compound according to the first or second aspect of the invention, or a polymer according to the third aspect, together with a carrier.

The detection of the target saccharide may comprise qualitative and/or quantitative assessment, ie of the presence or absence of the target in the aqueous environment and/or of the quantity or approximate quantity of the target present. As described above, the target saccharide may in particular be an all-equatorial saccharide, more particularly glucose. The aqueous environment may be blood or a blood-derived product.

The carrier may for example comprise a solid, semi-solid (for example cream or gel) or liquid material, in particular a solid or semi-solid material. The carrier is suitably acceptable for pharmaceutical (which may include veterinary) use, in particular for human pharmaceutical use, and particularly for use in the bloodstream.

A composition according to the fourth aspect of the invention may comprise a multi-phase system such as an emulsion or solid suspension, in which the compound (I) or (Ia), or the polymer if appropriate, is present in or on a different phase to that of the carrier. The compound or polymer may for example be (micro)encapsulated in some way and dispersed in the carrier.

In an embodiment, the compound or polymer is immobilised on or in a solid or semi-solid support. The solid or semi-solid support may itself be the carrier, or may be provided within it (for example as a suspension). For example, the solid or semi-solid support may comprise a polymeric matrix, and/or may be in the form of a gel, for example a hydrogel. Suitable polymers include those discussed above in connection with the first to the third aspects of the invention. The compound (I) or (Ia) may itself form part of this polymer, or be chemically bound to it through suitable functional groups, as described above.

Other suitable carriers for the compound or polymer include conventional vehicles and excipients, in particular those which are pharmaceutically acceptable, as are well known to those skilled in the art.

A fifth aspect of the invention provides a device which carries a compound according to the first or second aspect of the invention, a polymer according to the third aspect, and/or a composition according to the fourth aspect, ideally in a form which is suitable and/or adapted for introduction into a human or animal, in particular human, body. Such a device may be of particular use in the continuous or semi-continuous monitoring of blood glucose levels. Once introduced into the bloodstream, the compound (I) or (Ia), or the polymer as the case may be, will be in equilibrium association with any glucose present; its spectroscopic response will thus depend on the quantity of glucose in the blood. This response can be detected from outside the body, by interrogation of the device with electromagnetic radiation of an appropriate wavelength and detection of the resulting emissions.

The device is preferably suitable and/or adapted for implantation at a desired location within a human or animal, in particular human, body.

A device according to the invention may take any suitable form. It may comprise a pellet, tablet, capsule, chip or other form which may for example be capable of introduction into the bloodstream, for instance via a cannula. It may comprise, or be carried in or on, or be capable of being carried in or on, an implantable device such as a stent or probe. Ideally it takes a form which allows it to be introduced at, and ideally retained at, a desired location within the bloodstream, to facilitate detection. Implantable glucose-monitoring systems are already known in the art, for example in the form of glucose detector "chips" or receptor-bearing cables which can be introduced via a cannula. However, such known systems have relied on boronic acid-based receptors, which can suffer from certain disadvantages, as described above, compared to the receptor compounds (I) of the present invention.

A device according to the fifth aspect of the invention may carry a compound according to the first or second aspect, a polymer according to the third aspect and/or a composition according to the fourth aspect. The compound, polymer or composition may be carried on and/or in the device. The compound or polymer may be immobilised in or on a solid support, for example in the manner described above, which solid support forms part of the device.

In an embodiment, the device comprises a flexible cable, in particular a fibre optic cable, which is suitable and/or adapted for introduction into a blood vessel, in or on which cable is carried a compound or polymer or composition according to the invention. The compound or polymer or composition may be immobilised at a distal end of the cable, for instance by means of polymeric binding as described above. It may be applied to a distal end of the cable in the form of a composition such as a cream or gel. If the cable is a fibre optic cable, it may then also be used for introducing electromagnetic radiation with which to interrogate the compound or polymer, and/or for returning emitted radiation from the thus-excited compound or polymer to a suitable detector. Such a device may be convenient for medical use, as the tip of the cable may be replaceable after each use, or alternatively may be cleaned prior to application of a fresh quantity of a compound or polymer or composition according to the invention. Moreover, because electromagnetic radiation can be fed directly to a desired location via the fibre optic cable, there may be less need to tune the spectroscopic properties of the compound or polymer for instance to ensure that exciting radiation, or emitted radiation, can travel through body tissues.

A fibre optic glucose monitoring system is already known and marketed, but makes use of a chromophore-labelled boronic acid-based receptor rather than the compounds of the present invention. This existing system, together with the associated technology for detecting and processing spectroscopic data, could be readily adapted for use with a receptor compound (I) or (Ia) according to the invention.

A device according to the fifth aspect of the invention can be capable of operation without the need for a power source, as it can be interrogated from remotely.

According to a sixth aspect, the invention provides a detection system for detecting a target saccharide in an aqueous environment, the system comprising a compound according to the first or second aspect, a polymer according to the third aspect, a composition according to the fourth aspect and/or a device according to the fifth aspect, together with a detector for detecting a response (in particular a spectroscopic response) of the compound of formula (I) or (Ia), or the polymer as the case may be, to the target saccharide in the aqueous environment.

Preferred features of such a system may be as described above in connection with the first to the fifth aspects of the invention. In particular, the target saccharide may be glucose. The aqueous environment may be blood or a blood-derived product. The system may thus be for use in or as a blood glucose monitoring system. The detector may be for detecting a spectroscopic response of the compound or polymer on application of electromagnetic radiation.

The compound, polymer, composition or device may be provided in or on, or may take, any of the forms discussed above, in particular an implant, fibre optic cable or other device suitable for introduction into the body.

The detector may for instance take the form of a (preferably small) hand-held device, and/or a device (for example similar to a wrist watch) which is capable of being strapped to, or otherwise affixed to, the body of a human or animal patient. Such a device may be capable of receiving, and suitably also processing, electromagnetic radiation emitted by the compound (I) or (Ia), or by the polymer as the case may be, or in cases by another associated species such as a competitor species, and of providing an output comprising relevant information, in particular information regarding the concentration, or approximate concentration, of the target saccharide in the aqueous environment. Such a device could be used by a diabetic patient, and/or by a medical professional caring for a diabetic or other patient, in order to monitor the patient's blood glucose levels. It could therefore be used to help maintain a patient's blood glucose level within a desired, "safe", range, and/or to warn of the occurrence, or likely occurrence, of complications associated with raised or lowered blood glucose levels, for example hypoglycemia.

The output from the detector, typically in the form of a target saccharide concentration derived from a detected spectroscopic response, may be displayed for use by for instance a clinician or patient. It may be provided to another system, for example a system for supplying an active substance (such as insulin) to a patient, or a life-support machine, or a system for monitoring the health of a patient. Thus, the detection system may comprise an output means comprising for example (a) a display and/or (b) a connector or connection port via which it can provide information to another system or device.

A detection system according to the invention may additionally comprise interrogation means, for applying electromagnetic radiation to excite the compound or polymer in order to cause it to emit electromagnetic radiation in response. The wavelength of the applied radiation, and of the radiation emitted in response, will depend on the spectroscopic properties of the compound or polymer: typically, the emitted radiation will have a longer wavelength than that of the applied radiation. The wavelength of the emitted radiation may however vary in response to complexing of the compound or polymer with the target saccharide.

The interrogation means may suitably be incorporated into a device which also carries the detector.

In an embodiment, a detection system according to the invention incorporates a competitor species, of the type described in more detail below, in addition to the compound of formula (I) or (Ia) or the polymer.

A seventh aspect of the invention provides a supply system for supplying an active substance to an aqueous environment in response to a change in the concentration of a target saccharide in the aqueous environment, the system comprising (i) a detection system according to the sixth aspect of the invention, (ii) a supply of the active substance, (iii) delivery means for delivering the active substance from the supply to the aqueous environment, and (iv) control means for controlling delivery of the active substance in response to a concentration, or change in concentration, of the target saccharide which is detected by the detection system (i).

The control means (iv) may be capable of receiving a signal from the detection system, relating to a detected target saccharide concentration. It may also comprise comparator means, for comparing a detected target saccharide concentration with a predetermined value for a desired concentration of the target in the aqueous environment. The control means may then be capable of adjusting the rate, timing and/or quantity of delivery of the active substance to the environment, in response to a difference between the detected and predetermined concentrations, suitably in order to restore the target saccharide concentration to within, or to maintain the target saccharide concentration within, a desired range. The control means may for instance be capable of relaying an appropriate signal to the delivery means (iii), which may comprise a pump, valve and/or other flow control means between the supply (ii) and the aqueous environment. Such a system may thus be used to provide automatic control of the active substance delivery, in response to real-time feedback from the aqueous environment.

The aqueous environment may in particular be the bloodstream of a human or animal, especially human, body. The target saccharide may in particular be glucose. The active substance may comprise insulin.

In an embodiment, the active substance may comprise the target saccharide: thus, for example, the system may be used to deliver a target saccharide such as glucose in response to a reduced concentration of that target in the aqueous environment.

Accordingly, a system according to the seventh aspect of the invention may be suitable for use as, or as part of, a so-called "artificial pancreas", which is a closed-loop system able to continuously supply insulin to a patient to ensure their blood glucose levels remain within safe limits. It may be suitable for use as part of an intensive care life-support system, again to maintain blood glucose levels within safe limits. Aspects of the invention can provide such artificial pancreas or life-support systems. Once set up—for instance by implantation of a device according to the fifth aspect of the invention and installation of a detector at an appropriate location—the system could require relatively little intervention by either patient or carer.

According to an eighth aspect of the present invention, there is provided a method for detecting a target saccharide in an aqueous environment, the method comprising introducing, into the aqueous environment, a compound according to the first or second aspect of the invention, a polymer according to the third aspect, a composition according to the fourth aspect and/or a device according to the fifth aspect, and detecting a response of the compound or polymer, or of another associated species (for example a competitor species as described below), to the environment. The response may in particular be a spectroscopic response. A compound of formula (I) may be introduced into the aqueous environment in the form of a composition according to the fourth aspect of the invention, a device according to the fifth aspect, a compound of formula (Ia) as defined above and/or a polymer which incorporates the compound (I) or (Ia).

The target saccharide may be glucose. The aqueous environment may be blood (in particular human blood) or a blood-derived product.

The method of the eighth aspect of the invention may be for detecting the presence or otherwise of the target saccharide in the aqueous environment, and/or for detecting information about the concentration of the target saccharide in the environment. In the latter case, the method may provide an approximate indication of the target saccharide concentration (for example, indicating one or more ranges within which the target saccharide concentration falls) and/or a more precise indication. Suitably, the method involves detecting information about the concentration of the target saccharide.

A spectroscopic response of the compound or polymer to its environment may, as described above, comprise any change in the ability of the compound or polymer to absorb, reflect, transmit and/or emit electromagnetic radiation. In particular, it may comprise a change in the degree to which (ie the intensity with which) the compound or polymer emits electromagnetic radiation at any given wavelength, for example at its peak emission wavelength, following excitation using an applied electromagnetic wave. Such a response will be due to complexing of the compound or polymer with a target saccharide present in the aqueous environment, and can therefore provide an indication of the presence or absence of the target, and/or of its concentration in the environment.

A spectroscopic response may be detected by suitable spectroscopic means, for example by detecting a change in the electromagnetic absorption, reflectance, transmission and/or emission spectrum of the compound or polymer in the aqueous environment. The response may be assessed with reference to the spectroscopic properties of the compound or polymer prior to its introduction into the aqueous environment, and/or in an aqueous environment containing a known concentration of the target saccharide.

In general, references to "detecting" a spectroscopic response mean detecting either the presence, the absence and/or the nature and/or magnitude of such a response.

In an embodiment of the eighth aspect of the invention, the receptor compound or polymer is associated (whether by chemical and/or physical means) with another species, which because of its association with the compound or polymer—in particular a glucose-selective receptor—itself exhibits a detectable response which changes with the concentration of the target saccharide in the aqueous environment. The detectable response may for example be a (change in a) physical property such as mass or vibrational frequency. In such a detection method, the compound or polymer would not necessarily require tuning of its spectroscopic properties in order to provide an (indirectly) detectable indication of its complexing with the target saccharide.

The response of the compound or polymer to the target saccharide may be labelled, altered and/or amplified by the inclusion, with the compound or polymer, of a competitor species, which is able to associate with the compound or polymer unless replaced by the target saccharide for which the compound or polymer has a higher affinity. Displacement of the competitor species by the target saccharide may produce a greater, and/or more readily detectable, response than mere association of the compound or polymer with the target saccharide. The competitor species may for example be a saccharide mimic, and may for example have a lower affinity than the target saccharide for the compound or polymer, or be present at a lower concentration than the compound or polymer. In such a case, the competitor species may itself exhibit a detectable response, or it may be associated with another material, in the manner described above, and again the other material may thereby exhibit a detectable response which changes with the concentration of the target saccharide and thus the extent of displacement of the competitor species from the compound or polymer.

A method according to the eighth aspect of the invention may be carried out on blood which has been removed from a human or animal—in particular a mammalian, more particularly a human—body, or on a product derived from such blood.

The method may alternatively be carried out in vivo, in the blood of a human or animal (in particular a mammal, more particularly a human), especially a living human or animal.

The method may be carried out at a single point in time. However, in particular when carried out in vivo, it may be used to monitor the concentration of the target saccharide in the aqueous environment on a continuous or semi-continuous basis: the response of the compound, polymer or other species may be detected continuously over a period of time following its introduction into the aqueous environment, or at a plurality of discrete time-points following its introduction.

A method according to the eighth aspect of the invention may include an additional step of modifying the concentration of the target saccharide in the aqueous environment, for example by supplying a suitable active substance (in particular insulin and/or glucose) to the environment in response to a detected concentration, or change in concentration, of the target saccharide. This modification step may also be carried out at a single point in time, or over a period of time either continuously or at a plurality of discrete time-points, and/or in response to detected changes in the target saccharide concentration. Such a method may be used to help stabilise blood glucose levels in a patient.

A ninth aspect of the invention provides a method for the diagnosis and/or treatment of—or for use as part of a method for the diagnosis and/or treatment of—a condition which results in, or is otherwise associated with, an abnormal concentration of a target saccharide in a human or animal patient (in particular in the patient's bloodstream), which method comprises carrying out a method according to the eighth aspect of the invention on an aqueous sample which is either in or derived from the patient, and using the (typically spectroscopic) response of the compound (I) or (Ia), or the polymer or the other associated species as the case may be, to the sample in order to reach a decision regarding the nature and/or treatment of a condition from which the patient is suffering, and/or as part of a programme of treatment for the condition. Again, the target saccharide may in particular be glucose. The aqueous sample may in particular be blood or a blood-derived product. The condition may be diabetes, or a condition affecting the health of an intensive care or post-operative patient.

When used for diagnosis, such a method may be carried out either in vivo or on a sample (in particular blood) which has been removed from the patient's body or a product derived from such a sample. The decision as to the nature and/or treatment of the condition is suitably made by a clinician or other medical or veterinary professional. Detection of the response of the compound or polymer, whether qualitatively and/or quantitatively, and analysis of associated data, may however be carried out by technicians or other non-medical practitioners, or indeed by patients themselves, or may be wholly or partially automated (ie under machine control).

A method according to the eighth or the ninth aspect of the invention may be of particular use in the diagnosis and/or treatment of diabetic patients, and/or of intensive care or post-operative patients. It may for instance be used in the treatment of a diabetic patient, to assist in maintaining the patient's blood glucose levels within a desired range.

Where such methods are carried out in vivo, they may involve introducing the compound or polymer into a patient's bloodstream, for example in the form of a composition according to the fourth aspect of the invention and/or a device according to the fifth aspect. This introduction may involve a surgical procedure. Alternatively it may be carried out without surgery. A compound, polymer or composition may for instance be introduced using a syringe.

According to a tenth aspect, the invention provides a compound according to the first or second aspect, a polymer according to the third aspect, a composition according to the fourth aspect, a device according to the fifth aspect, and/or a detection or supply system according to the sixth or seventh aspect, for use in a method of diagnosis and/or therapy which is carried out on a living human or animal (in particular mammalian, more particularly human) body. In a specific embodiment of this aspect of the invention, the compound, polymer, composition, device and/or system is for use in the diagnosis and/or treatment of a condition (for example diabetes) which results in, or is otherwise associated with, an abnormal concentration of, and/or a change in the concentration of, a target saccharide in a human or animal patient (in particular in the patient's bloodstream). Again, the target saccharide may be glucose. The condition, its diagnosis and its treatment may be as described above in connection with the eighth and ninth aspects of the invention.

In particular, a compound, polymer, composition, device or system according to the invention may be used in the treatment of a diabetic patient, which treatment may comprise monitoring the patient's blood glucose levels and/or taking steps to maintain the blood glucose levels within a desired range.

According to an eleventh aspect of the invention, there is provided a method for the synthesis of a compound of formula (I) or (Ia)—in particular a compound of formula (I)—which method comprises at least a first step of reacting a bis-(aminomethylanthracene) compound of formula (II):

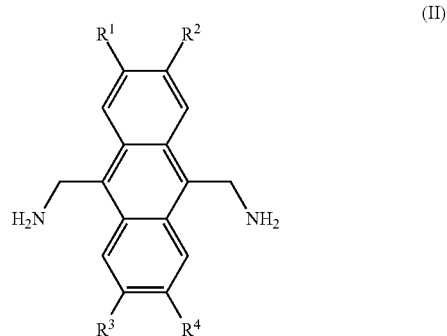

(II)

wherein $R^1$ to $R^4$ are as defined above in connection with the first aspect of the invention,
with a compound of formula (III):

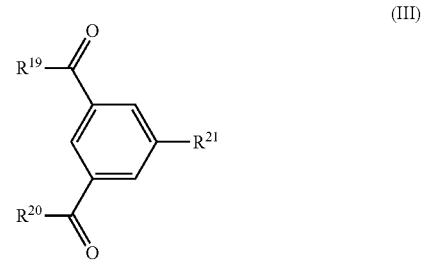

(III)

wherein $R^{19}$ is a leaving group L; $R^{20}$ is selected from a leaving group L and a protecting group $P^1$; $R^{21}$ is selected from groups $R^9$ as defined above, in which the or each reactive terminal group is protected by a protecting group $P^2$; and $P^1$ and all $P^2$ groups are each independently selected from protecting groups which are capable of preventing the substituent to which they are joined from reacting with a group —$NH_2$ under the chosen reaction conditions.

A leaving group L may for example be selected from groups of the formula —$OR^{22}$, where $R^{22}$ is a group suitable to stabilise the anion $R^{22}O^-$, thus rendering $R^{22}OH$ acidic; groups of the formula —$SR^{23}$, where $R^{23}$ is a group suitable to stabilise the anion $R^{23}S$, thus rendering $R^{23}SH$ acidic; halides; pseudohalides such as cyanides, (iso)cyanates, (iso)

thiocyanates and azides; and oxoacidic groups such as phosphate and sulphate. If the reaction between the compounds (II) and (III) is carried out in the presence of a carbodiimide or a phosphorous-based condensing agent such as BOP (benzotriazole-1-yl-oxy-tris-(dimethylamino)-phosphonium hexafluorophosphate), L may be hydroxyl.

In an embodiment, a leaving group L is selected from groups of the formula —OR. In an embodiment, L is —O-PFP, where PFP is pentafluorophenyl.

The group $R^{20}$ may also be a leaving group L of the type described above. In an embodiment, $R^{20}$ is —O-PFP. Thus, the groups $R^{19}$ and $R^{20}$ may be the same.

The group $R^{21}$ may be a protected form of a hydrophilic substituent of the type described above in connection with the groups $R^9$ and $R^{10}$; in particular it may be a protected form of a group —C(O)—$R^{14}$ as defined above. Thus in an embodiment, $R^{21}$ is selected from hydrophilic substituents, in which the or each reactive terminal group is protected by an independently selected protecting group $P^2$.

A group $R^{21}$ may incorporate one or more polymerisable functional groups, as discussed above in connection with the groups $R^9$ and $R^{10}$ in compounds of formula (I) and (Ia).

A protecting group $P^1$ or $P^2$ may for example be selected from C1 to C4 alkyl (in particular methyl or t-butyl), alkoxyl (for example C1 to C4 or C1 to C3 or C1 to C2 alkoxyl, in particular methoxyl), and esters —$CO_2R^{11}$, where $R^{11}$ is as defined above. The skilled person will be readily able to select suitable protecting groups, depending on the natures of the reactive groups to be protected and the conditions under which they need protection. For example, an acid group —$CO_2H$ may be protected in the form of an ester —$CO_2R^{11}$, where $R^{11}$ may be as defined above and is in particular selected from C1 to C4 alkyl (for example t-butyl). An amine group —$N(R^{12})_2$ may be protected in the form of a carbamate, in which any $R^{12}$ groups which are hydrogen are replaced by —$CO_2R^{11}$.

In an embodiment, at least one $P^1$ group is an alkoxyl group, for example a C1 to C4 or C1 to C3 or C1 to C2 alkoxyl group, in particular methoxyl. In an embodiment, at least one $P^2$ group is an alkyl group, for example a C1 to C4 alkyl group, in particular methyl or t-butyl, more particularly t-butyl. In an embodiment, $P^2$ is such as to form an ester —$CO_2R^{11}$, where $R^{11}$ may be as defined above and is in particular selected from C1 to C4 alkyl, for example t-butyl.

Where the group $R^{21}$ comprises more than one potentially reactive functional group (for example more than one carboxylate group), each such group should be protected by a suitable protecting group $P^2$.

The group $R^{21}$ may incorporate a polymerisable functional group, of the type discussed above in connection with the first to the third aspects of the invention. It may for instance comprise a group —NH—C(O)—CH=$CH_2$. Such a group may be introduced onto the commercially available amine-substituted isophthalic acid (ie a version of compound (III) in which $R^{19}$ and $R^{20}$ are both —OH and $R^{21}$ is —$NH_2$) by treatment with acryloyl chloride $CH_2$=CH—C(O)—Cl, prior to reacting the resulting intermediate with a compound of formula (II).

In a first specific embodiment of the eleventh aspect of the invention, the method is used to prepare a compound of formula (I) or (Ia) which is symmetrical as regards its two anthracene moieties. In this embodiment, both $R^{19}$ and $R^{20}$ are independently selected leaving groups L. The first step of the method can then result in the formation of a precursor compound which, on removal of the protecting group(s) $P^2$, can be converted to the compound of formula (I) or (Ia). The compounds (II) and (III) thus react with one another in a molar ratio of 1:1. Suitably, the leaving groups $R^{19}$ and $R^{20}$ are the same.

In a second specific embodiment of the eleventh aspect of the invention, the method is used to prepare a compound of formula (I) or (Ia) which is asymmetrical as regards its two anthracene moieties. In this embodiment, $R^{20}$ is a protecting group $P^1$. The first step of the method then results in the formation of an intermediate compound (IV):

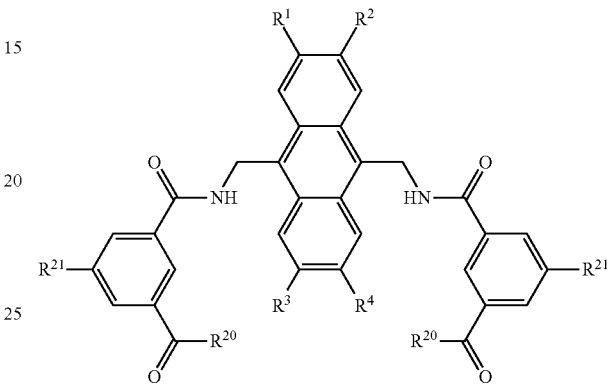

(IV)

in which the groups $R^1$ to $R^4$ and $R^{21}$ are as defined above and $R^{20}$ is a protecting group $P^1$ as defined above. The first step is then followed by (a) replacement of the protecting groups $P^1$ (ie $R^{20}$) with leaving groups L, to form a compound of formula (IVa) (which is a compound of formula (IV) in which $R^{20}$ is a leaving group L as defined above); and (b) reaction of the compound (IVa) with a further compound of formula (II) as defined above, this compound (II) potentially being different from the compound (II) used in the first step (for example, it may carry, instead of the substituents $R^1$ to $R^4$, corresponding substituents $R^5$ to $R^8$ as defined above in connection with the compound of formula (I)).

In this second embodiment, the protecting group(s) $P^2$ will need to remain in place during the removal of the protecting group $P^1$ and the subsequent cyclisation reaction with the further compound of formula (II). Thus, $P^1$ and $P^2$ should be different protecting groups.

Suitable leaving groups L, with which to replace the protecting groups $P^1$, include those described above in connection with the group $R^{19}$. The method of this second specific embodiment may be advantageous in allowing the preparation of a single product rather than potentially a mixture of isomers with associated separation issues.

An asymmetric compound (I) or (Ia) may also be preparable by using, in the first step of the invented method, a compound of formula (III) in which both $R^{19}$ and $R^{20}$ are leaving groups L, so long as the compound (III) is present in moderate excess, for instance at a molar ratio of compound (II) to compound (III) of approximately 1:2 to 1:4, such as about 1:3. This results in an intermediate compound of formula (IVa), as defined above, in which $R^{20}$ is a leaving group L. The compound (IVa) can then be reacted with a further, potentially different, compound of formula (II).

In any embodiment of the eleventh aspect of the invention, a subsequent step may comprise removal of the protecting group(s) $P^2$ from the groups $R^{21}$, to leave the desired groups $R^9$ and $R^{10}$ in the final compound of formula (I) or (Ia).

It can be seen that the invention makes possible the preparation of a compound (I) or (Ia) in relatively few steps, and from readily available starting materials. The compound of formula (II) may for instance be prepared by reacting vinylene carbonate with anthracene, the anthracene being optionally substituted with one or more of the groups $R^1$ to $R^8$ as defined above, followed by hydrolysis and oxidative cleavage to form a bis-dialdehyde derivative of the anthracene moiety [see Yamada et al, *Chem Eur J,* 11: 6212-6220 (2005), and Katsuta et al, *Org Lett,* 13: 1454-1457 (2011)]. This could then be subjected to reductive amination in order to yield the compound (II). Bis-(aminomethyl)anthracene itself is also commercially available.

The compound of formula (III) may be prepared from isophthalic acid, or more typically from a suitable 5-substituted isophthalic acid such as mesitoic acid, by standard synthetic chemistry techniques which would not present an undue burden to the person skilled in the art. Key to the overall synthesis is to differentiate the three reactive carbonyl groups of the isophthaloyl moiety, with protecting and/or leaving groups as appropriate, in order to ensure the correct sequence of reactions.

In an embodiment of the eleventh aspect of the invention, the method comprises preparing the compound (II) and/or (III) prior to their reaction with one another, and/or preparing a further compound (II) prior to its reaction with an intermediate compound (IVa). In particular, the preparation of a compound (II) may involve selecting and introducing the substituents $R^1$ to $R^4$ or $R^5$ to $R^8$ so as to "tune" the spectroscopic response of the final product of formula (I) or (Ia). The preparation of a compound (III) may involve selecting and introducing the substituent $R^{21}$ so as to tune the solubility and/or other functional attributes of the eventual product.

The method of the eleventh aspect of the invention can make it possible to prepare both symmetric and asymmetric versions of compound (I) or (Ia), depending on the properties required of it, in particular as regards its response to electromagnetic radiation and hence its detectability.

The reaction between the compound (II) and the compound (III), and if applicable the subsequent reaction between the intermediate compound (IVa) and the further compound (II), may be carried out under any conditions suitable to allow replacement of the relevant leaving group(s) L by the nitrogen atoms of the —$NH_2$ groups in the compound (II), and thus formation of the amide linking groups in the reaction product. The reaction may be carried out at any suitable temperature, for example room temperature. It may be carried out in a non-hydroxylic solvent such as THF. A catalyst such as a tertiary amine, for example N,N-di-isopropylethylamine (DIPEA) or dimethylaminopyridine (DMAP), may be used.

The removal and replacement of leaving groups and protecting groups may be performed using standard chemical synthetic techniques, as are well known to the person skilled in the art.

By way of example, the reaction between the compound (II) and the compound (III) may be carried out in the presence of a suitable base such as DIPEA. For cyclisation steps, for instance when reacting compound (II) with compound (III) to generate (I) or (Ia) directly, or when reacting the intermediate (IVa) with a further compound (II), it may be preferable to carry out the reaction at a high dilution.

A twelfth aspect of the invention provides a compound of formula (V):

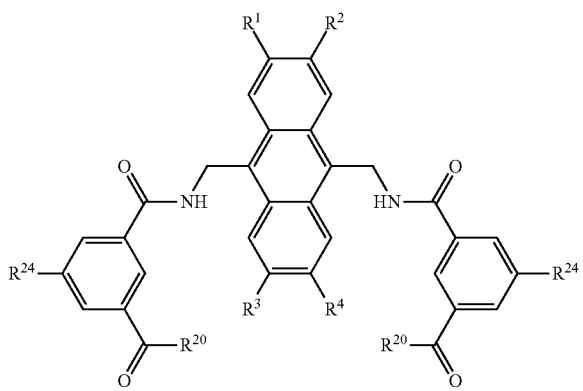

(IV)

wherein $R^1$ to $R^4$ and $R^{20}$ are as defined above in connection with the formulae (II) and (III); each $R^{24}$ is independently selected from groups $R^9$ as defined above, and groups $R^9$ as defined above in which the or each reactive terminal group is protected by a protecting group $P^3$; and each $P^3$ is independently selected from protecting groups which are capable of preventing the substituent to which they are joined from reacting with an —$NH_2$ group in a compound of formula (II), in step (b) of a synthetic method in accordance with the eleventh aspect of the invention.

In an embodiment, each $R^{24}$ is independently selected from groups $R^9$ in which the or each reactive terminal group is protected by a protecting group $P^3$. In an embodiment, each $R^{24}$ is independently selected from hydrophilic substituents, and hydrophilic substituents in which the or each reactive terminal group is protected by a protecting group $P^3$. In an embodiment, each $R^{24}$ is independently selected from hydrophilic substituents in which the or each reactive terminal group is protected by a protecting group $P^3$. Suitably the two groups $R^{24}$ are the same.

A protecting group $P^3$ may be as defined above in connection with the group $P^2$.

In an embodiment, each $R^{20}$ is independently selected from leaving groups L. In an embodiment, each $R^{20}$ is independently selected from protecting groups $P^1$. Suitably the two groups $R^{20}$ are the same.

A compound (V) according to the twelfth aspect of the invention (which also embraces the compounds (IV) and (IVa)) may be formed as an intermediate in a method according to the eleventh aspect of the invention. Such an intermediate may in particular be of use in preparing an asymmetric version of the compound (I) or (Ia), in which the two anthracene moieties are not the same.

According to a thirteenth aspect of the invention, there is provided the use of a compound according to the first or second aspect, a polymer according to the third aspect, a composition according to the fourth aspect, a device according to the fifth aspect and/or a detection system according to the sixth aspect, for the detection of a target saccharide (in particular glucose) in an aqueous environment such as blood or a blood-derived product.

According to further aspects, the present invention can provide a compound of formula (I) or (Ia) as defined above; a method for its synthesis; a polymer incorporating such a compound; a composition comprising such a compound or polymer; a device which carries such a compound or polymer or composition; a detection system and method for detecting a target saccharide in an aqueous environment; a supply system for supplying an active substance to an aqueous environment; a method of treatment or diagnosis, or part thereof, or a compound, polymer, composition, device or system for use in such a method; a compound of formula (V) as defined above; and the use of such compounds, polymers, compositions, devices and systems for the detection of a target saccharide in an aqueous environment, which compounds, polymers, compositions, devices, systems, methods and uses may be substantially as herein described with reference to the accompanying illustrative drawings.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, for example for the concentration of a target compound or the binding affinity between two compounds, then a range of values defined by a combination of any of the upper limits with any of the lower limits may also be implied.

In this specification, references to properties such as solubilities or binding affinities are—unless stated otherwise—to properties measured under ambient conditions, ie at atmospheric pressure and at a temperature of from 16 to 22 or 25° C., or from 18 to 22 or 25° C., for example about 20° C. or about 25° C.

The present invention will now be further described with reference to the following non-limiting examples, and the accompanying illustrative drawings, of which:

FIG. 1A shows a synthetic lectin 2, as described above, which has been previously reported for use in the detection of glucose; FIG. 1B shows a compound 3, also for use in the detection of glucose, in accordance with the present invention; FIG. 1C shows the compound 3 complexed with glucose;

FIGS. 2A, 2B, and 2C illustrate, schematically, aspects of the design and synthesis of the compound 3 and of its interactions with glucose molecules;

Figure 9:
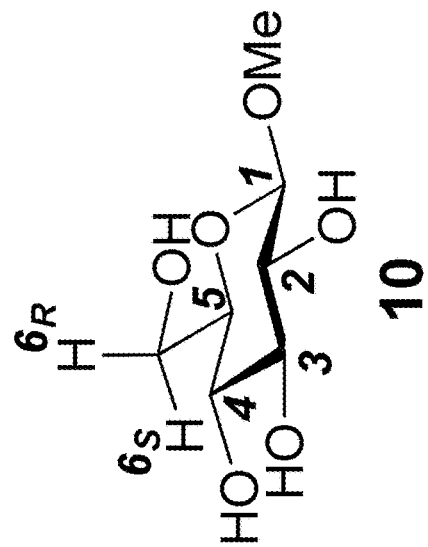
Figure 9:
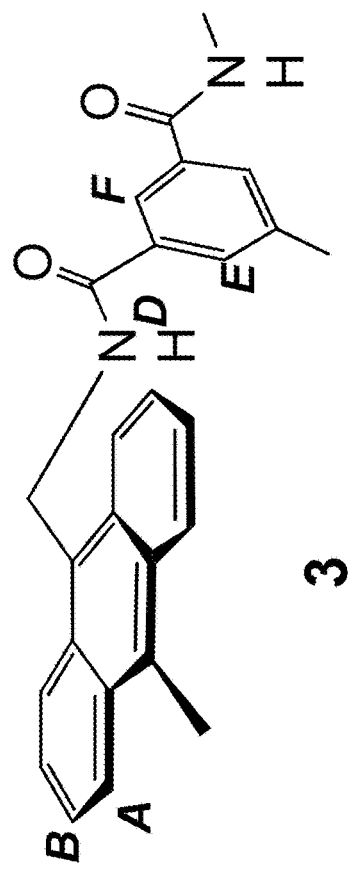
Figure 10A:
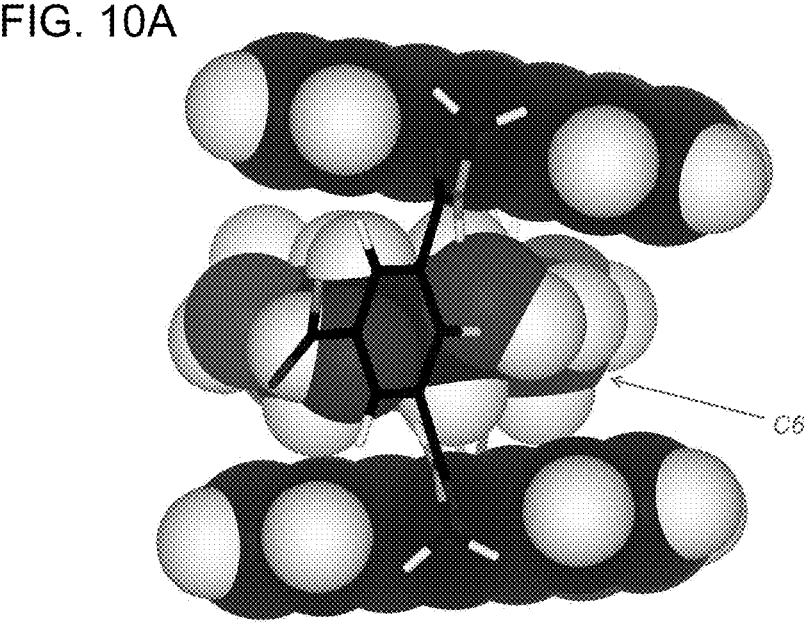
Figure 10B:
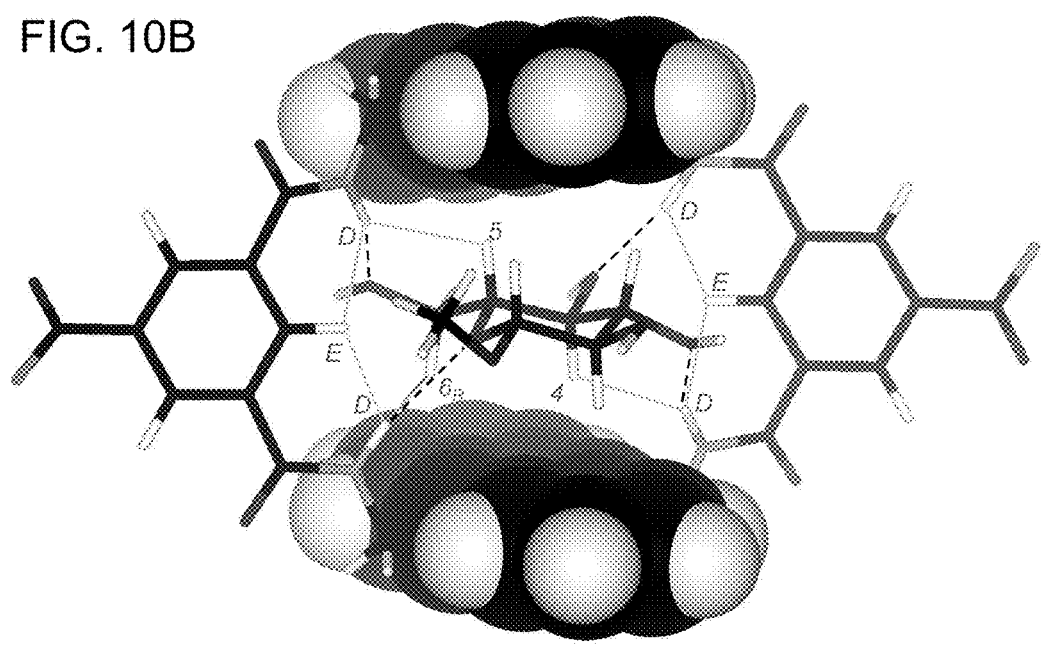
Figure 11:
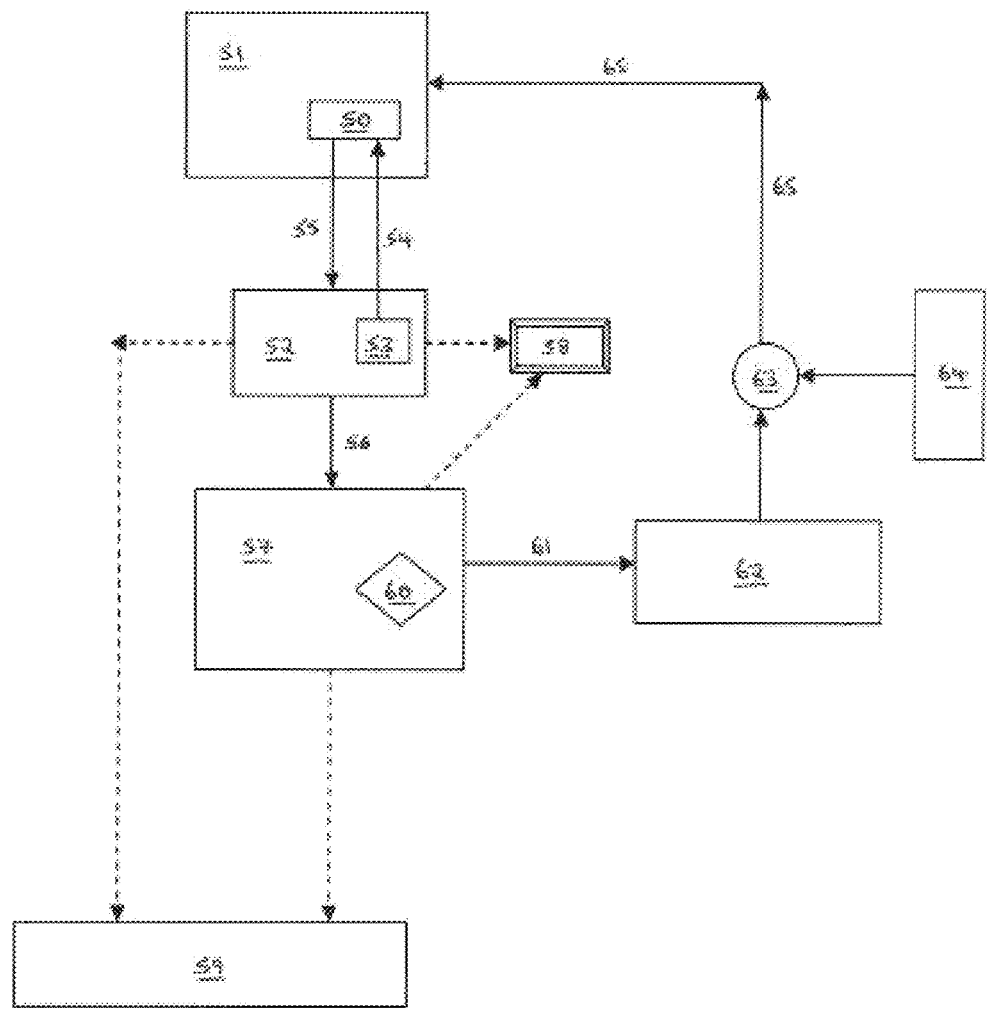
Figure 12A:
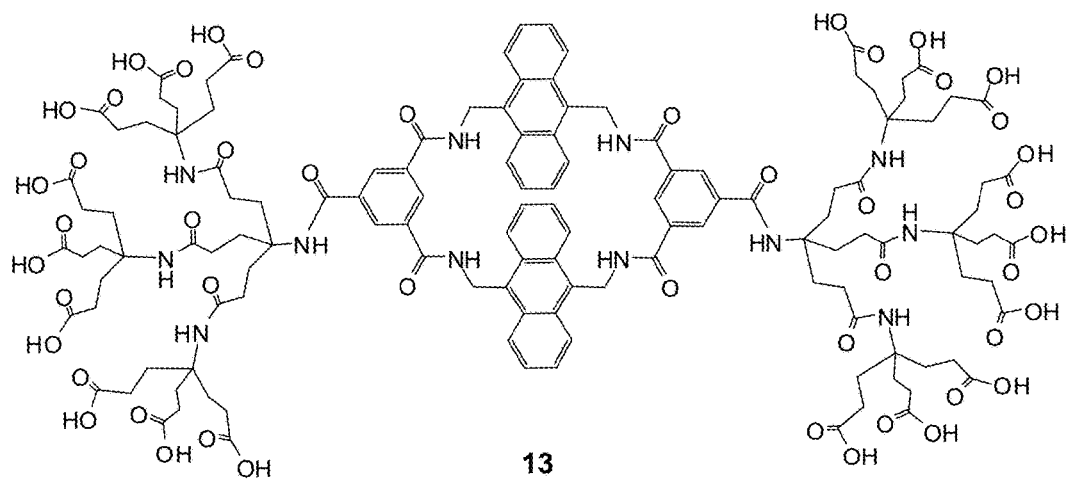
Figure 12B:
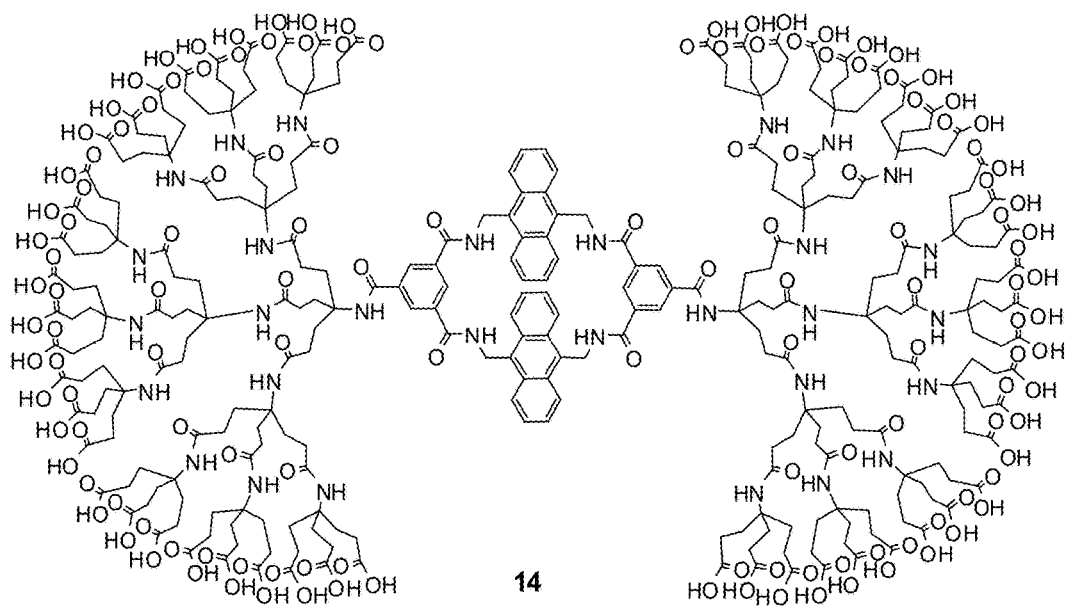
Figure 13A:
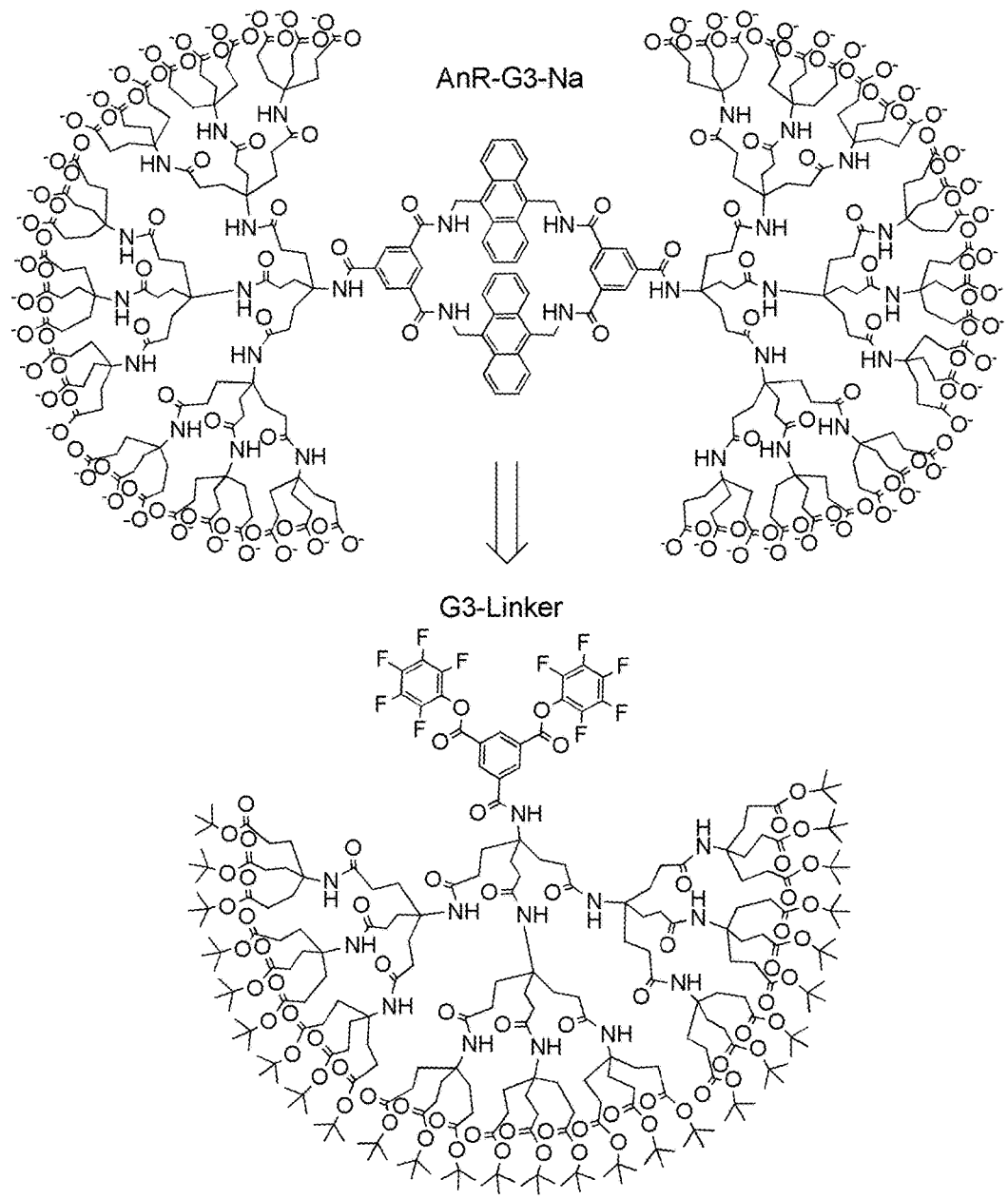
Figure 13B:
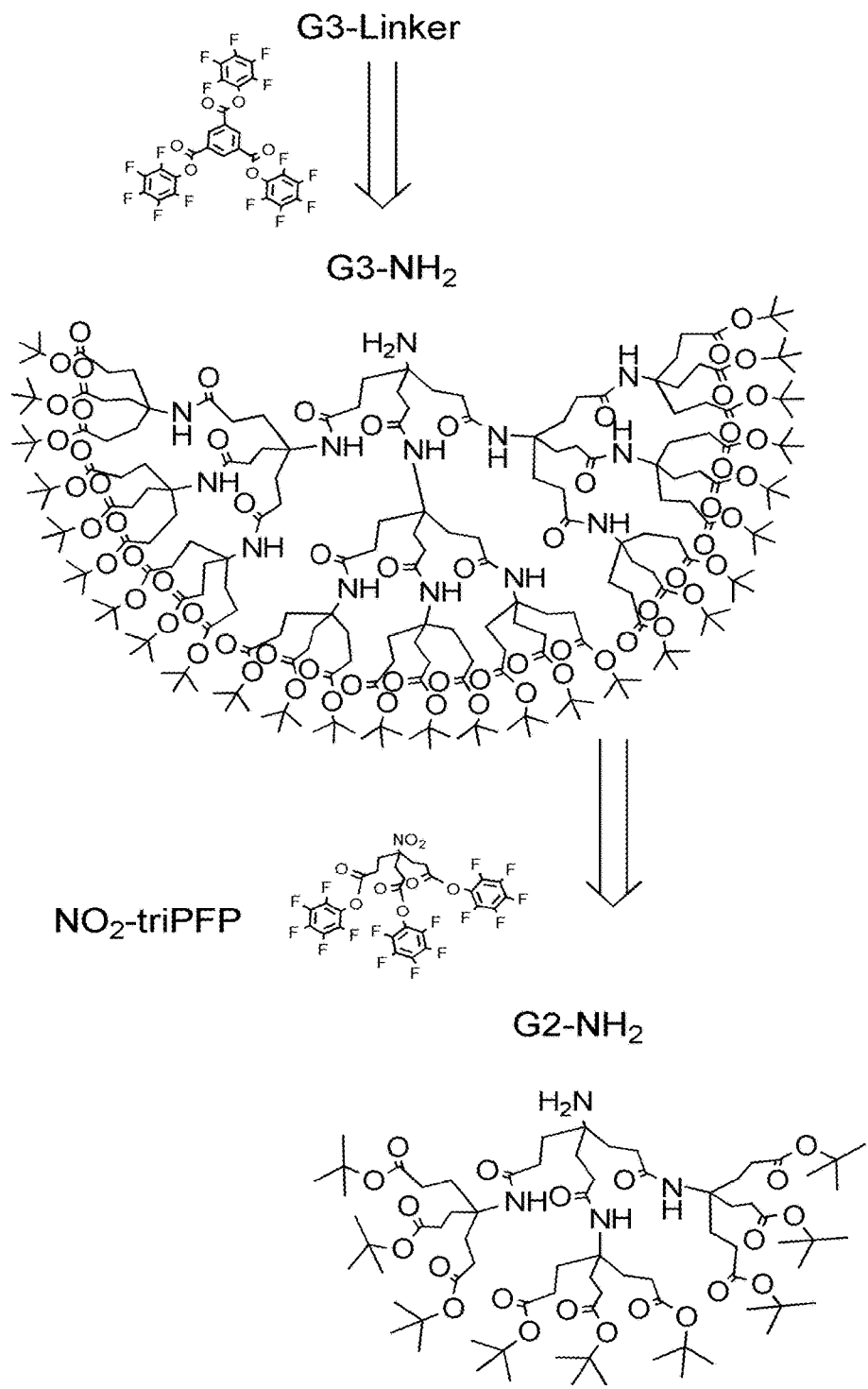
Figure 13C:
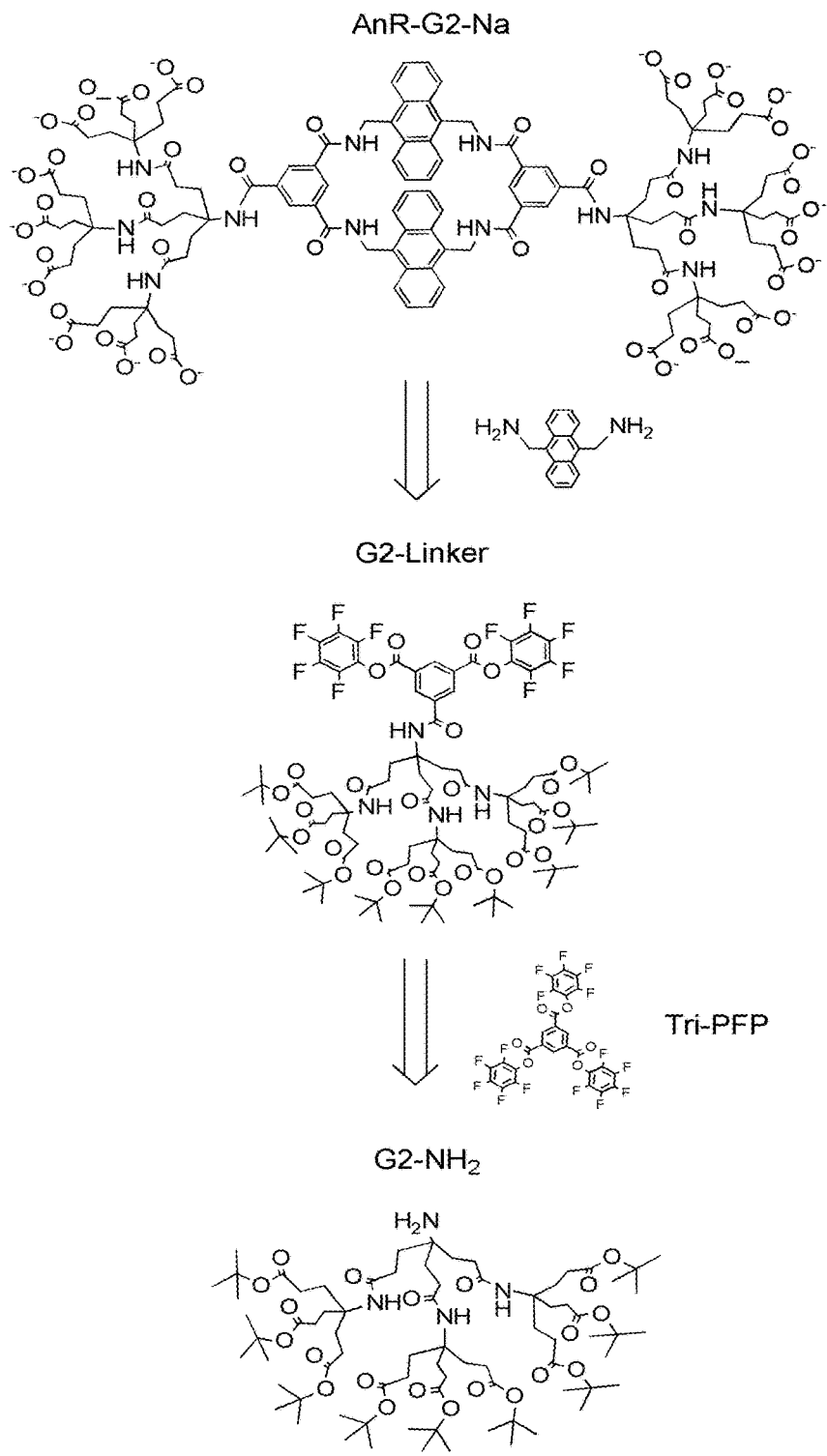
Figure 14A:
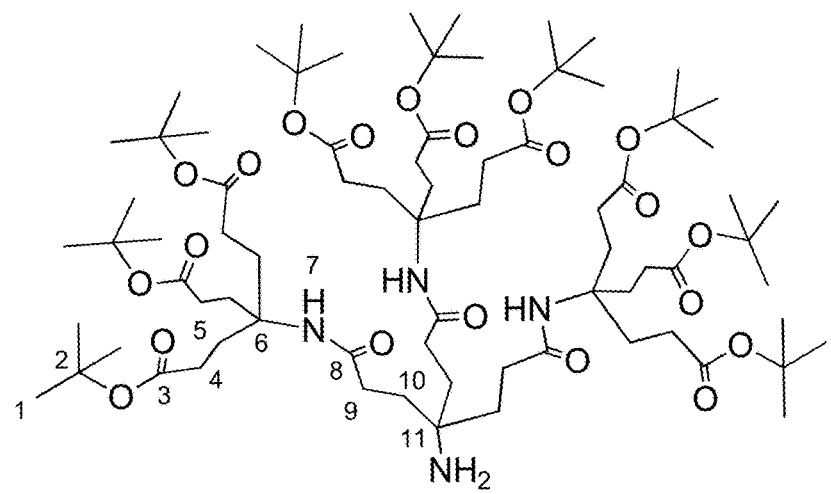
Figure 14B:
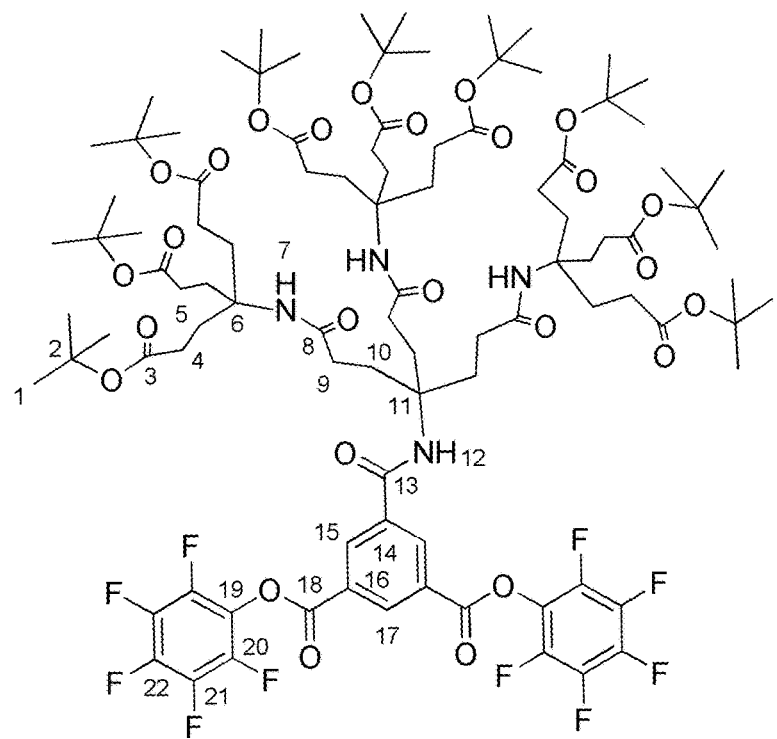
Figure 14C:
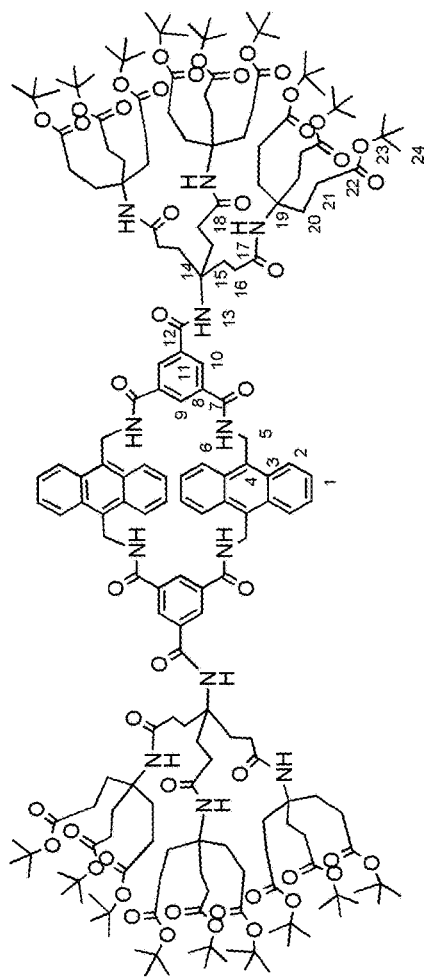
Figure 14D:
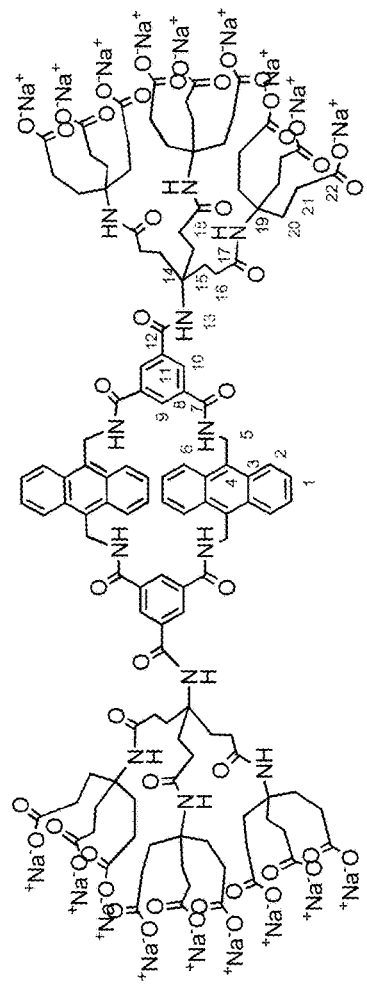
Figure 14E:
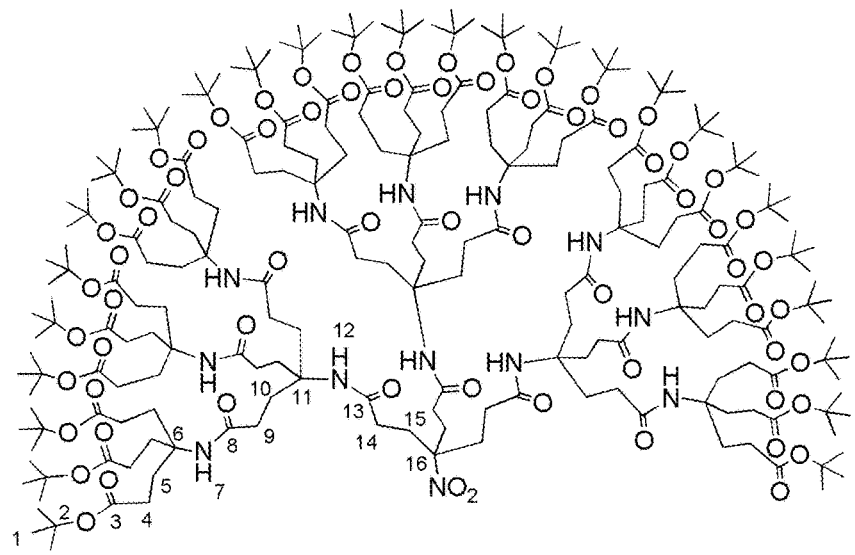
Figure 14F:
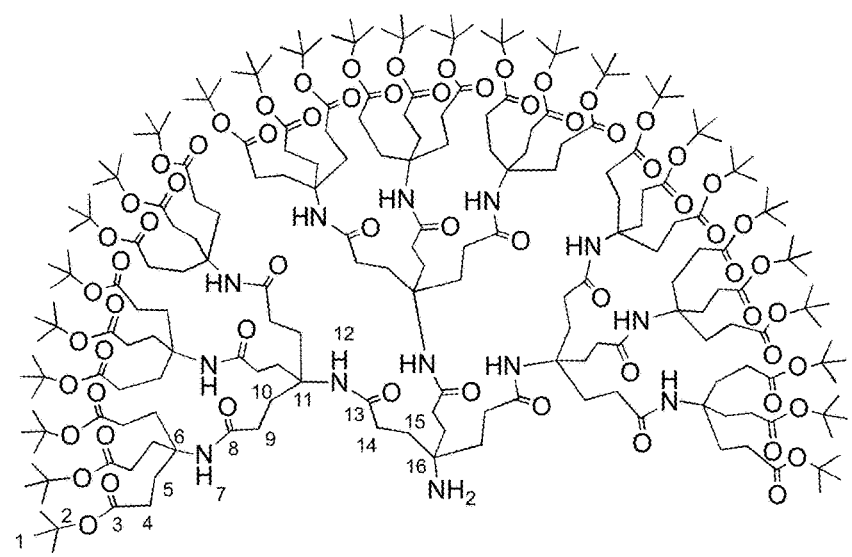
Figure 14G:
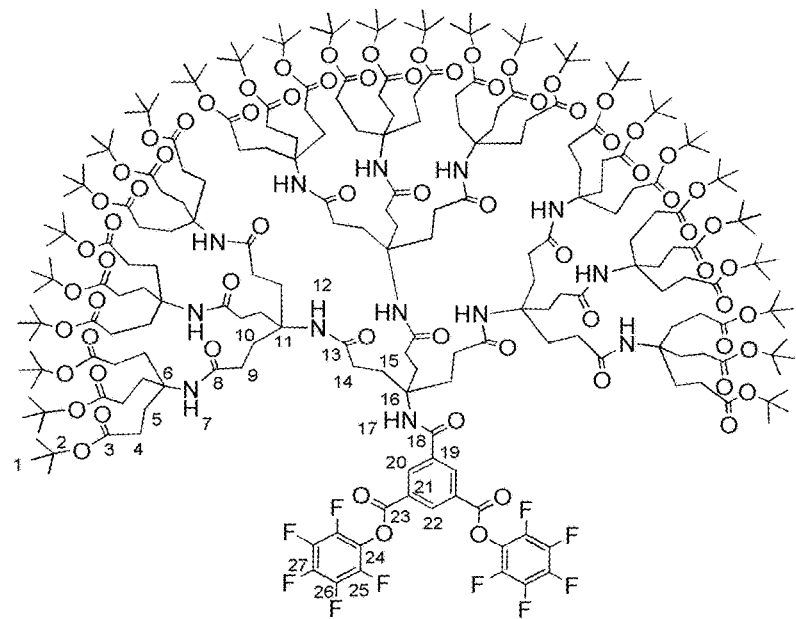
Figure 14H:
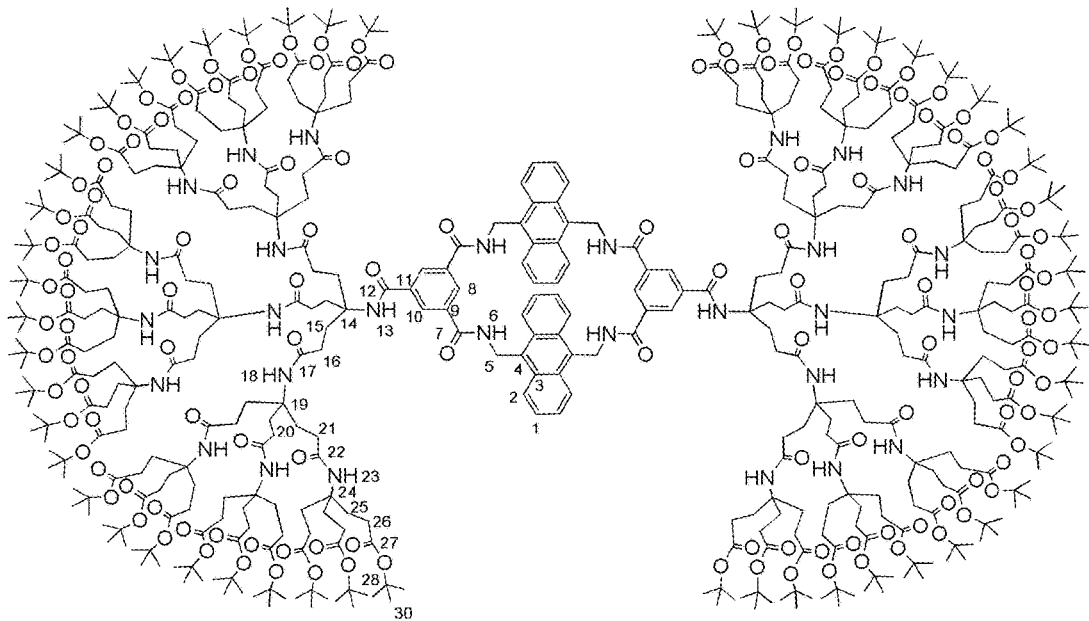
Figure 16:
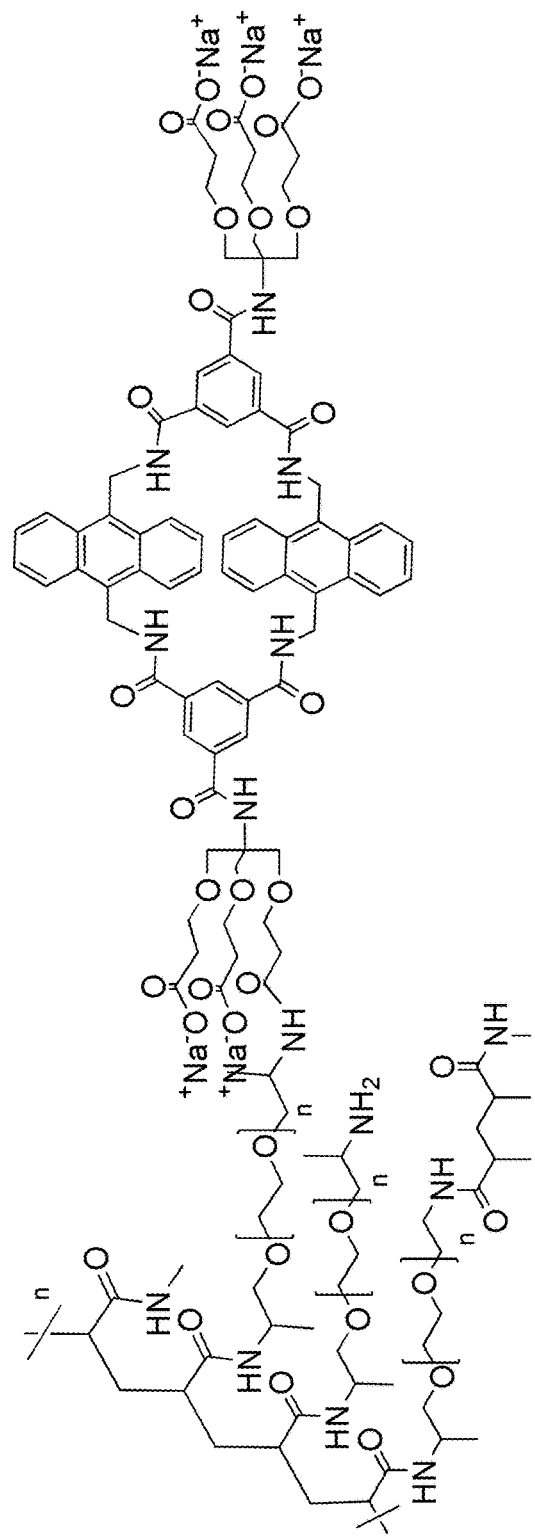
Figure 17A:
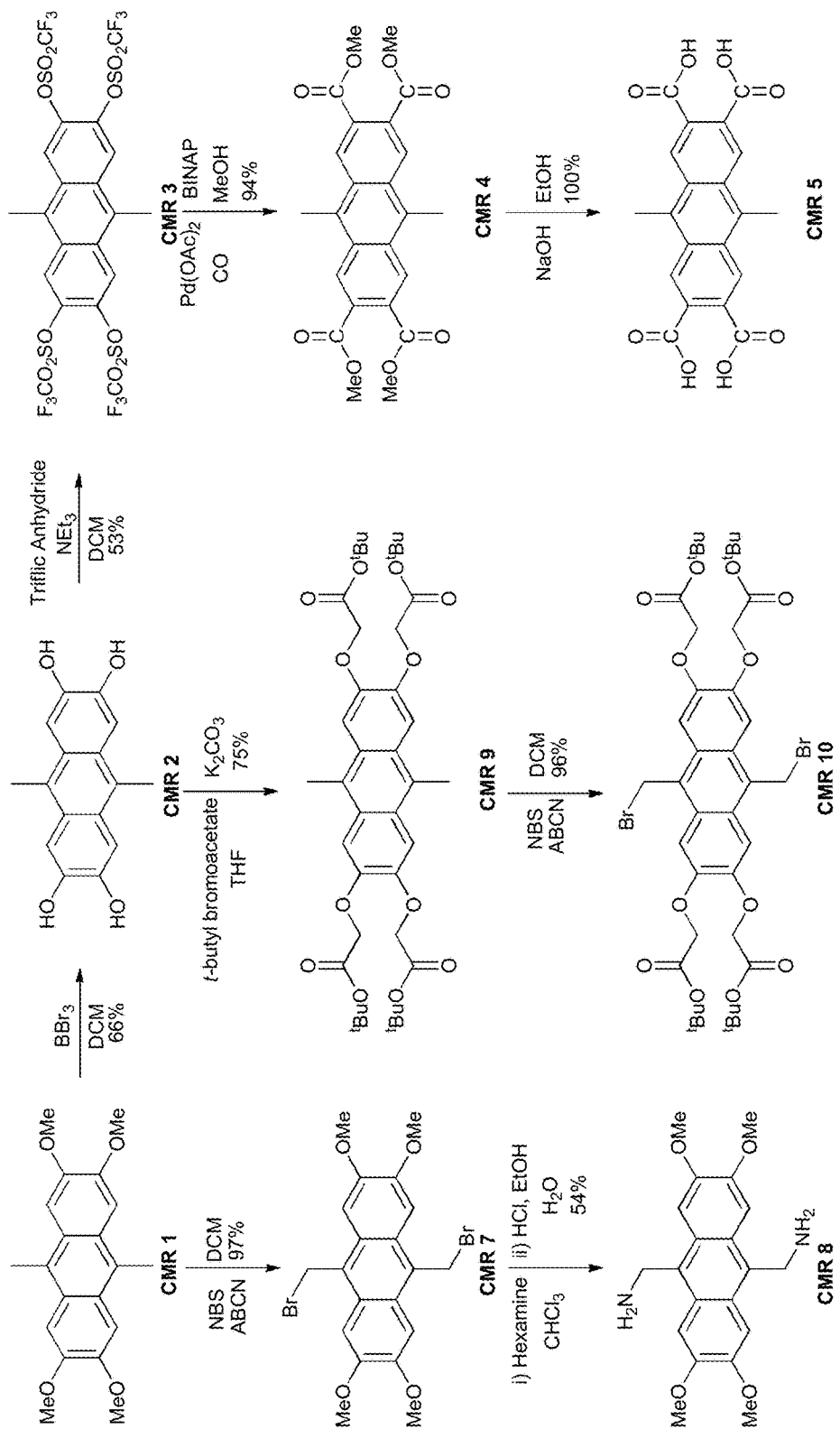
Figure 17B:
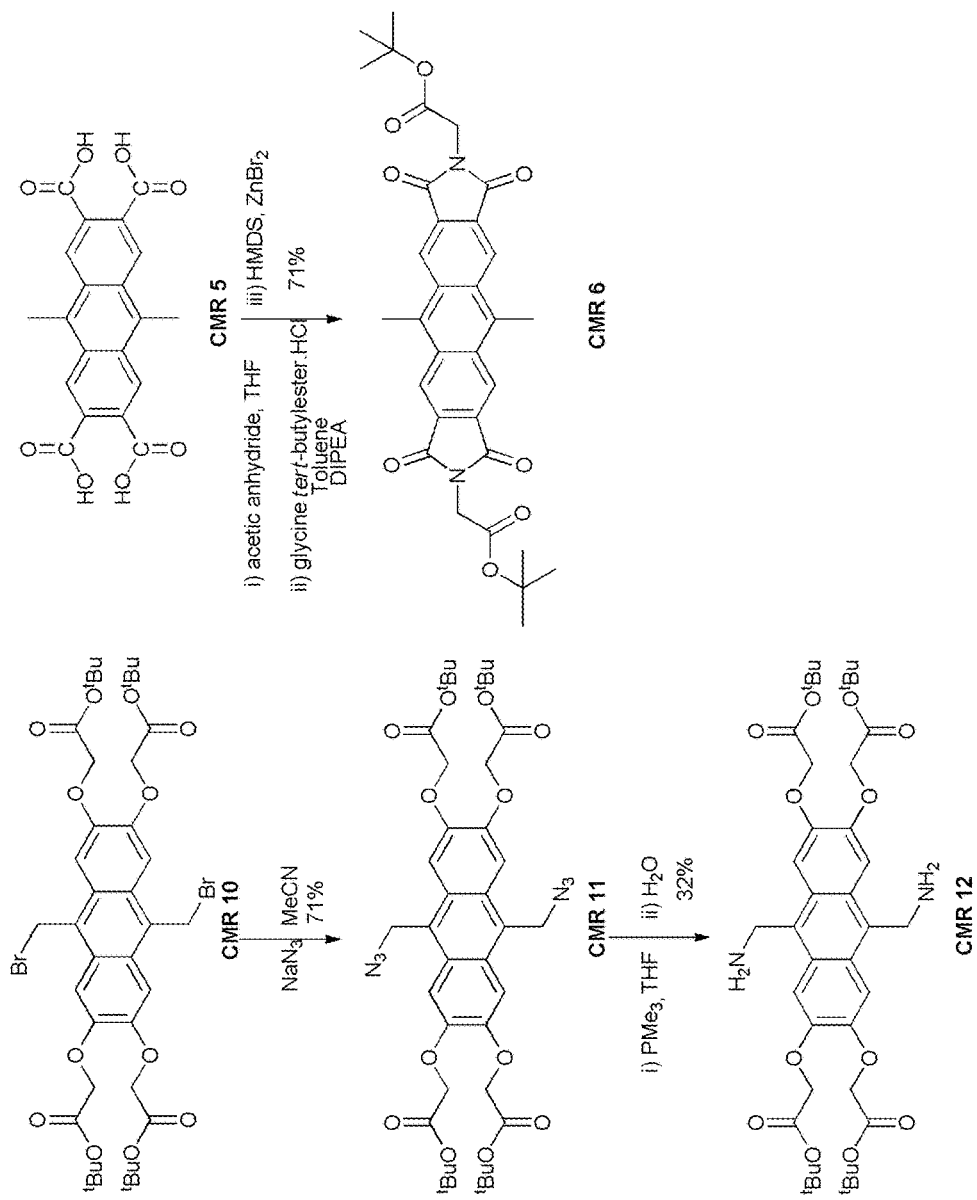
Figure 18:
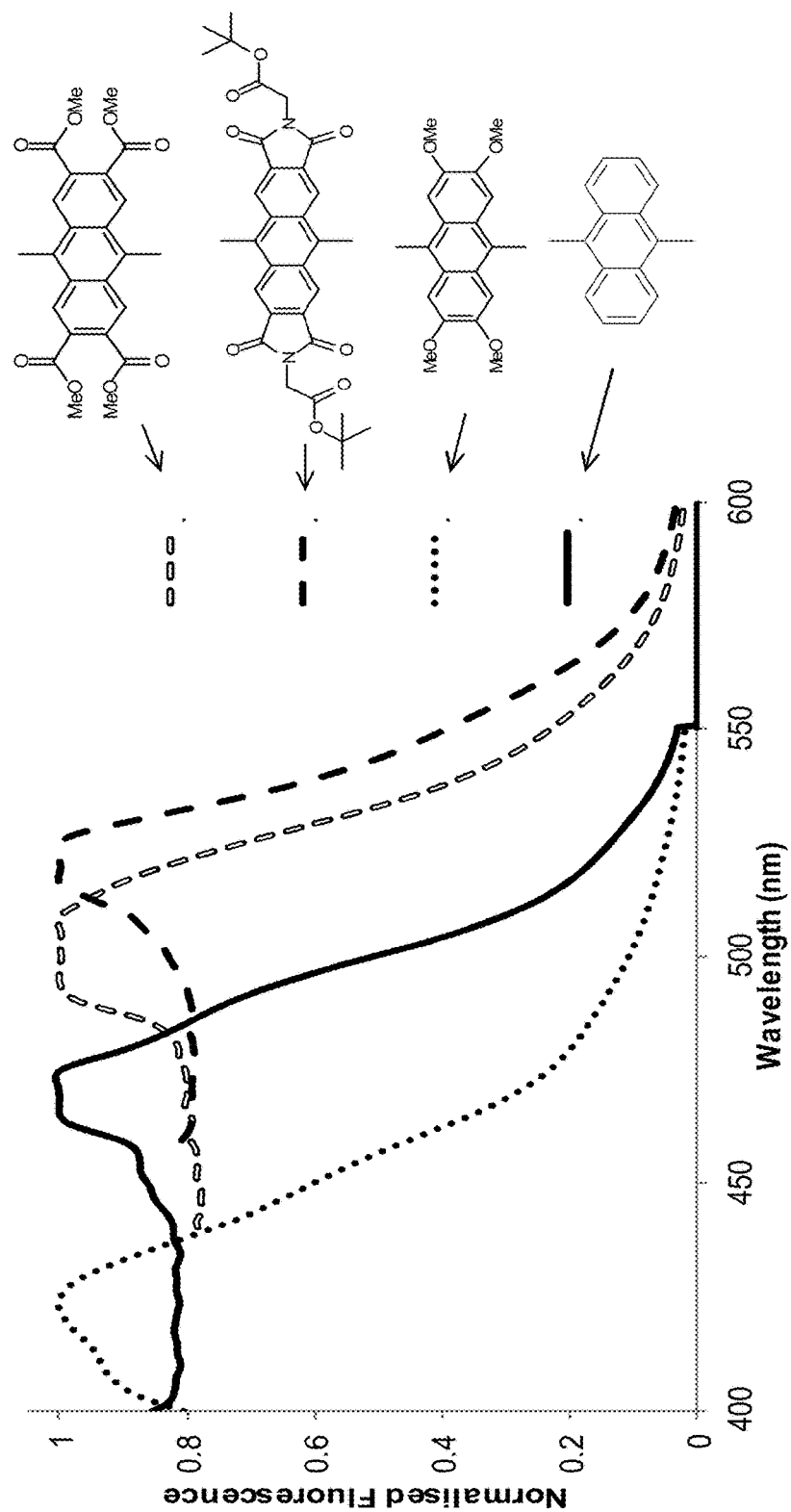

FIGS. 8A, 8B, 8C, and 8D show data from binding studies on compound 3 and glucose, in the form of partial $^1$H NMR spectra, binding curves, fluorescence titration data and ITC (isothermal titration microcalorimetry) data, as referred to in Examples 3 to 6 below;

FIG. 9 shows the labelling system used for NMR binding and structural studies on the compound 3 and a methyl-β-D-glucose molecule 10;

FIGS. 10A and 10B show NMR-based structures for a complex formed between the compound 3 and methyl-β-D-glucoside;

FIG. 11 illustrates schematically a detection device, and a detection and supply system, according to the invention;

FIGS. 12A and 12B show further compounds 13 and 14 according to the invention;

FIGS. 13A, 13B and 13C show retrosynthetic schemes for the synthesis of compounds 13 and 14, as described in Examples 9 and 11 respectively below;

FIGS. 14A-14I show the structural formulae for compounds prepared in Examples 9 and 11;

FIGS. 15A-15D show data from studies on compound 13, in the form of fluorescence emissions spectra, partial $^1$H NMR spectra and binding selectivity data, as referred to in Example 10 below;

FIG. 16 shows the structural formula for the compound 3 bound to a poly[acryloyl-bis(aminopropyl)polyethylene glycol], as described in Example 12 below;

FIGS. 17A and 17B show schematically the methods by which substituted anthracene precursor compounds were synthesised in Example 13 below, in order to test the effects of their substituents on their emissions spectra; and FIG. 18 shows fluorescence spectra for four anthracene precursor molecules, as tested in Examples 13A, 13B and 13C.

EXAMPLE 1—DESIGN & SYNTHESIS OF COMPOUND 3

Figure 1A:
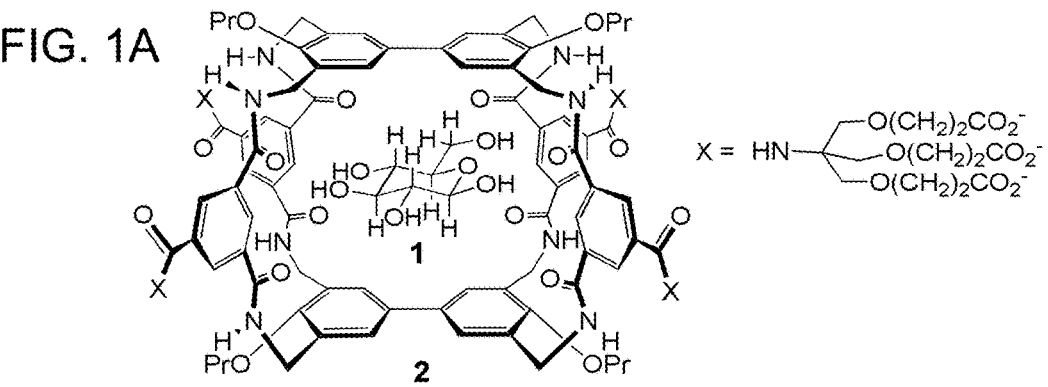
Figure 1B:
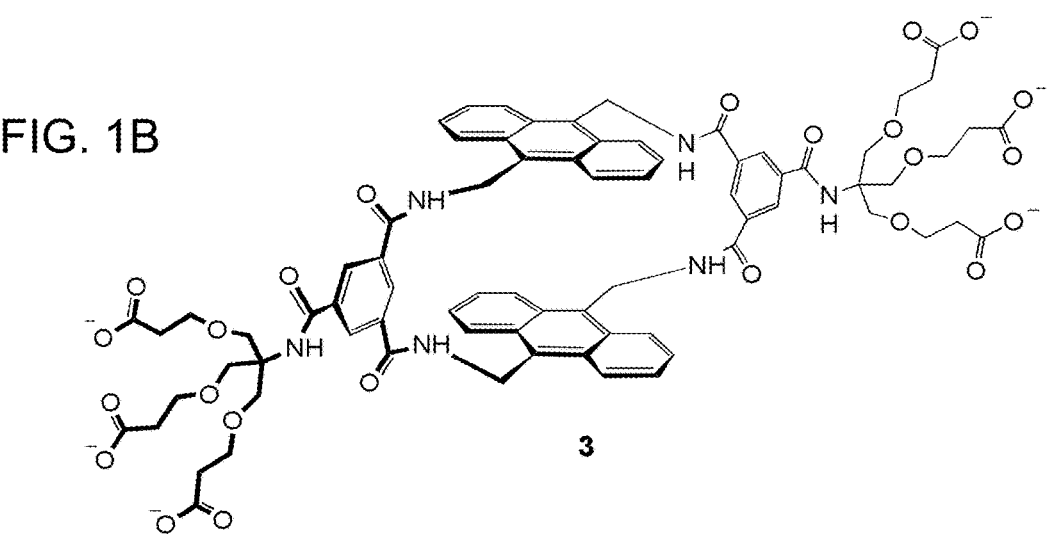
Figure 1C:
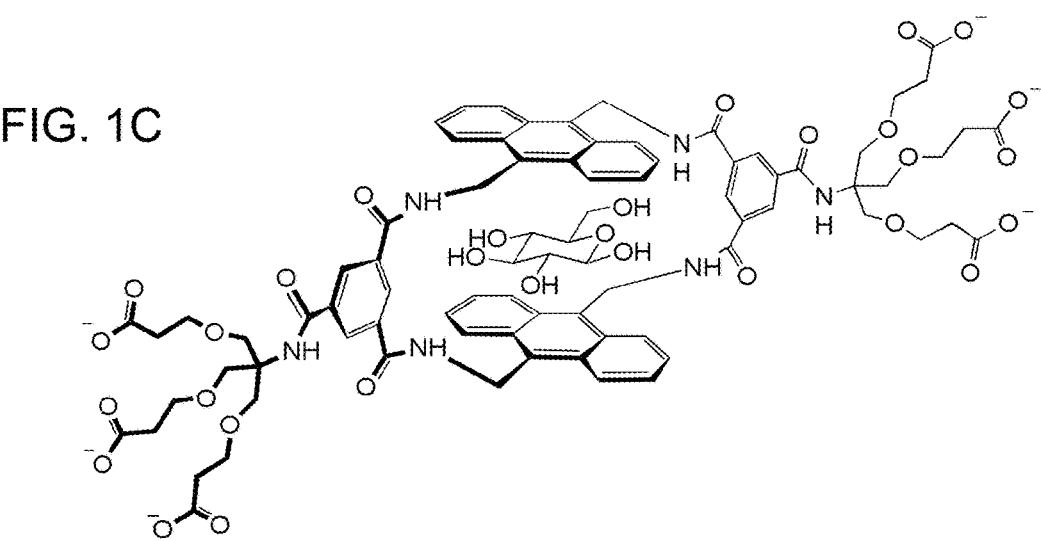

The compound 3, shown in FIG. 1B, is a compound according to the first aspect of the invention, designed as a synthetic lectin analogue for the purpose of detecting glucose in human blood. The compound 3 has been shown to be capable of associating with a molecule of glucose (ie D-glucose), which is able to occupy the cavity defined by the two aromatic anthracene moieties and the two bridging isophthaloyl groups—see FIG. 1C. Compound 3 can be seen to have a much simpler structure than that of the previously reported synthetic lectin 2 which is shown in FIG. 1A and described above.

Underlying the present invention is the unexpected discovery that condensed aromatic units can play a useful role in the design of improved synthetic lectins. Contact between aromatic surfaces and carbohydrate CH groups is often observed in lectin-saccharide complexes, and it is widely thought that CH-π interactions, allied to hydrophobic effects, can make important contributions to binding, as indeed in the compound 2 of FIG. 1A. In previously prepared synthetic lectins, for example compound 2, the aromatic surfaces have been provided by oligophenyl units. However, though helpful synthetically, the biphenyl bond tends to twist due to steric interference between ortho hydrogens, and this can disturb the interactions between rigidly positioned axial CH groups and the aromatic surfaces. In contrast, a condensed aromatic unit can make ideal contact with an array of axial CH groups. Moreover, a carbohydrate molecule can slide across the surface of the aromatic unit without significant loss of binding energy, so that (a) other interactions can be maximised and (b) some freedom of movement can be retained within the complex (hence less entropy loss on binding). Such effects are illustrated schematically in FIGS. 2A and 2B, which show the interactions of both biphenyl (FIG. 2A) and condensed aromatic (FIG. 2B) units with a β-D-glucose molecule.

The use of condensed aromatic moieties in the compounds of the present invention can provide additional advantages in the context of the detection of saccharides. These moieties tend to be strongly absorbent of electromagnetic radiation and also fluorescent, with their emissions being modulated on association with a target saccharide such as glucose.

It has been found that a compound such as 3 can be prepared in just two steps: cyclisation of suitably protected forms of the constituent bis-anthracenyl and isophthaloyl moieties, followed by deprotection of the pendant solubilising groups (in this case, —NHC(CH$_2$OCH$_2$CH$_2$CO$_2^-$)$_3$ groups, which can be protected during the cyclisation step with, for example, t-butyl groups). Such a reaction is shown schematically in FIG. 2C, according to which the monocycle 3 is prepared by reacting the diamine 4 (bis-(aminomethyl) anthracene) with the isophthaloyl spacer component 5. The PFP groups function as leaving groups in 5, whilst the —C(O)—Y group is a protected form of a hydrophilic, water-solubilising substituent.

The FIG. 2C reaction is a method according to the eleventh aspect of the invention.

Figure 3:
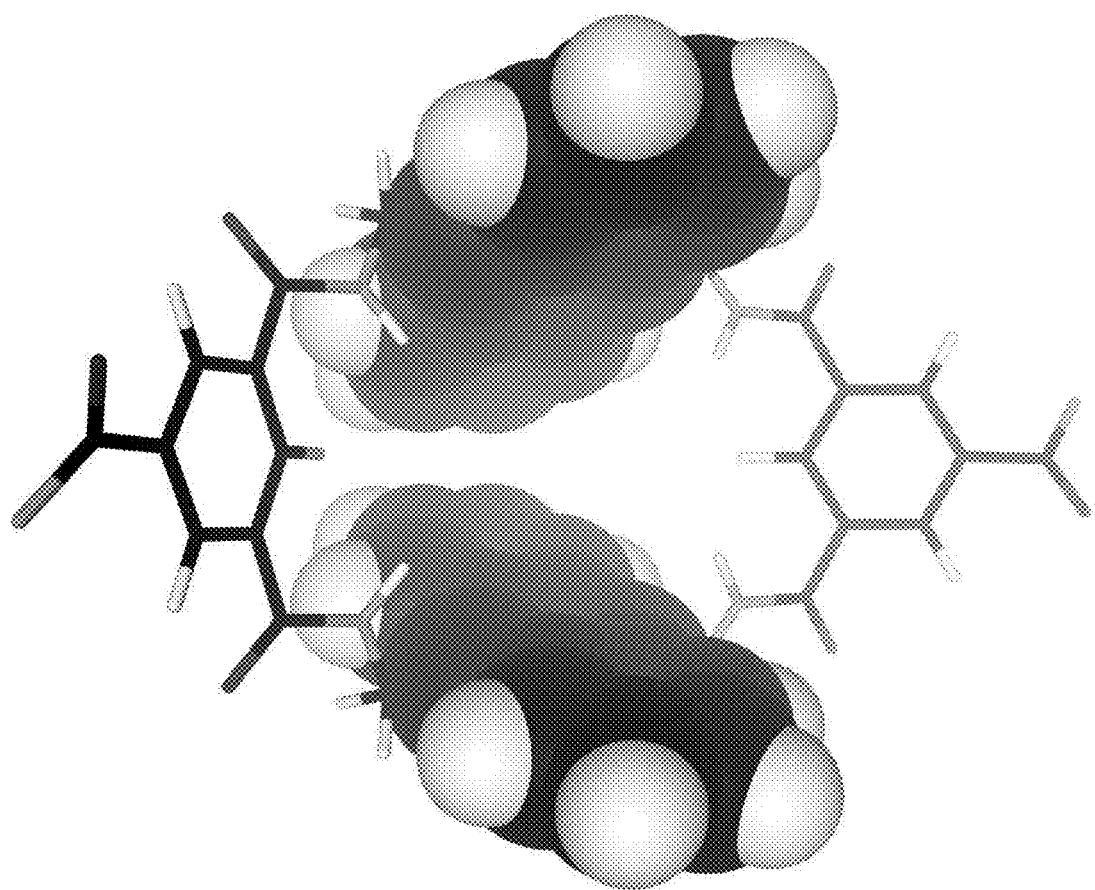
FIG. 3 illustrates the ground state conformation of a molecule of 3 as predicted by Monte Carlo molecular mechanics calculations.

Monte Carlo molecular mechanics calculations suggested that the molecule 3 could adopt a range of conformations with different angles between its aromatic surfaces, but that all low-energy structures would feature a cleft or cavity (as seen in FIG. 3; solubilising side chains removed for clarity; anthracene units shown in space-filling mode). It was not clear, however, that this simple and rather flexible architecture would favour any particular saccharide, or indeed that it would show any notable carbohydrate-binding properties. However the enclosed, amphiphilic nature of the cavity did seem generally suitable for carbohydrate recognition, although the tilted arrangement of the anthracene moieties might not be ideal for certain saccharide molecules.

Compound 3 was prepared in ~23% yield using the route shown in FIG. 2C. The diamine component 4 is available commercially, but can also conveniently be synthesised by bis-bromomethylation of anthracene followed by treatment with hexamethylenetetramine [Gunnlaugsson et al, *Org Lett* 4: 2449-2452 (2002)]. Diester 5 was prepared via a 3-step procedure which involved treatment of tris(hydroxymethyl) aminomethane with t-butyl acrylate; reaction of the resulting amine with 1,3,5-benzenetricarbonyl trichloride (followed by hydrolysis of unreacted acid chloride groups); and conversion of carboxylic acid groups to PFP esters using N,N'-dicyclohexylcarbodiimide (DCC).

Figure 4:
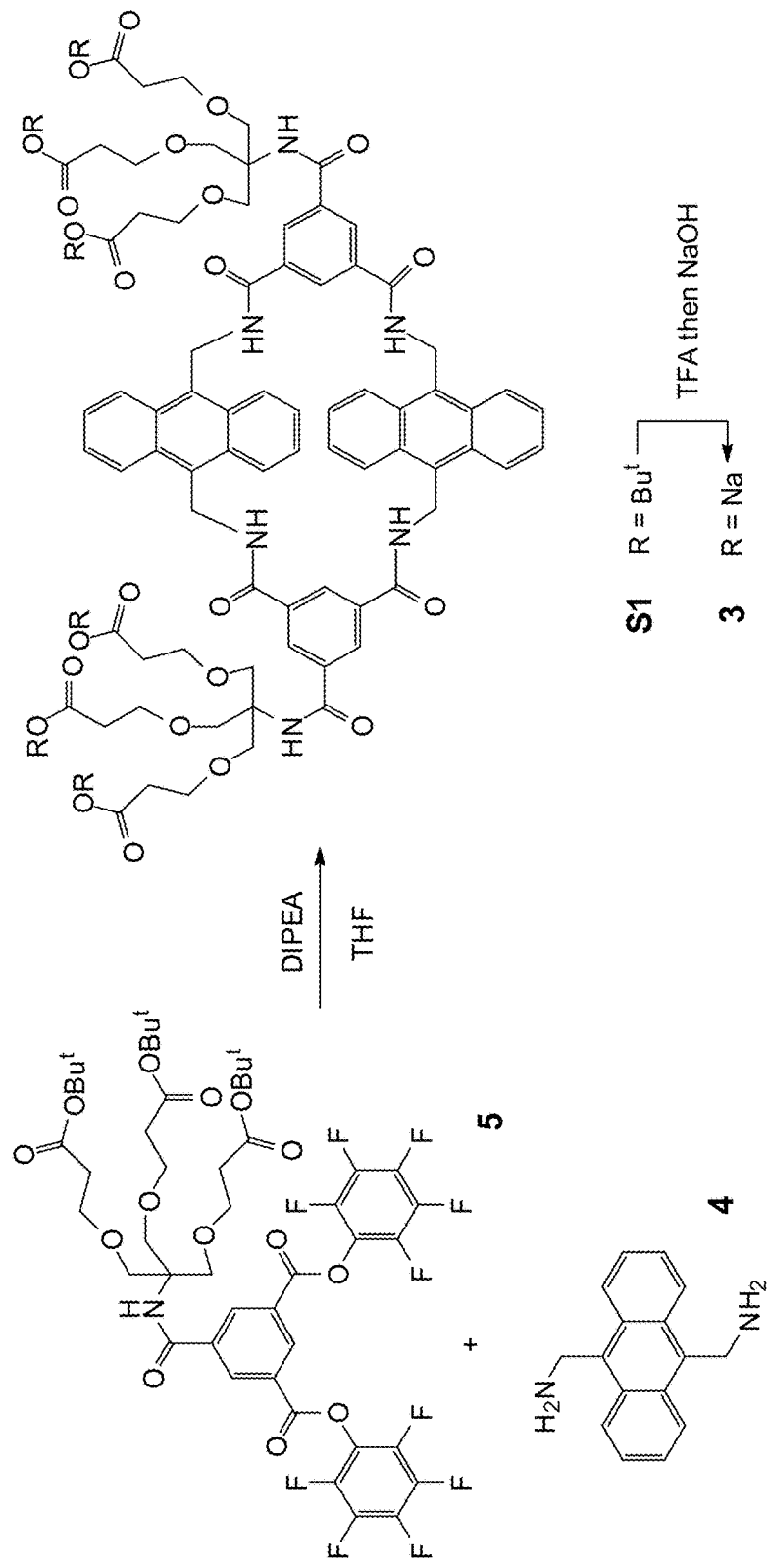
FIG. 4 shows a reaction scheme for preparing compound 3, as discussed in Example 1 below.

The detailed method for synthesising 3 was as follows (reaction scheme shown in FIG. 4).

t-Butyl Protected Macrocycle S1:

Firstly, the bis-pentafluorophenyl ester 5 was prepared in three steps from tris(hydroxymethyl)aminomethane, t-butyl acrylate and benzene-1,3,5-tricarbonyl chloride [see Klein, E et al, *Angew Chem, Int Ed*, 44: 298-302 (2005)]. A solution of 5 (1.6 g, 1.55 mmol) was then prepared in anhydrous THF (45 mL), and the solution was added dropwise over 30 hours (syringe pump) to a solution of 9,10-bis(aminomethyl)anthracene 4 (367 mg, 1.55 mmol) and DIPEA (5 mL) in anhydrous THF (1 L) under nitrogen. After stirring for a further 24 hours, the solvent was removed under reduced pressure. The residue was dissolved in DCM (100 mL) and washed with saturated aqueous NH$_4$Cl (100 mL), water (100 mL) and brine (100 mL). The organic solution was dried over Na$_2$SO$_4$ and evaporated in vacuo. The residue was taken up in DMSO (12 mL) and insoluble material removed by a syringe filter (0.45 μm). The DMSO solution was injected into a preparative HPLC apparatus fitted with a reverse phase column (Hichrom Kromasil, 150×21.2 mm, 5 μm) and eluted with methanol/water (90:10 to 100:0 over 5 minutes, then 100:0 for a further 15 minutes; flow rate=20 mL/min). The component eluting at 8.5 minutes was collected and freeze-dried to yield macrocycle S1 (370 mg, 0.21 mmol, 27%) as a pale yellow powder. $^1$H NMR (500 MHz, CDCl$_3$, TMS standard) δ=8.49 (d, 4H, J=1.7 Hz, ArH), 8.30 (dd, 8H, $^2$J=7.1 Hz, $^3$J=3.8 Hz, AnH), 7.46 (dd, 8H, $^2$J=7.1 Hz, $^3$J=3.8 Hz, AnH), 7.43 (s, 2H, ArH), 6.70 (s, 2H, NHC(CH$_2$O)$_3$), 6.45 (t, 4H, $^3$J=4.5 Hz, AnCH$_2$NH), 5.52 (d, 8H, $^2$J=5.1 Hz, AnCH$_2$NH), 3.87 (s, 12H, C(CHO)$_3$), 3.73 (t, 12H, $^3$J=6.4 Hz, CH$_2$CH$_2$O), 2.51 (t, 12H, $^3$J=6.4 Hz, CH$_2$CH$_2$O), 1.39 (s, 54H, C(CH$_3$)$_3$). $^{13}$C NMR (125 MHz, CDCl$_3$) δ=171.13 (CH$_2$CO$_2$), 165.82 (AnCH$_2$NHCOAr), 161.27 (ArCONHC), 134.75 (Ar), 130.20 (An), 129.69 (An), 126.52 (An), 124.70 (An), 80.68 (C(CH$_3$)$_3$), 69.13 (C(CH$_2$O)$_3$), 67.26 (OCH$_2$CH$_2$CO$_2$t-Bu), 60.57 (C(CH$_2$O)$_3$), 37.28 (AnCH$_2$NH), 36.46 (OCH$_2$CH$_2$CO$_2$t-Bu), 28.15 (C(CH$_3$)$_3$). An≡anthracenyl, Ar≡isophthalamide aryl. HRMS (ESI): m/z calculated for C$_{100}$H$_{126}$O$_{24}$N$_6$Na$_2^{2+}$[M+2Na$^{2+}$]=920.4304, found: 920.4272.

Also isolated was the corresponding [3+3] macrocycle (100 mg, 0.037 mmol, 5% yield, retention time=10 min).

Receptor 3 (Sodium Salt):

Macrocycle S1 (200 mg, 0.11 mmol) was dissolved in DCM (20 mL) and cooled in ice. Trifluoroacetic acid (TFA) (5 mL) was added dropwise to the solution. The reaction was allowed to warm to room temperature and stirred for 3 hours. The solvent was removed in vacuo, and the residue was suspended in water (5 mL). NaOH aq (0.5 M) was added dropwise until the suspended material dissolved, forming a clear solution. The clear solution was freeze-dried and further purified by preparative HPLC (apparatus as above), eluting with methanol/water (5:95 to 30:70 over 15 minutes, then to 100:0 over a further 15 minutes; flow rate=20 mL/min). The component with retention time=15 minutes was collected and freeze-dried to yield macrocycle 3 (150 mg, 85%). $^1$H NMR (500 MHz, D$_2$O) δ=8.39 (s, 4H, ArH), 8.27 (s, 8H, AnH$_A$ (for labelling see FIG. 9; anthracene protons A and B were distinguished through the intensities of the NOESY cross-peaks to AnCH$_2$NH)), 7.93 (bs, 2H, ArH), 7.51 (bs, 8H, AnH$_B$, 5.46 (bs, 8H, AnCH$_2$NH), 3.90 (s, 12H, C(CHO)$_3$), 3.78 (bs, 12H, OCH$_2$CH$_2$CO$_2$Na), 2.48 (bs, 12H, OCH$_2$CH$_2$CO$_2$Na). $^{13}$C NMR (125 MHz, D$_2$O) δ=179.98 (CH$_2$CO$_2$Na), 168.32 (AnCH$_2$NHCOAr), 162.87 (ArCONHC), 136.56 (Ar), 134.44 (Ar), 130.26 (An), 129.45 (An), 126.87 (An), 124.88 (An), 69.48 (C(CH$_2$O)$_3$), 69.37 (OCH$_2$CH$_2$CO$_2$Na), 61.51 (C(CH$_2$O)$_3$), 38.13 (AnCH$_2$NH), 37.53 (OCH$_2$CH$_2$CO$_2$Na). An≡anthracenyl, Ar≡isophthalamide aryl. HRMS (ESI): m/z calculated for C$_{76}$H$_{79}$N$_6$O$_{24}^+$[hexacarboxylic acid form+H$^+$]=1459.5169, found: 1459.5140.

EXAMPLE 2—SYNTHESIS OF ASYMMETRIC COMPOUNDS

Figure 5A:
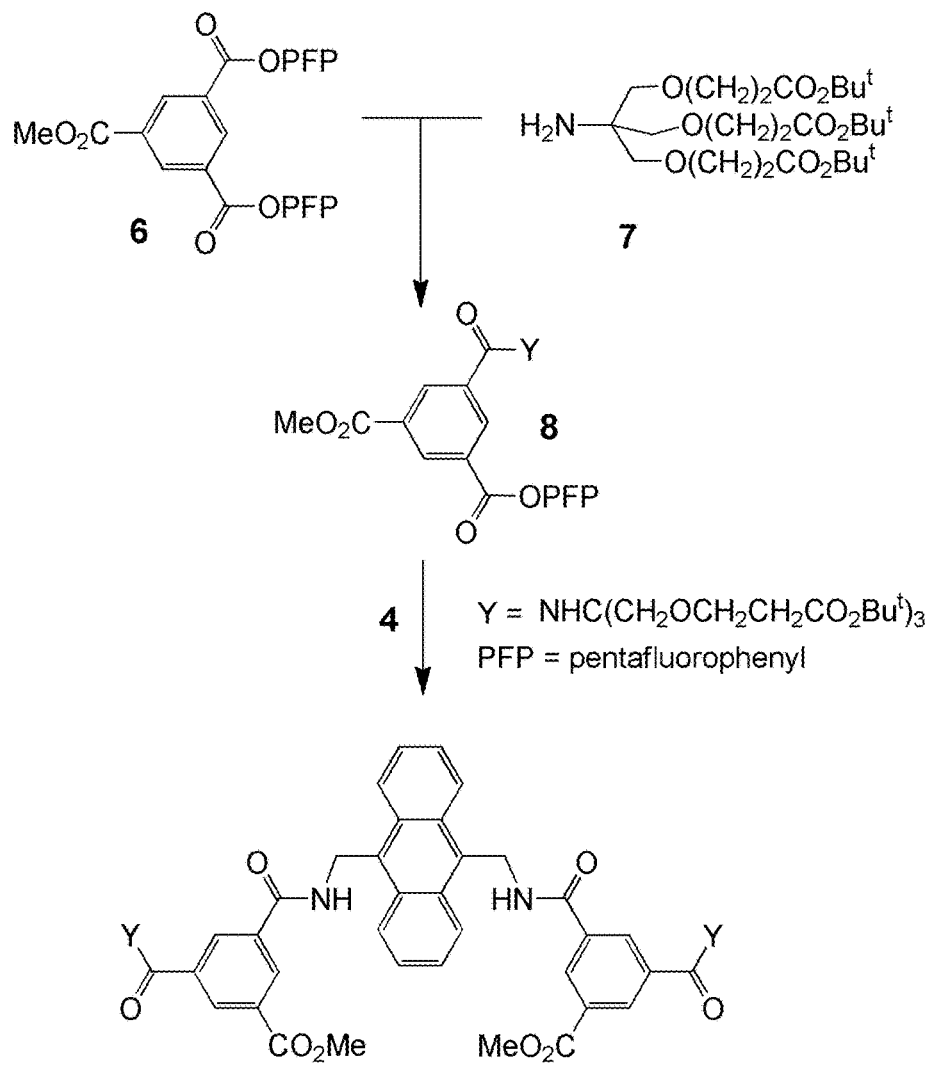
FIGS. 5A, 5B and 5C show reaction schemes suitable for preparing asymmetric versions of compounds according to the invention.

For comparison purposes, an asymmetric alternative, compound 9, was also synthesised using a method according to the invention, as depicted in FIG. 5A. In compound 9, a single anthracene unit is paired with a smaller p-xylyl unit. Although a longer sequence was required to prepare 9, the process was straightforward.

Firstly, the isophthaloyl moiety 6 was substituted with a t-butyl-protected form of the hydrophilic, water-solubilising group —NHC(CH$_2$OCH$_2$CH$_2$CO$_2^-$)$_3$, by reacting 6 with the amine 7. This yielded the compound 8, in which one of the potentially reactive C(O) groups was protected with a methoxyl group MeO. Compound 8 was then reacted with the diamine-substituted bis-anthracene 4, to yield an intermediate (referred to below as compound 11) in which a single anthracene moiety was bound to two isophthaloyl moieties.

The methoxyl protecting group on compound 11 was then replaced by the leaving group —O-PFP, using LiOH followed by PFP-OH and DCC, to yield a further reactive intermediate (referred to below as compound 12). Subsequently, 12 was reacted with p-xylylenediamine, in the presence firstly of TFA and then NaOH, to yield the final compound 9. In compound 9, the solubilising groups R$^9$ and R$^{10}$ are also now in their deprotected (ie carboxylate) forms.

Figure 5B:
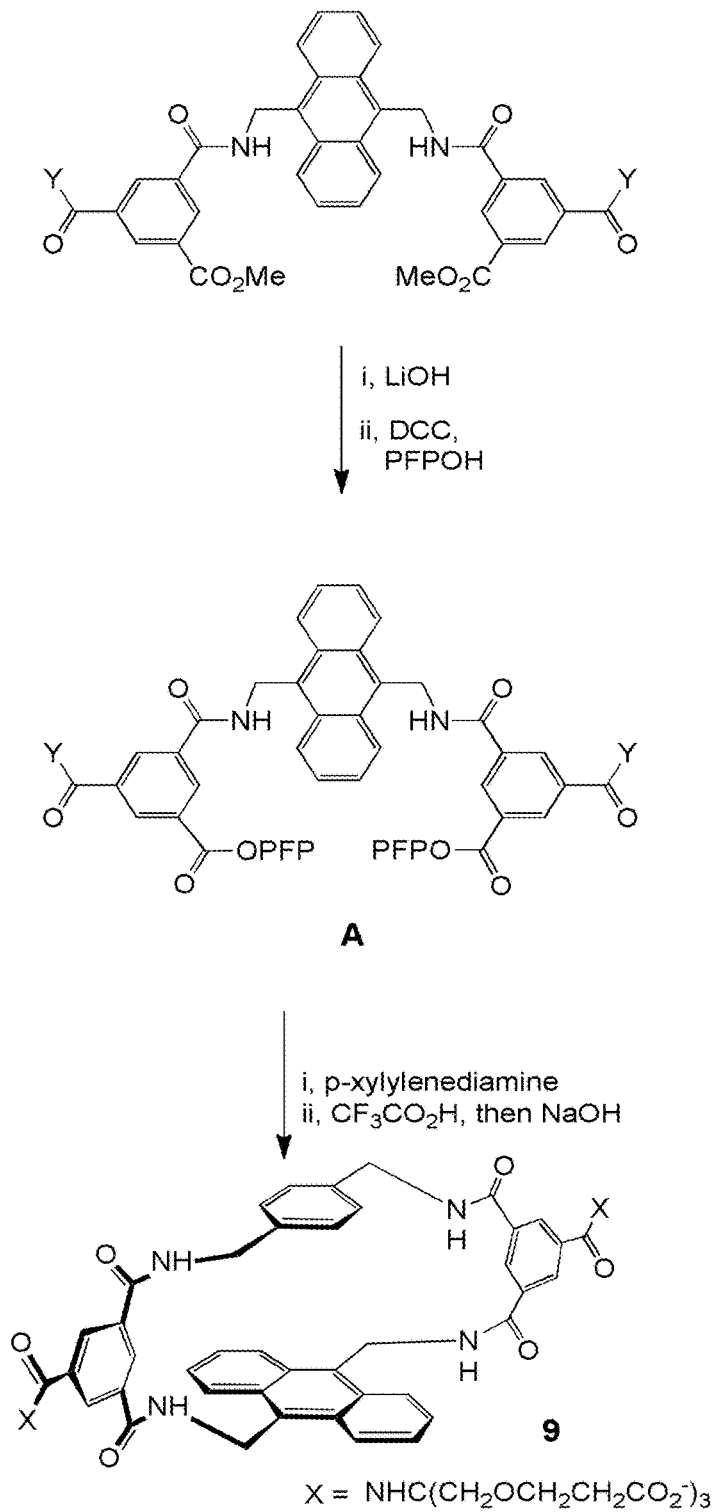

Alternatively, the intermediate 12 could be prepared by directly combining the reactants 4 and 5 (as in the preparation of the symmetric compound 3), so long as the compound 5 is present in moderate excess, for example at a molar ratio of 4:5 of around 1:3. This method is shown in FIG. 5B.

Figure 5C:
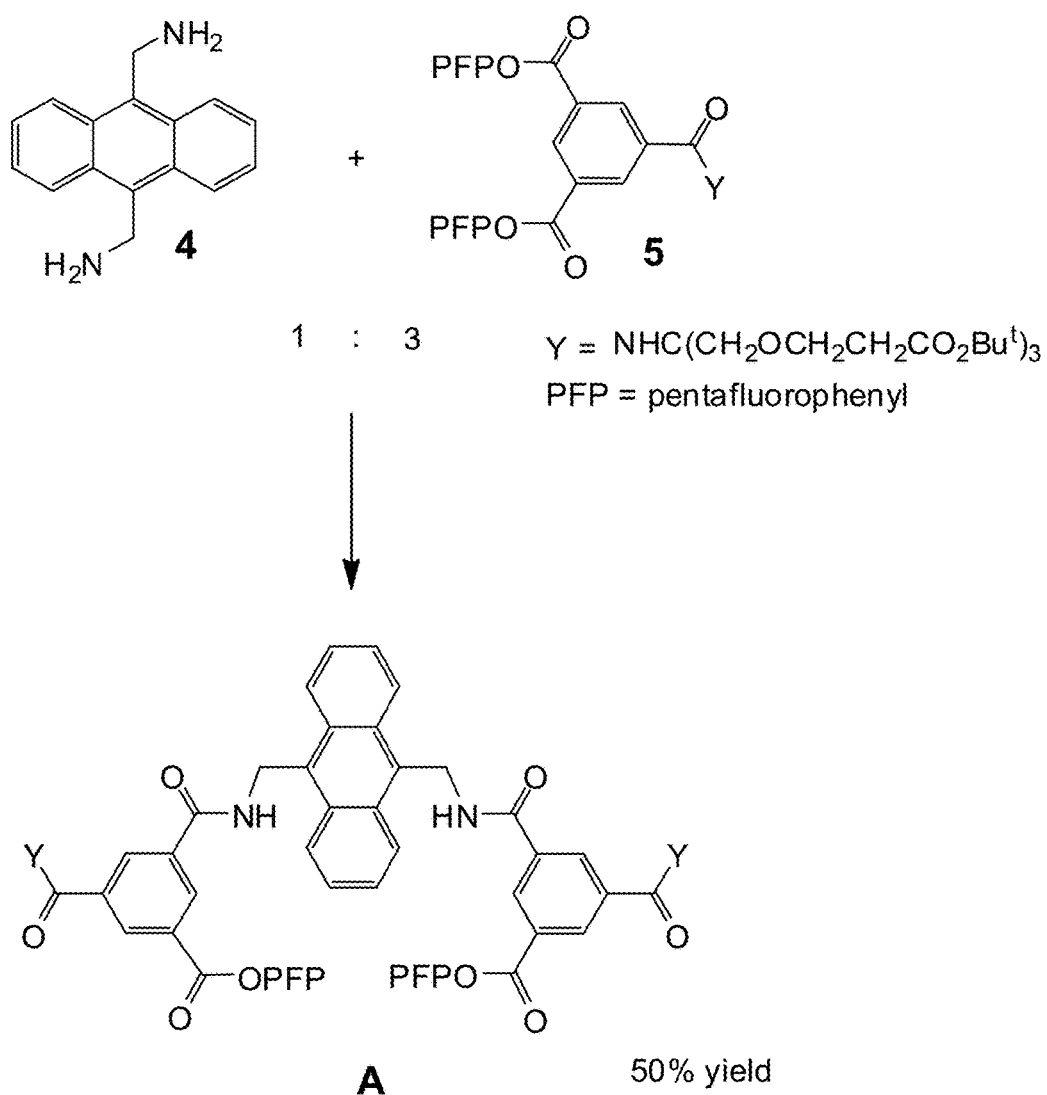

Aside from delivering a useful control compound, the routes shown in FIGS. 5A and 5C can be adapted to prepare a variety of asymmetric analogues of compound 3. It should thus be possible to tune the binding and/or optical properties of a compound according to the invention, for example by varying the substituents on the two anthracene units.

Figure 6A:
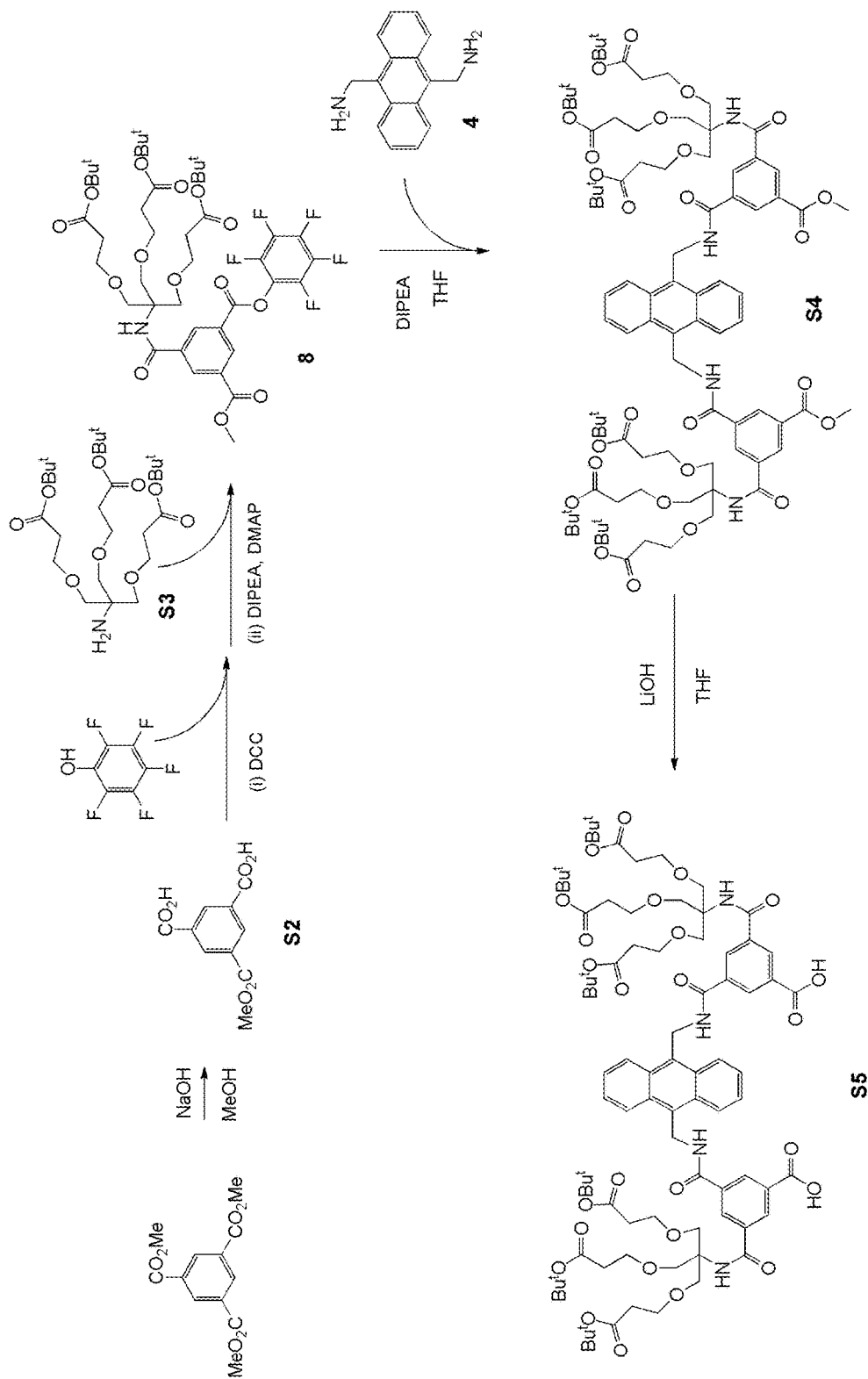
FIGS. 6A and 6B show in more detail a reaction scheme for preparing compound 9, as discussed in Example 2 below.
Figure 6B:
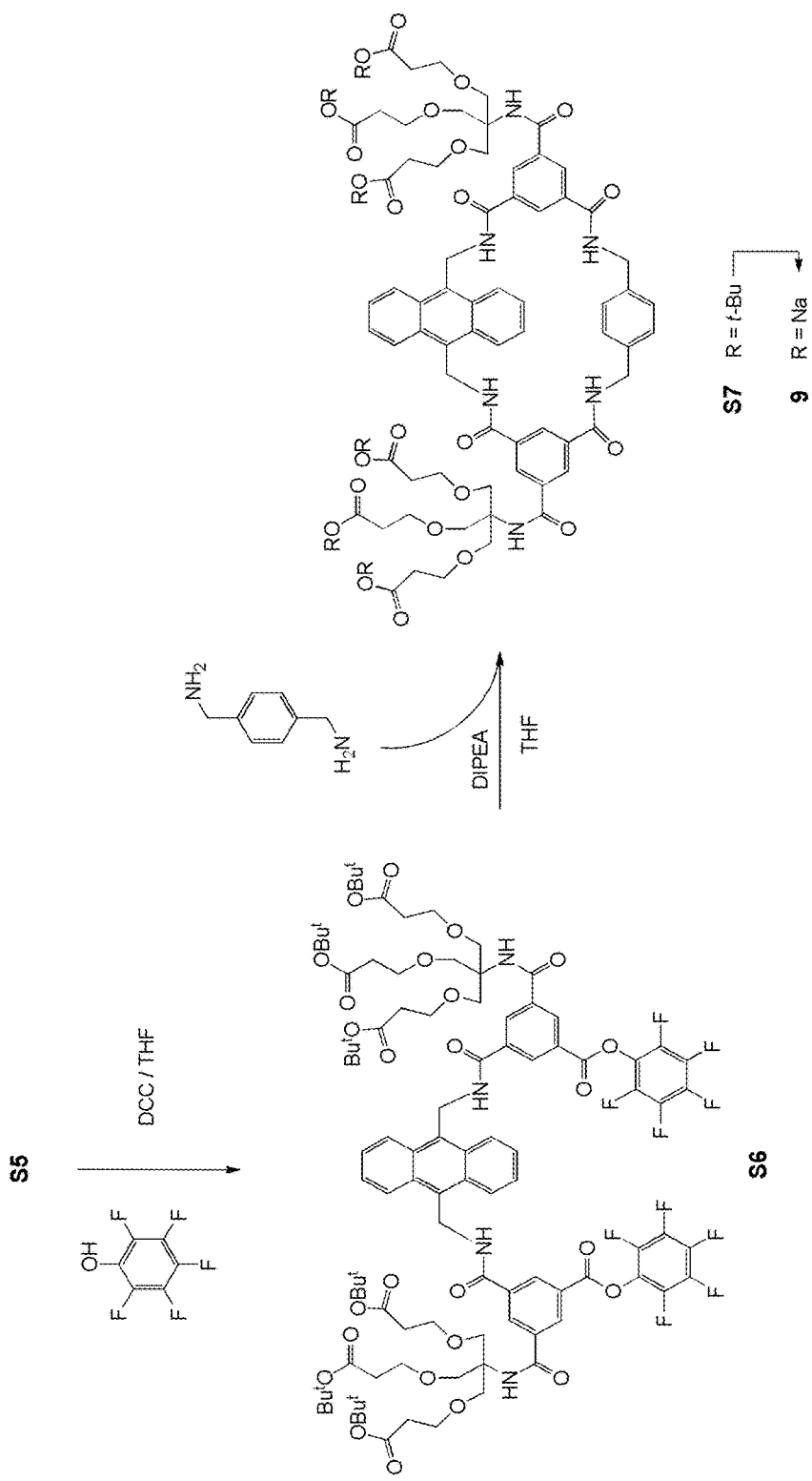

The detailed method for synthesising 9 was as follows (reaction scheme shown in FIGS. 6A and 6B).

Methyl 1,3,5-Benzenetricarboxylate S2.

Trimethyl 1,3,5-benzenetricarboxylate (22.0 g, 87.2 mmol) was dissolved in MeOH (700 mL). NaOH aq (6.97 g, 174.3 mmol NaOH in 100 mL water) was added dropwise with stirring. Stirring was continued at room temperature overnight, then the solvent was removed and the crude white solid was dissolved in saturated NaHCO$_3$ aq (600 mL). The pH of the solution was adjusted to 5.5 by adding HCl aq (1 M), and the aqueous solution was extracted with EtOAc (250 mL×3) to remove dimethyl 1,3,5-benzenetricarboxylate. The pH of the aqueous solution was then further adjusted to 4.4 and extracted with EtOAc (250 mL×3). The organic phases were combined, washed with brine, dried over MgSO$_4$ and concentrated in vacuo to afford S2 as a white solid (R$_f$=0.5, EtOAc:MeOH:H$_2$O=80:20:1). Yield 62% (12.2 g, 54.5 mmol). $^1$H NMR (400 MHz, (CD$_3$)$_2$CO) δ=8.86 (t, J=1.7 Hz, 1H), 8.82 (d, J=1.7, 2H), 3.98 (s, 3H). $^{13}$C NMR (100 MHz, (CD$_3$)$_2$CO) δ=166.1, 165.9, 135.3, 135.0, 132.8, 132.8, 132.4, 53.1. This material was used without further purification.

Pentafluorophenyl Ester 8.

Dicarboxylic acid S2 (6.00 g, 26.8 mmol) was dissolved in anhydrous THF (500 mL). Pentafluorophenol (11.04 g, 60.0 mmol) and N,N'-dicyclohexylcarbodiimide (DCC) (12.8 g, 62 mmol) were added under nitrogen atmosphere at room temperature and the mixture was stirred overnight. Amine S3 [Klein, E et al, "Carbohydrate recognition in water by a tricyclic polyamide receptor", *Angew Chem, Int Ed* 44: 298-302 (2005)] (13.5 g, 26.8 mmol) was dissolved in anhydrous THF (150 mL) with N,N-diisopropylethylamine (6.93 g, 53.6 mmol) and a catalytic amount of 4-dimethylaminopyridine (330 mg, 2.7 mmol, 5 mol %). This solution was added to the reaction mixture dropwise over 1 hour, after which the mixture was stirred for a further 24 hours under nitrogen. The solvent was evaporated, the crude product was suspended in diethyl ether (75 mL) and insoluble residues were removed by filtration. Concentration of the filtrate and purification by column chromatography on silica gel (EtOAc/hexane, 15:85 to 30:70), gave the product 8 as a clear oil (15.5 g, 17.4 mmol, 65%). $^1$H NMR (400 MHz, CDCl$_3$) δ=8.91 (t, J=1.6 Hz, 1H), 8.75 (t, J=1.6 Hz, 1H), 8.70 (t, J=1.6 Hz, 1H), 7.09 (s, 1H), 3.98 (s, 3H), 3.85 (s, 6H), 3.69 (t, J=6.2 Hz, 6H), 2.47 (t, J=6.2 Hz, 6H), 1.36 (s, 27H). $^{13}$C NMR (100 MHz, CDCl$_3$) δ=28.0, 36.2, 52.9, 61.0, 67.2, 69.1, 81.0, 125.4 (t, J$_{CF}$=13.2 Hz), 127.9, 131.6, 133.8, 134.0, 134.2, 136.9, 137.3, 139.2, 140.6, 141.1, 142.6, 161.4, 165.3, 166.5, 171.6. HRMS (ESI): m/z calculated for C$_{41}$H$_{51}$F$_5$NNaO$_{14}^+$[M+Na$^+$]=900.3200, found: 900.3178.

Bis-Methyl Ester Intermediate S4.

Diamine 4 (200 mg, 0.85 mmol) and pentafluorophenyl ester 8 (880 mg, 1.00 mmol) were dissolved in anhydrous THF (30 mL) under nitrogen. N,N-diisopropylethylamine (2 mL, 1.51 g, 12 mmol) was added. The mixture was stirred overnight at room temperature, after which analysis by TLC indicated that the reaction was complete. The solvent was removed and the residue was purified by column chromatography on silica gel (hexane/EtOAc, 1:1 then 3:4) to obtain intermediate S4 as a yellow solid (630 mg, 78%). R$_f$=0.5 (hexane/EtOAc, 2:3). $^1$H NMR (400 MHz, CDCl$_3$) δ=8.73 (t, J=1.6 Hz, 2H), 8.57 (t, J=1.6 Hz, 2H), 8.46 (dd, J=6.9, 3.3 Hz, 4H), 8.15 (t, J=1.7 Hz, 2H), 7.60 (dd, J=6.9, 3.2 Hz, 4H), 7.50 (t, J=4.4 Hz, 2H), 6.50 (s, 2H), 5.69 (d, J=4.6 Hz, 4H), 3.93 (s, 6H), 3.71 (s, 12H), 3.52 (t, J=6.2 Hz, 12H), 2.17 (t, J=6.2 Hz, 12H), 1.20 (s, 54H). $^{13}$C NMR (100 MHz, CDCl$_3$) δ=171.1, 165.9, 165.7, 165.6, 135.6, 134.8, 131.9, 131.7, 131.2, 130.4, 129.6, 129.1, 126.4, 124.9, 80.6, 68.9, 67.0, 60.3, 52.4, 36.0, 27.8. HRMS (ESI): m/z calculated for C$_{90}$H$_{127}$N$_4$O$_{26}^+$[M+H$^+$]=1623.8584, found: 1623.8610.

Dicarboxylic Acid Intermediate S5.

Intermediate S4 (630 mg, 0.39 mmol) was dissolved in THF (30 mL) at room temperature. LiOH.H$_2$O (170 mg, 3.90 mmol) was added, followed by H$_2$O (3 mL). The mixture was stirred overnight at room temperature then the solvent was removed by evaporation, keeping the temperature below 40° C. The residue was dissolved in H$_2$O (30 mL), and the pH was adjusted to ca 4-5 by addition of HCl aq. The mixture was extracted with EtOAc (2×60 mL) and the combined organic phases were dried over Na$_2$SO$_4$. Evaporation of the solvent gave diacid S5 as a clear oil, which was used without further purification (593 mg, 95%). $^1$H NMR (400 MHz, DMSO-d$_6$) δ=9.25 (s, 2H), 8.55 (dd, J=7.0, 3.3 Hz, 4H), 8.47 (d, J=1.5 Hz, 2H), 8.39 (s, 2H), 8.37 (s, 2H), 7.70-7.54 (m, 6H), 5.56 (d, J=4.4 Hz, 4H), 3.64 (s, 12H), 3.54 (t, J=6.1 Hz, 12H), 2.35 (t, J=6.1 Hz, 12H), 1.31 (s, 54H). $^{13}$C NMR (125 MHz, DMSO-do) δ=170.53, 170.44, 165.89, 138.84, 135.24, 134.14, 130.27, 129.77, 129.35, 126.83, 125.23, 124.28, 120.45, 79.40, 67.66, 66.20, 66.13, 59.97, 59.89, 38.15, 37.98, 37.81, 37.64, 37.47, 37.31, 37.14, 35.08, 35.01, 26.38, 26.33. HRMS (ESI): m/z calculated for C$_{84}$H$_{114}$N$_4$O$_{26}$Na$^+$[M+Na$^+$]=1617.7637, found: 1617.7614.

Bis-Pentafluorophenyl Ester S6.

Pentafluorophenol (170 mg, 0.93 mmol), DCC (191 mg, 0.93 mmol) and diacid S5 (593 mg, 0.37 mmol) were dissolved in anhydrous THF (100 mL) under nitrogen. 4-Dimethylaminopyridine (DMAP) (5 mg, 0.04 mmol) was added, and the mixture was stirred at room temperature overnight. The solvent was then removed and the residue was purified by column chromatography on silica gel (hexane/EtOAc, 2:1) to obtain the activated ester S6 as a yellow solid (420 mg, 60%). $R_f$=0.8 (hexane: EtOAc, 1:1). $^1$H NMR (500 MHz, CDCl$_3$) δ=8.94 (t, J=1.7 Hz, 2H), 8.76 (t, J=1.6 Hz, 2H), 8.48 (dd, J=7.0, 3.2 Hz, 4H), 8.25 (s, 2H), 7.72 (d, J=4.7 Hz, 2H), 7.62 (dd, J=6.9, 3.2 Hz, 4H), 6.58 (s, 2H), 5.72 (d, J=4.7 Hz, 4H), 3.70 (s, 12H), 3.51 (t, J=6.1 Hz, 12H), 2.14 (s, 11H), 1.19 (s, 54H). $^{13}$C NMR (100 MHz, CDCl$_3$) δ=171.16, 165.42, 164.97, 161.47, 136.02, 135.24, 133.15, 130.42, 129.57, 128.09, 126.48, 124.90, 80.66, 68.85, 67.07, 66.94, 60.44, 36.85, 36.02, 27.92, 27.79, 27.71. HRMS (ESI): m/z calculated for $C_{96}H_{112}N_4O_{26}F_{10}N^+$[M+Na$^+$]=1949.7275, found: 1949.7297.

t-Butyl Protected Macrocycle S7.

Bis-pentafluorophenyl ester S6 (400 mg, 0.21 mmol) was dissolved in anhydrous THF (40 mL) to make solution A. p-Xylenediamine (29 mg, 0.21 mmol) was dissolved in anhydrous THF (40 mL) to make solution B. Using a syringe pump, solutions A and B were then added simultaneously over 30 hours to a solution of DIPEA (5 mL, 53.8 mmol) in anhydrous THF (700 mL) under nitrogen. The reaction was stirred for a further 24 hours, then the solvent was evaporated and the residue was re-dissolved in CH$_2$Cl$_2$ (150 mL). The solution was washed with saturated aqueous NH$_4$Cl (100 mL), brine (100 mL) and NaHCO$_3$ (100 mL). The organic layer was collected and dried over MgSO$_4$. The solvent was evaporated and the residue was purified by preparative HPLC using the previously-described apparatus, eluting with methanol/water (90:10 to 100:0 over 20 min; flow rate=20 mL/min). The component with retention time=11.3 min was collected and freeze-dried to yield macrocycle S7 (120 mg, 34%) as a light yellow solid. $^1$H NMR (500 MHz, CDCl$_3$) δ=8.64 (s, 2H), 8.39 (dd, J=6.9, 3.2 Hz, 4H), 8.13 (s, 2H), 7.81 (s, 2H), 7.64 (s, 2H), 7.59 (dd, J=6.9, 3.0 Hz, 4H), 7.10 (s, 4H), 6.68 (s, 2H), 6.28 (s, 2H), 5.69 (d, J=4.2 Hz, 4H), 4.43 (d, J=6.0 Hz, 4H), 3.86 (s, 12H), 3.72 (t, J=6.2 Hz, 12H), 2.48 (t, J=6.1 Hz, 12H), 1.39 (s, 54H). $^{13}$C NMR (125 MHz, CDCl$_3$) δ=171.2, 166.3, 166.2, 165.5, 137.2, 136.7, 135.0, 134.9, 130.6, 130.3, 129.5, 127.7, 127.6, 127.2, 126.8, 124.6, 80.7, 69.1, 67.2, 60.4, 43.8, 36.9, 36.5, 28.1.

Macrocyclic Hexacarboxylate 9.

Macrocycle S7 (120 mg, 0.07 mmol) was dissolved in DCM (20 mL) and cooled in ice. TFA (3 mL) was added dropwise and the solution was stirred for 3 hours at room temperature. The solvent was removed in vacuo, and the residue was suspended in water (5 mL). NaOH aq (0.5 M) was added drop-wise until the suspended material dissolved, forming a clear solution. The amount of NaOH was calculated as ca 8 equivalents with respect to S7. The clear solution was freeze-dried to obtain a light yellow powder (99% yield). This product was further purified by preparative HPLC (apparatus as above), eluting with methanol/water (5:95 to 30:70 over 15 minutes, then to 100:0 over a further 15 minutes; flow rate=20 mL/min). The component with retention time=12.1 min was collected and freeze-dried to yield macrocycle 9 (75 mg, 0.05 mmol, 71%). $^1$H NMR (500 MHz, D$_2$O) δ=8.48 (dd, J=6.9, 3.4 Hz, 4H), 8.38 (q, J=1.2, 0.8 Hz, 2H), 8.22 (q, J=1.2, 0.8 Hz, 2H), 7.84 (s, 2H), 7.67 (dd, J=6.9, 3.2 Hz, 4H), 7.14 (d, J=1.0 Hz, 4H), 5.65 (s, 4H), 4.44 (s, 4H), 3.89 (m, 12H), 3.79 (m, 12H), 2.48 (m, 12H). $^{13}$C NMR (125 MHz, D$_2$O) δ=180.2, 135.3, 134.4, 129.4, 127.2, 126.1, 124.5, 117.5, 115.1, 112.8, 68.8, 68.6, 60.9, 48.8, 37.7. HRMS (ESI): m/z calculated for $C_{68}H_{75}N_6O_{24}^+$[hexacarboxylic acid form+H$^+$]=1359.4817, found: 1359.4827.

EXAMPLE 3—STRUCTURAL ANALYSIS OF COMPOUND 3

The structure and properties of the compound 3 prepared in Example 1 were investigated as follows.

The compound was dissolved in D$_2$O at concentrations up to ~4 mM giving clean, if slightly broadened, $^1$H NMR spectra. Minor signal movements were observed on dilution to ~1 mM but no further effect was observed below this concentration, implying that the system is monomeric at 1 mM or less.

Figure 8A:
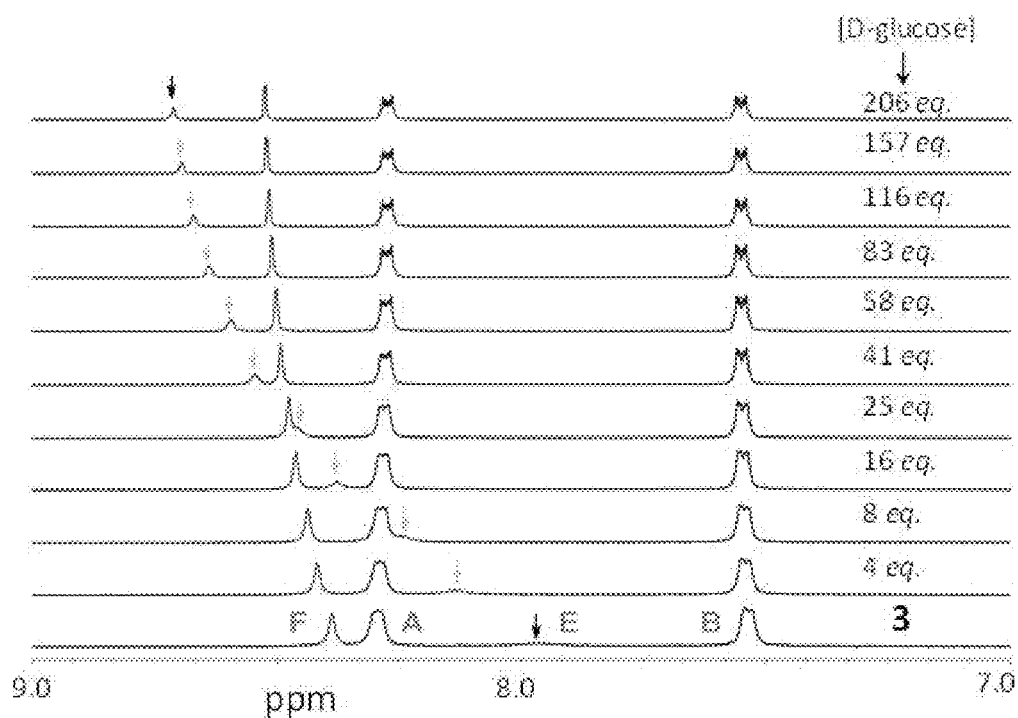

The partial $^1$H NMR spectrum for compound 3 alone can be seen in FIG. 8A, closest to the baseline.

EXAMPLE 4—BINDING STUDIES—$^1$H NMR

Figure 7:
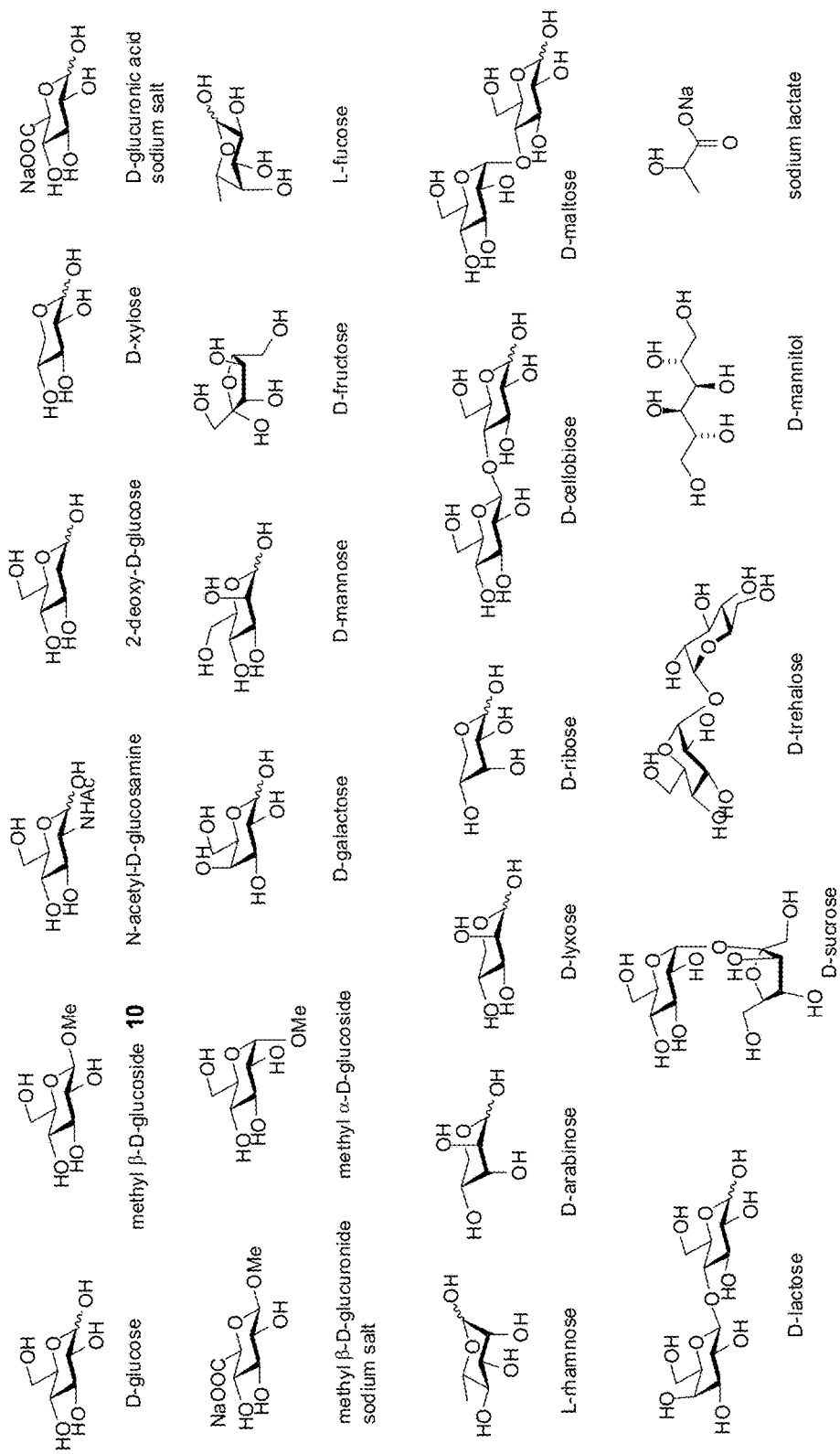
FIG. 7 shows the structures of test substrates used in binding studies with the compounds 3 and 2.

The binding of receptor compound 3 to carbohydrate substrates, in aqueous solution, was studied initially by $^1$H NMR titrations at 298 K. The saccharides used as test substrates are shown in FIG. 7.

Titrations were performed on a Varian™ 500 MHz spectrometer. Solutions of reducing carbohydrates were prepared in D$_2$O and kept overnight at room temperature before the titration experiments, in order to ensure equilibration of anomers. In a typical titration, aliquots of carbohydrate solution were added to receptor solution (DSS as internal standard) and the $^1$H NMR spectra were recorded. Variations in chemical shifts were entered into a specifically written non-linear least squares curve-fitting program implemented within Excel™. Assuming 1:1 stoichiometry, the program calculates $K_a$ and the limiting change in chemical shift Δδ. The assumption is supported by the generally good fits between observed and calculated data.

The partial NMR spectra for binding studies with glucose (ie D-glucose), using 1.1 mM 3 with glucose at 0 to 200 mM, are shown in FIG. 8A. FIG. 9 provides a key to the peak assignments in the spectra.

Figure 8B:
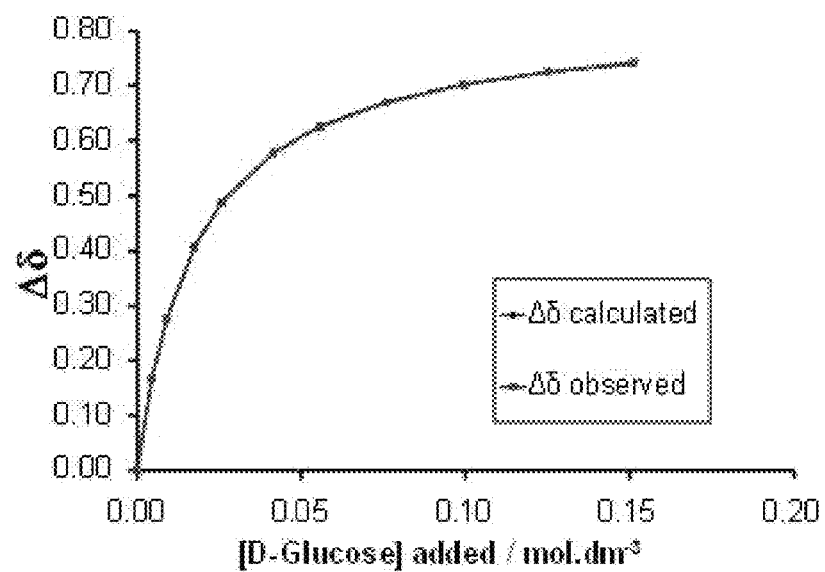

The NMR data showed that the addition of some carbohydrates to 3 caused substantial changes to its NMR spectrum, especially to the chemical shifts of the isophthaloyl protons E and F. For example, the addition of glucose caused a downfield movement of the signal due to internally-directed protons E, with Δδ tending towards ~0.8 ppm (FIG. 8A). The signal due to externally-directed protons F also shifted downfield, by ~0.15 ppm. Small movements of the signals due to anthracene protons A and B were observed, while the spectrum sharpened considerably during the titration. The movements of protons E and F gave excellent fits to a 1:1 binding model: FIG. 8B shows the overlapping observed and calculated binding curves for the NMR proton E, yielding values for the association constant $K_a$ of 58 and 54 M$^{-1}$ respectively (average=56 M$^{-1}$).

Data for the other test substrates were analysed similarly, to give the binding constants listed in Table 1 below. Values for the tricyclic system 2 are recorded for comparison purposes.

TABLE 1

Table 1: Association constants measured by $^1$H NMR titration in D$_2$O at 298 K. For structures of test substrates see FIG. 7. Values denoted ~0 were too small for analysis. Errors were estimated at ≤10% for most cases where $K_a$ ≥ 10 M$^{-1}$.

| | Substrate | $K_a$ (M$^{-1}$) 3 | 2‡ |
|---|---|---|---|
| All-equatorial monosaccharides | D-glucose | 56 (58*, 55†) | 60 |
| | methyl β-D-glucoside 10 | 96 (121*, 101†) | 130 |
| | 2-deoxy-D-glucose | 36 | 29 |
| | N-acetyl-D-glucosamine | 10 | 7 |
| | D-xylose | 9 | 17 |
| | D-glucuronic acid, sodium salt | 24 | |
| | methyl β-D-glucuronide, sodium salt | 87 | |
| Other monosaccharides | methyl α-D-glucoside | 6 | 15 |
| | D-galactose | 1 | 3 |
| | D-mannose | 1 | ~1 |
| | D-fructose | ~0 | |
| | L-rhamnose | ~0 | ~0 |
| | L-fucose | ~0 | 3 |
| | D-arabinose | 1 | 4 |
| | D-lyxose | ~0 | ~1 |
| | D-ribose | ~0 | 6 |
| Disaccharides and miscellaneous substrates | D-cellobiose | 28 | 71 |
| | D-maltose | 35 | ~0 |
| | D-lactose | 16 (9*) | 8 |
| | D-sucrose | ~0 | |
| | D-trehalose | ~0 | |
| | Mannitol | ~0 | |
| | sodium lactate | ~0 | |

*Measured by fluorescence titration in phosphate buffer solution (pH 7.1, 0.1M) at 298 K.
†Measured by ITC titration in water at 298 K.
‡Data from Harwell et al, supra.

Given the relative simplicity of 3, one might expect reduced performance in comparison to 2. Remarkably, however, the two systems behave quite similarly, the main difference being that 3 is the more selective for glucose vs other monosaccharides. Thus, both 2 and 3 prefer the all-equatorial carbohydrate moieties, binding well to molecules containing the all-equatorial β-glucosyl unit and compounds containing it, for example glucose (for which the $K_a$ values are almost identical), methyl β-D-glucoside and, to a lesser extent, 2-deoxyglucose, N-acetylglucosamine and xylose (all three of which are all-equatorial molecules). Compound 3 also binds fairly strongly to anionic glucuronic acid derivatives. Selectivity against other monosaccharides is generally good for both systems, but again 3 is appreciably superior. Aside from methyl α-D-glucoside, all "non-target" monosaccharides were bound by 3 with $K_a$≤1 m$^{-1}$. With disaccharides, 3 seems to bind significantly to any system containing β-glucosyl (cellobiose, maltose, lactose). Here there is a qualitative difference from 2, which binds cellobiose well but shows no affinity for maltose. Such binding affinities are not generally problematic, however, in the context of blood glucose monitoring, since molecules such as cellobiose, maltose and lactose are unlikely to be present in the bloodstream at significant concentrations compared to the likely glucose concentration.

Thus, it can be seen that the compound 3, according to the invention, demonstrates a surprisingly good affinity, and selectivity, for glucose, whilst also being simpler in structure and thus more readily accessible than the prior art compound 2. This illustrates the likely utility of compound 3, and related compounds, in the detection of blood glucose levels.

EXAMPLE 5—BINDING STUDIES—FLUORESCENCE SPECTROSCOPY

Receptor-carbohydrate complex formation can also be studied by fluorescence spectroscopy.

Fluorescence titrations were carried out at 298 K on a PerkinElmer™ LS45 spectrometer in PBS (phosphate buffered saline) buffer solution (pH 7.1, 100 mM). The carbohydrate stock solutions were prepared by dissolving the carbohydrates in buffer containing the receptor at the concentration to be used in the titration (thus avoiding dilution of the receptor during the experiment). The solutions were kept overnight at room temperature before the titration experiments, in order to ensure equilibration of anomers. The wavelength to be used for fluorescence excitation was determined by measurement of the UV-visible spectrum of receptor 3 in the presence of carbohydrates. 394 nm was chosen, because at this wavelength the absorption of receptor was almost independent of carbohydrate concentration. In a typical titration, aliquots of carbohydrate-receptor solution were added to receptor solution (2.5 mL) in a quartz cuvette (3 mL, 10 mm pathway). The solution was stirred for 2 minutes and left to stand for another 1 minute before the emission spectrum was recorded. Binding constants were calculated using non-linear curve fitting assuming 1:1 binding stoichiometry, employing both Kaleidagraph™ and a customised Excel™ spreadsheet. Errors were estimated at <5%.

Figure 8D:
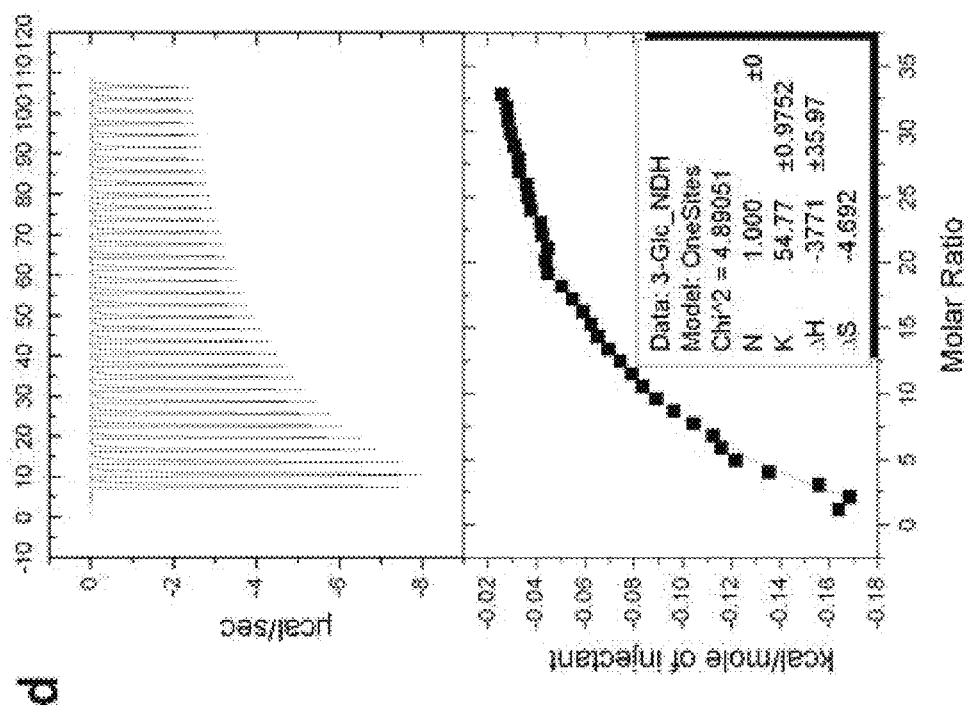
Figure 8C:
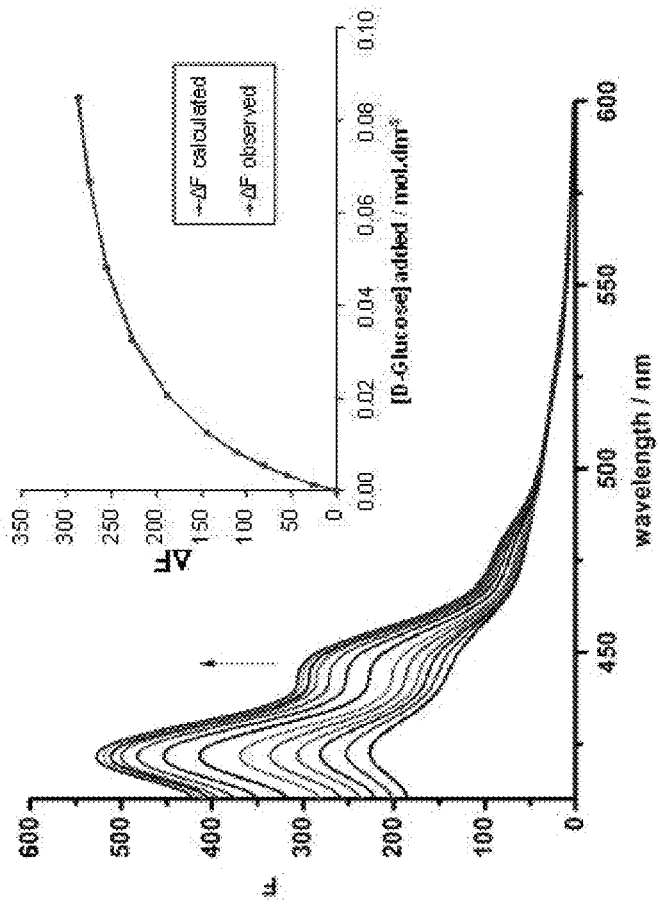

The spectrum for compound 3 (18.8 μM) with glucose is shown in FIG. 8C. It can be seen that on excitation with UV light at 394 nm, 3 emitted in the blue-violet region, peaking at 423 nm, with a quantum yield of 2.4% (20 μm aqueous solution). Addition of glucose caused the emission intensity to increase by factors of up to 2.5. Analysis of the changes gave, again, an excellent fit to a 1:1 binding curve (shown as an inset in FIG. 8C; binding data at 423 nm; $K_a$=58 M$^{-1}$). Binding constants obtained by this method were in good agreement with those measured by NMR titrations (see Table 1). Moreover these fluorescence characteristics are promising for practical glucose sensing, especially when compared to biphenyl-based synthetic lectins. The excitation wavelength is only just outside the visible region, thus relatively safe and obtainable with inexpensive UV LEDs. In contrast, the biphenyl-based systems require light at ~280 nm for excitation, and produce far weaker emissions which do not always change on binding. The excitation wavelength for a compound according to the invention can moreover be tuned, for instance to bring it within the visible spectrum, by modification of the substituents R$^1$ to R$^8$ on the anthracene units. The observed mode of binding of compound 3 to glucose suggests that changes to the anthracene unit, in particular at its two ends, should have only minor effects on binding.

EXAMPLE 6—BINDING STUDIES—ISOTHERMAL TITRATION CALORIMETRY

The binding of 3 to glucose and methyl β-D-glucoside was studied by a third technique, isothermal titration calorimetry (ITC). Experiments were performed on a VP-ITC™ (Microcal, Inc., Northampton, Mass.) at 298 K. Stock solutions of carbohydrates were made up in pure HPLC grade water and allowed to equilibrate overnight. Receptor solutions were made up in pure water. All the solutions were degassed and thermostated using the ThermoVac™ accessory before titration. The sample cell volume was 1.4226 mL. Each titration experiment included 25-35 successive injections. The output trace for 3 and glucose is shown in FIG. 8D; analysis of these data yielded a value for $K_a$ of 55 $M^{-1}$.

Measured affinities were again consistent with those determined by NMR titrations (Table 1), and revealed that complexation was enthalpy-driven with significant negative entropies (eg for glucose, $\Delta H=-3.8$ kcal $mol^{-1}$, $T\Delta S=-1.4$ kcal $mol^{-1}$). This contrasts with the oligophenyl-based synthetic lectins, where binding entropies are positive (eg for 2+10, $\Delta H=-0.6$, $T\Delta S=2.3$ kcal $mol^{-1}$). However, negative binding entropies are common for natural lectins. The observation of negative $\Delta S$ does not preclude a role for hydrophobic interactions. Indeed, with fewer polar spacers, it seems likely that 3 is less dependent on polar interactions than tricyclic cages such as 2, and thus more reliant on the displacement of high-energy water. This is supported by experiments in less polar media, where H-bonding must dominate. Thus the organic soluble (t-butyl protected) precursor of 3 bound octyl β-D-glucoside in chloroform with $K_a=3200$ $M^{-1}$. The corresponding value for a biphenyl-based system was ~100 times higher.

The role of non-polar interactions was highlighted by studies on the control macrocycle 9. This compound possesses the same polar groups as 3, but provides less apolar surface for hydrophobic CH-π interactions. Addition of some carbohydrates (eg glucose and xylose) to 9 yielded minor changes in the $^1$H NMR spectrum of the macrocycle. However signal movements were almost linear with concentration, implying $K_a$ was too small to measure.

EXAMPLE 7—FURTHER STRUCTURAL STUDIES

The 3D structure of 3 and its complex with methyl β-D-glucoside 10 was studied by 2D nOe spectroscopy (NOESY). The resultant structures are illustrated in FIGS. 10A and 10B. FIG. 10A shows a view of the complex roughly parallel to the tetralactam ring. The anthracene units and the substrate are shown in space-filling mode, while the solubilising side-chains are removed for clarity. FIG. 10B shows a view roughly perpendicular to the tetralactam ring. The figure shows the shortest intermolecular distances (according to NOESY) D-4 and D-5, the longer D-$6_R$ distance, and the intramolecular D-E contacts. The four NH • • • O hydrogen bonds appear as dotted lines.

In the case of 3 itself, a key issue to be investigated was the orientation of the annular amide groups, which in theory can be positioned such that either NH or CO point inward. Strong NOESY cross-peaks between NH protons D and spacer CH E (see FIG. 10B), and the absence of connections D-F, indicated that inward-directed NH groups are preferred. The data thus support the calculated structure shown in FIGS. 10A and 10B.

To study the complex 3.10, an excess of 10 was added such that ~90% of 3 was in the bound state. Again, the intramolecular NOESY signals showed a strong preference for the "NH-in" arrangement. A large number of intermolecular cross-peaks were observed at long nOe mixing times, but at short mixing times the connections D-4 and D-5 stood out strongly, followed by D-$6_R$. These data are best accommodated by structures in which the substrate $CH_2OH$ passes through the tetralactam ring so that H4 and H5 can come into contact with two diametrically opposite protons D. One such structure is shown in FIGS. 10A and 10B. This substrate positioning allows the formation of four intermolecular NH • • • O bonds to four substrate oxygens, as well as 6 CH-π contacts. Interestingly, the distance between the aromatic surfaces in this structure is smaller than previously determined for a biphenyl-based synthetic lectin [see Ferrand et al, *Angew Chem Int Ed*, 48: 1775-1779 (2009)]. This suggests a tight fit, which may contribute to the negative entropy of binding.

The conformation in FIGS. 10A and 10B can help to explain the selectivity of 3 for specific saccharides. An axial OH group, as in galactose or mannose, would clearly disrupt this structure, while the loss of $CH_2OH$ from the substrate (to give xylose) would remove both polar and apolar binding interactions. On the other hand, several of the better test substrates (glucuronides, cellobiose, maltose, lactose) do not seem compatible with this binding geometry, so other modes of interaction could be possible.

EXAMPLE 8—FURTHER PROPERTIES OF COMPOUND 3

A number of further experiments were performed to test the potential of compound 3 for glucose monitoring in vivo.

Lactate and mannitol are carbohydrate-like molecules which can be present in blood, and which often bind to the boron-based receptors of the prior art. Neither produced any response when added to 3, thus confirming its selectivity for the desired target analyte.

Binding to glucose was also studied at physiological temperature (310 K). The affinity measured by NMR titration was 33 $M^{-1}$, lower than at room temperature (as expected). However this is still potentially useful, implying receptor occupancy of 6-25% across the physiological range of 2-10 mM glucose.

Photobleaching of 3 was found to be relatively slow. Under continuous UV irradiation in a fluorescence spectrometer, emission decayed by <10% in 5 hours. In a practical glucose monitoring device this would translate to a long lifetime as the receptor compound would be subjected only to short pulses of light every few seconds.

EXAMPLE 9—SYNTHESIS OF COMPOUND 13

The compound 13, shown in FIG. 12A, is another compound according to the first aspect of the invention, designed for the purpose of detecting glucose in blood. Due to the modified $R^9$ and $R^{10}$ groups attached to its isophthaloyl moieties, this compound benefits from enhanced aqueous solubility, rendering it particularly suitable for use in vivo for blood glucose monitoring.

A potential route to the synthesis of compound 13 is illustrated by the retrosynthetic scheme shown on FIGS. 13A-13C, and described in more detail below. This method, which accords with the eleventh aspect of the invention, can be seen in its latter stages to be analogous to the method proposed for the preparation of compound 3. However, it begins with the preparation and attachment, to an isophthaloyl precursor of formula (III), of the solubilising moiety which will represent the substituents $R^9$ and $R^{10}$ in the final product.

In FIGS. 13A-13C and the following description, the compound 13 appears as its sodium salt "AnR-G2-Na"; the isophthaloyl precursor of formula (III) as "G2-Linker"; the amine used to link the hydrophilic moiety to the isophthaloyl precursor as "G2-$NH_2$"; and the corresponding nitro-substituted form of the amine as "G2-$NO_2$". FIGS. 14A to 14D show the structures for G2-$NH_2$, G2-Linker and AnR-G2-

Na, and also (FIG. 14C) for a t-butyl-protected form ("AnR-G2-tBu") of the eventual sodium salt 13, in each case with the protons assigned.

Compound 13 was prepared using the route shown in FIGS. 13A-13C, as described below.

G2-NH$_2$.

To an autoclave (250 mL) the commercially available compound G2-NO$_2$ (3.89 g, 2.65 mmol), Raney Ni (7.5 mL, water slurry) and ethanol (100 mL) were added.

The autoclave was then sealed, pressured with H$_2$ (50 bar) and left stirring for 24 hours at 60° C. After cooling to room temperature the mixture was filtered through Celite and washed with DCM (50 mL), then the solvent was removed under reduced pressure to yield the product (3.46 g, 91%). $^1$H-NMR (500 MHz, CDCl$_3$): δ 1.42 (s, 81H, H1), 1.97 (t, 18H, H5), 2.15 (t, 6H, H10), 2.23 (m, 24H, H9/4), 2.38 (s, 2H, H12), 6.22 (s, 3H, H7). MS(ESI) calculated for C$_{76}$H$_{134}$O$_{21}$N$_4$H$^+$=1439.50; found 1439.96.

G2-Linker.

To a stirred suspension of tri-PFP (1.64 g, 2.31 mmol) and G2-NH$_2$ (1.70 g, 1.16 mmol) in a mixture of THF (10 ml, anhydrous, degassed) and CH$_2$Cl$_2$ (2 ml, anhydrous, degassed), DIPEA (1.81 ml, 10.4 mmol) was added. The reaction mixture was heated for two hours at 40° C., after which the clear solution was concentrated to dryness with a rotary evaporator. The resulting oil was purified via column chromatography (10:90 to 60:40 EA:HEX) to yield the product as a white solid (1.68 g, 74.0%). R$_f$=0.34 (40:60 EA:HEX). $^1$H-NMR (500 MHz, CDCl$_3$): δ 1.31 (s, 81H, H1), 1.84 (t, 18H, H5), 2.08 (m, 24H, H4/9), 2.23 (t, 6H, H10), 8.96 (t, 1H, H17), 9.15 (d, 2H, H15), 9.47 (s, 1H, H12). $^{19}$F-NMR (500 MHz, CDCl$_3$): δ −152.42 (d, 4F, F20), −157.75 (t, 2F, F22), −162.30 (t, 4F, F21). MS(ESI) calculated for C$_{97}$H$_{136}$F$_{10}$N$_4$O$_{26}$Na$^+$=1987.21; found 1987.10.

AnR-G2-t-Bu.

A solution of G2-Linker (439 mg, 0.22 mmol) in THF (100 mL, anhydrous) was added dropwise over 36 hours (syringe pump) to a solution of 9,10-bis(aminomethyl)anthracene (52.8 mg, 0.22 mmol) and DIPEA (2 mL, 12 mmol) in THF (900 mL, anhydrous) under nitrogen. After stirring for a further 36 hours the solvent was removed under vacuum and the residue dissolved into chloroform (200 mL) and washed with NH$_4$Cl (sat aq, 200 mL), water (200 mL) and brine (200 mL), then dried over MgSO$_4$, filtered and evaporated in vacuo. The crude was dissolved in acetone/water (5:2, 6 mL) and filtered through a syringe filter (0.45 m). The solution was injected into a preparative reverse phase HPLC apparatus fitted with a reverse phase column (Waters—Xselect, 250×19 mm, 5 m) and eluted with acetone/water (80:20 to 90:10 over 20 min; flow rate 19 mL/min). The component eluting at 19 min was collected, concentrated under vacuum and freeze-dried to yield AnR-G2-tBu (58 mg, 14%) as a pale yellow powder. R$_f$=0.7 (70:30 EtoAc:Hexane). $^1$H NMR (500 MHz, CDCl$_3$): δ=1.42 (s, 162H, H24), 2.01 (t, J$_{HH}$=7.3 Hz, 36H, H20), 2.22 (t, J$_{HH}$=7.0 Hz, 12H, H15), 2.24 (t, J$_{HH}$=7.3 Hz, 36H, H21), 2.32 (t, J$_{HH}$=7.0 Hz, 12H, H16), 5.53 (d, J$_{HH}$=4.9 Hz 8H, H5), 6.18 (s, 6H, H18), 6.60 (t, J$_{HH}$=4.9 Hz, 4H, H6), 7.38 (t, J$_{HH}$=1.3 Hz, 2H, H9), 7.45 (dd, J$_{HH}$=6.9, 3.3 Hz 8H, H1), 8.32 (dd, J$_{HH}$=6.9, 3.3 Hz 8H, H2), 8.73 (s, 4H, H10), 8.81 (s, 2H, H13). $^{13}$C NMR (125 MHz, CDCl$_3$): δ=28.22 C24, 29.99 C20, 30.03 C21, 31.92/31.98 C15/16, 37.49 C5, 57.88 C19, 58.56 C14, 80.78 C23, 124.90 C2/9, 126.44 C1, 129.85/130.27 C3/4, 130.35 C10, 165.55 C12, 166.21 C7, 172.87 C23, 173.22 C17. MS(ESI) calculated for C$_{202}$H$_{300}$O$_{48}$N$_{12}$Na$_2$$^{2+}$=1855.28; found 1855.14.

AnR-G2-Na.

AnR-G2-tBu (54.4 mg, 14.8 μmol) was dissolved in DCM (6 mL) and cooled to 0° C. over ice. TFA (2 mL) was added dropwise over 5 minutes and the solution stirred under N$_2$ for 16 hours at room temperature. The solvent was then removed under vacuum and the residue dissolved in H$_2$O/MeOH (6:4, 10 mL), and NaOH (0.1 M) was added dropwise until pH 7. The solution was then filtered through a syringe filter (0.45 m) and the remaining solution freeze-dried to obtain AnR-G2-Na as a pale yellow powder (43.7 mg, 97%). $^1$H NMR (500 MHz, CDCl$_3$): δ=1.97 (t, J$_{HH}$=7.4 Hz, 36H, H20), 2.20 (m, 48H, H15/21), 2.39 (t, J$_{HH}$=7.5 Hz, 12H, H21), 5.48 (s, 8H, H5), 7.56 (dd, J$_{HH}$=7.0, 2.6 Hz 8H, H1), 7.99 (s, 4H, H9), 8.29 (dd, J$_{HH}$=7.0, 2.6 Hz 8H, H2), 8.53 (s, 4H, H10). $^{13}$C NMR (125 MHz, D$_2$O)): δ=30.32 C20, 30.41 C15, 30.83 C16, 31.11 C21, 37.21 C5, 58.17 C19, 58.91 C14, 124.49 C2, 127.25 C1, 127.25 C9, 128.58 C4, 129.74 C3, 130.14 C10, 133.75 C8, 135.95 C11, 168.03/168.22 C12/7, 175.07 C17, 182.12 C22.

EXAMPLE 10—TESTING OF COMPOUND 13

Relevant properties of compound 13 were tested, in order to assess its suitability for use as a blood glucose sensor in vivo. The results are summarised in FIGS. 15A-15D.

Figure 15A:
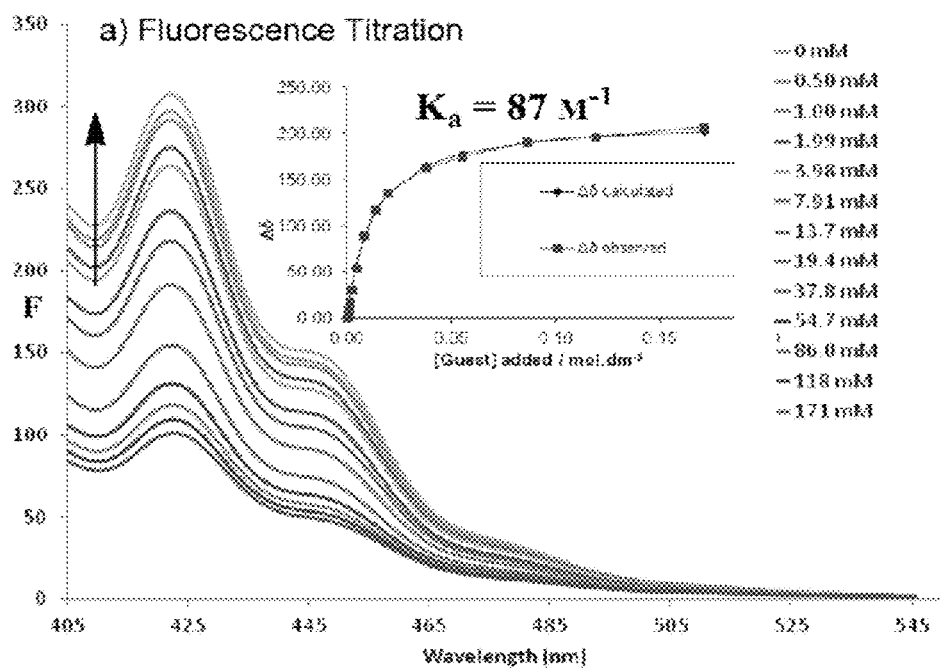

Firstly with regard to its optical properties, FIG. 15A shows fluorescence titration curves for the compound at 18.8 μM with glucose in phosphate buffer solution (pH 7.1, 0.1 M) at 298 K. The cell path length was 10 mm and the excitation wavelength 395 nm, and glucose concentrations from 0 to 171 mM were investigated. The inset shows binding data (423 nm) and fitting curve (Kaleidagraph), which gives K$_a$=87 M$^{-1}$. It can be seen from these data that compound 13 maintains its optical output from the anthracene core. Upon binding with D-glucose it exhibits an approximately three-fold increase in fluorescence emission (em 423 nm) when the system is excited (ex 395 nm).

Figure 15B:
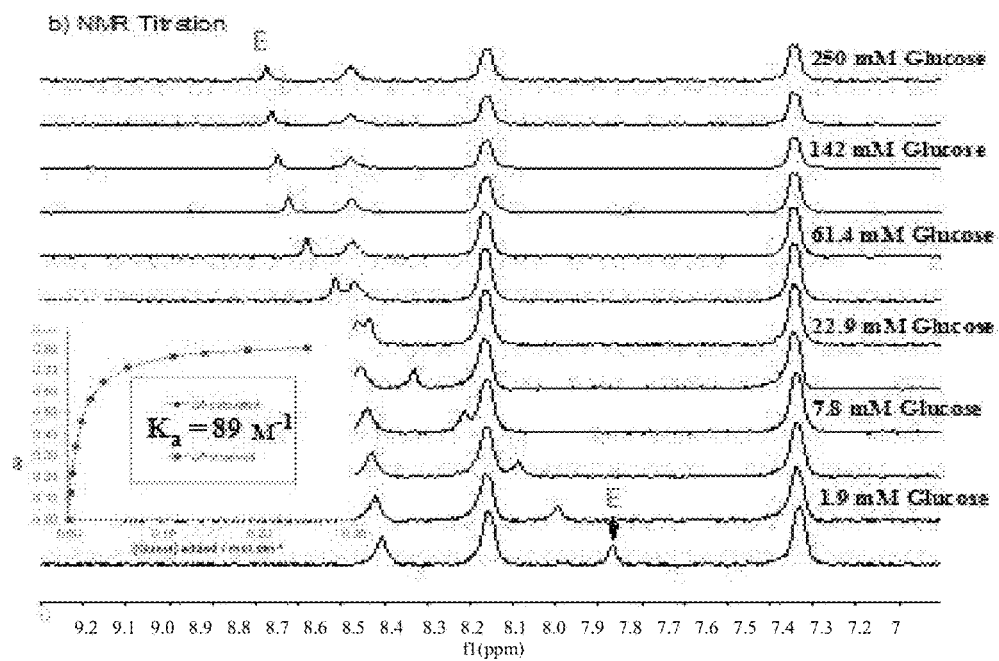

FIG. 15B shows partial $^1$H NMR spectra from the titration of compound 13 (0.125 mM) with D-glucose (α/β=36:64) in D$_2$O at 298 K. The inset illustrates both experimental and calculated values for the NMR binding of proton E of compound 13 (see the structure at the top right of FIG. 15C) with D-glucose in D$_2$O: these can be seen to be in good agreement, yielding a K$_a$ value of 89 M$^1$.

Figure 15D:
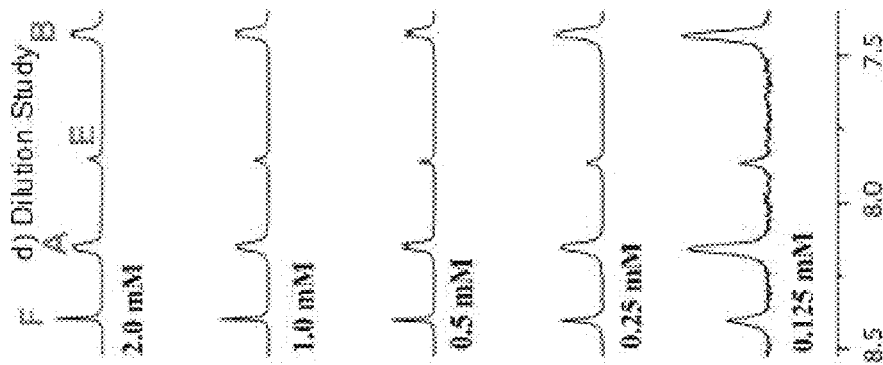
Figure 15C:
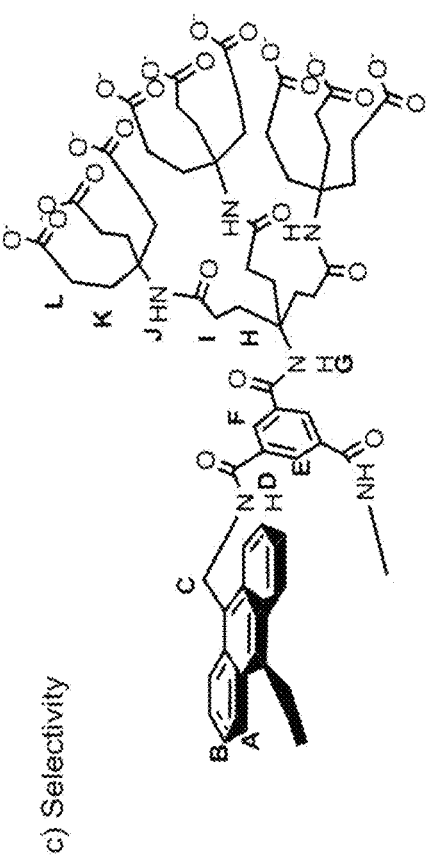

FIG. 15C is a table of NMR- and fluorescence-derived binding constants for compound 13 with three different saccharides. The data demonstrate the compound's selectivity towards all-equatorial saccharides such as D-glucose (K$_a$=89 and 87 M$^{-1}$), as compared to D-mannose and methyl-β-glucoside.

FIG. 15D shows partial $^1$H NMR spectra for compound 13 at concentrations from 0.125 mM to 2 mM in D$_2$O at 298 K, with assignments based on the structure at the top right of FIG. 15C. The compound exhibited good solubility in water, with no indication of aggregation during these NMR dilution studies.

Overall, these data indicate that compound 13 would be suitable for use as a glucose sensor in human blood serum. Its enhanced binding and selectivity for glucose over other sugars will make it sensitive to glucose levels even within the hypoglycemic range, and its fluorescence output can provide a detectable indication of saccharide binding in such contexts.

EXAMPLE 11—SYNTHESIS OF COMPOUND 14

The compound 14, shown in FIG. 12B, is a yet further compound according to the first aspect of the invention, designed for detecting glucose in blood. Its modified solubilising groups $R^9$ and $R^{10}$ give it even greater aqueous solubility than compound 13. These groups not only make compound 14 highly suitable for use in the bloodstream, but also allow for greater flexibility in the design of modified versions of compound 14 carrying alternative substituents on the anthracene units and/or additional functional groups.

A potential route to the synthesis of compound 14 is illustrated by the retrosynthetic scheme of FIGS. 13A-13C, and described in more detail below. This method also accords with the eleventh aspect of the invention, and in its latter stages is analogous to the method proposed for the preparation of compound 3. It begins with the preparation and attachment, to an isophthaloyl precursor of formula (III), of the solubilising moiety which will represent the substituents $R^9$ and $R^{10}$ in the final product.

In FIGS. 13A-13C and the following description, the compound 14 appears as its sodium salt "AnR-G3-Na"; the isophthaloyl precursor of formula (III) as "G3-Linker"; the amine used to link the hydrophilic moiety to the isophthaloyl precursor as "G3-NH$_2$"; and the corresponding nitro-substituted form of the amine as "G3-NO$_2$". FIGS. 14E to 14I show the structures for these compounds, and also for a t-butyl-protected form ("AnR-G3-tBu") of the eventual salt 14, in each case with the protons assigned.

Compound 14 was prepared using the route shown in FIGS. 13A-13C, as described below.

G3-NO$_2$.

G2-NH$_2$ (6.31 mg, 4.4 mmol, prepared as in Example 9), NO$_2$-triPFP (1.00 g, 1.30 mmol) and DIPEA (1 mL) were dissolved in THF (20 mL, anhydrous) under N$_2$. The reaction was heated to 50° C. and left stirring over molecular sieves (4 Å) for 48 hours. The solvent was removed and toluene added and evaporated three times to remove the DIPEA. The crude was purified via column chromatography (30:70 to 50:50 EA:HEX to 100:5 EA: MeOH) to yield G3-NO$_2$ as a white solid (3.04 g, 52%). $R_f$=0.65 (50:50 EA:HEX). $^1$H NMR (500 MHz, CDCl$_3$): δ=1.42 (, 243H, H1), 1.94 (m, 78H, H5/10/15), 2.16 (m, 78H, H4/9/14), 6.28 (s, 9H, H7), 7.00 (s, 3H, H12). MS(HiRes-ESI) calculated for $C_{238}H_{411}O_{68}N_{13}Na_3^{3+}$=1536.2938; found 1536.2926.

G3-NH$_2$.

To an autoclave (250 mL) G3-NO$_2$ (2.93 g, 0.64 mmol), Raney Ni (10 mL, water slurry) and ethanol (40 mL) were added. The autoclave was then sealed, pressured with H$_2$ (50 bar) and left stirring for 24 hours at 60° C. The mixture was then filtered through celite, washed with DCM (50 mL) and the solvent removed under reduced pressure to yield G2-NH$_2$ (2.90 g, 99%). $R_f$=0.5 (EA). $^1$H NMR (500 MHz, CDCl$_3$): δ=1.40 (, 243H, H1), 1.92 (m, 78H, H5/10/15), 2.17 (m, 78H, H4/9/14), 6.41 (s, 9H, H7), 7.66 (s, 3H, H12). MS(HiRes-ESI) calculated for $C_{238}H_{414}O_{66}N_{13}Na_3^{3+}$=1518.9739; found 1518.9682.

G3-Linker.

G3-NH$_2$ (0.50 g, 111 μmol) and tri-PFP (0.54 g, 333 μmol) were dissolved in THF (1 mL, anhydrous) under N$_2$ over molecular sieves (4 Å). DIPEA (1 mL, 10.4 mmol) was injected and the reaction heated to 40° C. and left stirring for 4 hours at room temperature under N$_2$. The solvent was removed under vacuum and toluene (60 mL) added and removed three times on the rotary evaporator to remove the DIPEA. The crude was purified via column chromatography (40:60 to 60:40 to 100:0 EA:HEX) to yield G3-Linker as a white foam (280 mg, 50%). $R_f$=0.5 (50:50, EA:HEX). $^{19}$F NMR (470 MHz, CDCl$_3$): δ=−151.92 (d, $J_{FF}$=19.1 Hz, 4F, F25), −157.32 (t, $J_{FF}$=22.0 Hz, 2F, F27), −161.89 (t, $J_{FF}$=20.2 Hz, 4F, F26). $^1$H NMR (500 MHz, CDCl$_3$): δ=1.41 (s, 243H, H1), 1.92 (m, 78H, H5/10/15), 2.16 (m, 78H, H4/9/14), 6.27 (s, 9H, H7), 6.88 (s, 3H, H12), 9.06 (s, 1H, H22), 9.14 (s, 2H, H20), 9.49 (s, 1H, H17). MS(HiRes-ESI) calculated for $C_{259}H_{415}O_{71}N_{13}F_{10}Na_3^{3+}$=1700.9593; found 1700.9530.

AnR-G3-tBu.

9,10-Bis-amino(methyl)anthracene (13.1 mg, 55.6 μmol) was dissolved in THF (250 mL, anhydrous) and DIPEA (2 mL, 21.9 mmol). Next a solution of G3-Linker (280 mg, 55.6 μmol) in THF (50 mL, anhydrous) was injected into the solution of amine over 36 hours with an automated syringe pump under N$_2$ with stirring. After the addition the reaction was left for a further 36 hours. The solvent was removed under vacuum and the crude dissolved in DCM (50 mL) and washed with NH$_4$Cl (sat aq, 50 mL), water (50 mL) and brine (50 mL), then dried over MgSO$_4$, filtered and evaporated in vacuo. The crude was dissolved in acetone/water (85:15, 4 mL) and filtered through a syringe filter (0.45 m). The solution was injected into a preparative reverse phase HPLC apparatus fitted with a reverse phase column (Waters—Xselect, 250×19 mm, 5 m) and eluted with acetone/water (85:15 to 100:0 over 30 min; flow rate 19 mL/min). The component eluting at 22 min was collected, concentrated under vacuum and freeze-dried to yield AnR-G3-tBu (130 mg, 48%) as a white powder. $^1$H NMR (500 MHz, CDCl$_3$): δ=1.42 (s, 243H, H30), 1.96 (t, $J_{HH}$=8.2 Hz, 108H, H25), 2.05 (s, 54H, H20/15), 2.20 (t, $J_{HH}$=8.2 Hz, 162H, H26/21/16), 5.58 (s, 8H, H5), 6.40 (s, 6H, H18), 6.51 (s, 18H, H23), 6.94 (s, 4H, H6), 7.44 (m, 10H, H1/8), 8.41 (m, 8H, H2), 8.67 (s, 4H, H10), 8.81 (s, 2H, H13). MS(ESI) calculated for $C_{526}H_{858}N_{30}O_{138}Na_3^{3+}$=3291.02; found 3292.90.

AnR-G3-Na.

AnR-G3-tBu (80 mg, 8.2 μmol) was dissolved in DCM (6 mL) and cooled to 0° C. over ice. Next TFA (2 mL) was added dropwise over 5 minutes and the reaction left for 16 hours at room temperature under N$_2$. The TFA was then removed under vacuum and the product dissolved in H$_2$O: MeOH (6:4, 10 mL). Next NaOH (0.1 M) was added until pH 7 and the solution freeze-dried to yield the product (65 mg, 98%). $^1$H NMR (500 MHz, CDCl$_3$): δ=1.42 (s, 243H, H30), 1.96 (t, $J_{HH}$=8.2 Hz, 108H, H25), 2.05 (s, 54H, H20/15), 2.20 (t, $J_{HH}$=8.2 Hz, 162H, H26/21/16), 5.58 (s, 8H, H5), 6.40 (s, 6H, H18), 6.51 (s, 18H, H23), 6.94 (s, 4H, H6), 7.44 (m, 10H, H1/8), 8.41 (m, 8H, H2), 8.67 (s, 4H, H10), 8.81 (s, 2H, H13).

Compound 14 is expected to bind selectively to glucose in a similar manner to compounds 3 and 13, demonstrating selectivity over other saccharides and indeed over other species which are likely to be present in the bloodstream. It is also expected to generate a similar spectroscopic response, dependent upon glucose binding. It will be highly soluble in an aqueous environment such as human blood serum.

EXAMPLE 12—IMMOBILISATION OF COMPOUND 3

The compound 3 was immobilised within a hydrogel support by the following method. The polymer used was a poly[acryloyl-bis(aminopropyl)polyethylene glycol] (PEGA), purchased from Sigma Aldrich in the form of beads with an average diameter of 300-500 m. The PEGA beads were stored in 90% MeOH with an amine functionality of 0.2 mmol/g.

Firstly, the sodium salt of compound 3 ("AnR-G1-Na", obtained as in Example 1) was converted to the free acid form "AnR-G1-H". AnR-G1-Na (12.1 mg, 7.59 μmol) was dissolved in water (0.8 mL) and HCl (1 M) was added dropwise until pH 2. The precipitate was collected, washed with water (3×2 mL) and freeze-dried to yield AnR-G1-H as a yellow powder (10.9 mg, 99%).

Next, PEGA beads (2.9 mg, 0.58 μmol ($NH_2$)) were weighed into an eppendorf tube (1 mL) and centrifuged at 6000 rpm for 2 minutes. DMSO (250 μL, anhydrous) was added and the mixture was centrifuged at 6000 rpm for 5 minutes and decanted three times. AnR-G1-H (2.96 mg, 2.03 μmol) was dissolved in DMSO (400 μL) and added to the beads under $N_2$. NHS (N-hydroxysuccinimide) (1.40 mg, 12.2 μmol) and EDCI (1-ethyl-3-(3-dimethylaminopropyl) carbodiimide) (2.33 mg, 12.18 μmol) were dissolved in DMSO (200 μL) and added, followed by DIPEA (3.03 μL, 17.4 μmol). The reaction was gently rocked for 16 hours, after which the tube was centrifuged at 6000 rpm for 2 minutes and the DMSO removed. DCM (0.5 mL) and water (0.5 mL) were added and shaken and the DCM layer removed three times. The beads were then washed with DMSO (2×1.5 mL) and MeOH (2×1.5 mL). NaOH (1.5 mL, 1 M) was added to the beads and they were shaken for 2 hours. The beads were then washed with water (3×1.5 mL) and PBS (phosphate buffered saline) (0.1 M, pH 7.4, 2×1.5 mL). This method was analogous to that disclosed by Shapiro et al in "Measuring Binding of Protein to Gel-Bound Ligands Using Magnetic Levitation", *J Am Chem Soc* (2012), 134(12): 5637-5646.

Thus immobilised, the compound 3 is in a form suitable for introduction into a patient's body, to allow the in vivo monitoring of blood glucose levels. The hydrogel may for example form part of an implant for introduction into the bloodstream, or may be provided on a fibre optic probe.

EXAMPLE 13—SHIFTING OF FLUORESCENCE

By altering the substituents on the anthracene moieties of compounds such as 3, 13 and 14, it is possible to alter their spectroscopic responses. This example demonstrates the tailoring of fluorescence emissions spectra in anthracene-containing precursor compounds which are usable to prepare compounds of formula (II) and in turn compounds of formula (I).

Four such precursor compounds were prepared and tested, in which the anthracene substituents $R^1$ to $R^4$ were all either (a) hydrogen, (b) —$OCH_3$, (c) —$CO_2CH_3$ or (d) N-substituted cyclic imido, with the nitrogen atom being substituted with —$CH_2CO_2$-t-butyl. In these compounds, the —$CH_2NH_2$ groups of formula (II) were instead methyl groups.

FIGS. 17A and 17B shows schematically the methods by which the substituted precursor compounds were prepared. The tested products are labelled CMR 1 ($R^1$-$R^4$=—$OCH_3$); CMR 4 ($R^1$-$R^4$=—$CO_2CH_3$); and CMR 6 ($R^1$-$R^4$=N-substituted cyclic imido).

In FIGS. 17A and 17B, BINAP is 2,2'-bis(diphenylphosphino)-1,1'-binaphthyl and HMDS is hexamethyldisilazane, also known as bis(trimethylsilyl)amine. The compound CMR 1 was prepared as described in the literature (Modjewski et al, *Tetrahedron Lett* (2009) 50: 6687-6690). The unsubstituted analogue bis-methylanthracene is commercially available.

The emissions spectra of the precursor compounds were recorded using a PerkinElmer® LS45 fluorescence spectrometer, at wavelengths between 400 and 550 nm. The results are shown in FIG. 18. It can be seen that the addition of ester groups to the anthracene unit shifts its emissions peak towards the red (longer wavelength) end of the spectrum. Substitution with the cyclic imido groups shifts the peak yet further. The methoxyl substituents, in contrast, shift the emissions peak in the opposite direction, to a shorter wavelength. Similar trends can be expected in the emissions spectra of compounds of formula (I) derived from these precursors. Thus, the compounds can be tailored to provide a spectroscopic response in a desired region of the spectrum. An emissions peak at a longer wavelength—for example about 550 nm or greater—is expected to be of particular value for in vivo glucose detection systems.

CONCLUSIONS

It can be seen from the above that compounds 3, 13 and 14, and other analogous compounds according to the invention, are likely to provide an excellent starting point for a new approach to blood glucose monitoring. Their simplicity, accessibility and tunability can make them suitable for use in continuous glucose monitoring systems, in a practical and cost-effective manner.

In particular, an analogue of compound 3, or of compound 13 or 14, in which the substituents on the two anthracene units are chosen so as to increase the peak emissions wavelength of the compound (for example, by extending conjugation), could be of particular value for the in vivo monitoring of blood glucose levels. In the compounds 13 and 14 especially, which carry highly hydrophilic solubilising groups $R^9$ and $R^{10}$, it should be possible to modify the anthracene units in order to tune their spectroscopic responses, without undue detriment to the aqueous solubility of the overall compounds.

Explanation of FIG. 11

FIG. 11 shows schematically a detection and supply system according to the seventh aspect of the invention. This incorporates a device according to the fifth aspect and a detection system according to the sixth aspect, and may be used in a method according to the eighth, ninth or tenth aspect of the invention. In this case the system is for use in detecting the concentration of glucose in the bloodstream of a living patient, and for supplying insulin to the bloodstream when necessary: it can thus be used as or in an artificial pancreas.

The system comprises a detection device 50, which is introduced into the patient's bloodstream (denoted generally as 51). The device 50 may for example take the form of an implantable chip or capsule, or a probe such as a fibre optic probe. Carried in or on the device 50, in an appropriate physical form such as a hydrogel, is a compound according to the first or second aspect of the invention, or a polymer according to the third aspect. This compound or polymer exhibits a spectroscopic response in the presence of glucose, the nature and/or magnitude of the response being dependent on the glucose concentration in the bloodstream 51.

The system also comprises a detector 52, in the form of a small device which can be strapped to the patient's body at or close to the location of the implanted device 50. The detector 52 is capable of detecting the spectroscopic response of the compound or polymer to its environment. The detector 52 comprises interrogation means 53, by which it can apply electromagnetic radiation 54 at a wavelength suitable to excite the compound or polymer and to cause it to emit electromagnetic radiation 55 in response. The emitted wave 55 can be detected by the detector 52, which then sends a signal 56 to the control means 57. The signal 56 thus carries information regarding the concentration of glucose in the patient's bloodstream. Such information may be relayed from the detector 52 and/or the control means 57 to an output device 58, such as a screen, from which a user may obtain information about glucose concentrations and/or associated warnings. Information may also be output from the detector and/or the control means to another device or system such as is shown at 59.

The control means 57 incorporates a comparator means 60. This compares the signal 56 with pre-programmed information regarding safe blood glucose concentrations. If the control means detects a predetermined minimum difference between the signal 56 and the programmed safe concentrations, it sends a signal 61 to the delivery means 62, which is connected to a supply 64 of insulin. The signal 61 controls the delivery of insulin from the supply 64 back into the patient's bloodstream, via a pump 63 and appropriate intravenous conduits 65. In this way, the control means 57 can maintain the patient's blood glucose levels within safe ranges, supplying insulin when necessary in response to detected changes. Monitoring of the patient's blood glucose levels, and their maintenance within safe ranges, can be done continuously due to the presence of the device 50 in the bloodstream and the simplicity, and ready detectability, of the response of the detector compound (I) or (Ia) to changing glucose concentrations.

The control means 57 may comprise one or more of: a microprocessor or other data processing and/or operational control means; a data storage means such as a flash memory; and a connector or connection port for connecting to another device or system 59 (for example a computer) in order to transfer data between the two. Instead or in addition, conventional wireless communication and data transfer systems may be used to control operation of, and communicate with, the detection system remotely.

The invention claimed is:

1. A water-soluble compound of the formula (I):

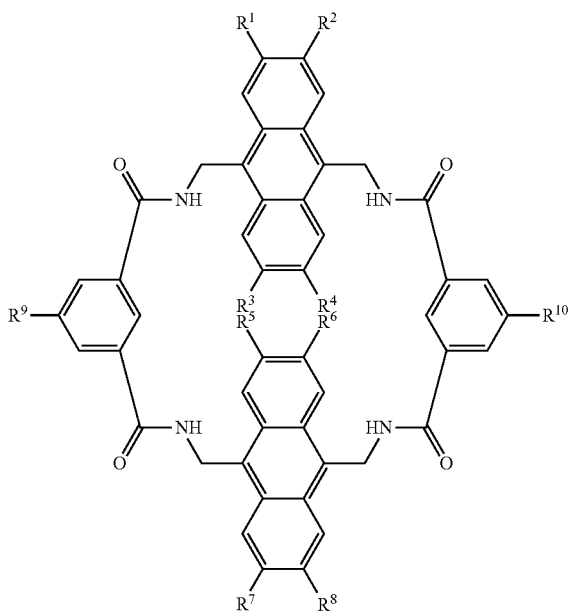

(I)

wherein $R^1$ to $R^8$ are each independently selected from hydrogen; optionally substituted alkyl groups; optionally substituted cycloalkyl groups; optionally substituted heterocyclyl groups; optionally substituted alkenyl groups; optionally substituted alkynyl groups; optionally substituted aryl groups; optionally substituted heteroaryl groups; alkoxyl groups; ketone and aldehyde groups; carboxylic acids and carboxylate ions; carboxylate esters; —$SO_3H$; —$SO_3^-$; —$OSO_3H$; —$OSO_3^-$; —$PO_3XY$ where X and Y are independently hydrogen, alkyl or a negative charge; —$OPO_3XY$ where X and Y are independently hydrogen, alkyl or a negative charge; amines; amides; halo groups; —CN; —$NO_2$; —OH; and imino and imido groups, provided that in any one or more of the pairs $R^1R^2$, $R^3R^4$, $R^5R^6$ and $R^7R^8$, the two substituents may be joined together to form part of an optionally substituted cyclic group; and $R^9$ and $R^{10}$ are each independently selected from hydrogen or hydrophilic substituents comprising two or more hydrophilic functional groups selected from carboxylic acids, carboxylate ions, carboxylate esters, hydroxyl, amines, amides, ethers, ketone and aldehyde groups, —$NO2$, sulphates, sulphonates, phosphates, phosphonates, and combinations thereof; and wherein at least one of $R^9$ or $R^{10}$ is a hydrophilic substituent.

2. A compound according to claim 1, wherein said two or more hydrophilic functional groups are selected from carboxylic acids, carboxylate ions, amides, ethers and combinations thereof.

3. A compound according to claim 1 or 2, wherein $R^1$ to $R^8$ are selected from hydrogen, carboxylate esters, alkoxyl groups, optionally substituted cyclic imido groups, hydroxyl and sulphonates.

4. A compound according to claim 1, wherein $R^1$ to $R^8$ are all hydrogen.

5. A compound according to claim 1, wherein the at least one hydrophilic substituent is selected from groups of the formula —C(O)—$R^{14}$, where $R^{14}$ is selected from:

a. groups —$NR^{15}C(R^{16}CO_2H)_3$ in which $R^{15}$ is selected from hydrogen and C1 to C4 alkyl; and $R^{16}$ is a group $(CH_2)_n$, where n is an integer from 1 to 6, optionally containing an ether group —O—;

b. groups —$NR^{15}C(R^{17})_3$ in which $R^{15}$ is as defined above; $R^{17}$ is a group —$R^{18}C(O)NR^{15}$—$C(R^{18}CO_2H)_3$; and each $R^{18}$ is independently selected from groups $R^{16}$ as defined above; and c. groups —$NR^{15}C(R^{25})_3$ in which $R^{15}$ is as defined above; $R^{25}$ is a group —$R^{18}C(O)NR^{15}$—$C(R^{26})_3$; $R^{26}$ is a group —$R^{18}C(O)NR^{15}$—$C(R^{18}CO_2H)_3$; and each $R^{18}$ is independently selected from groups $R^{16}$ as defined above.

6. A compound according to claim 1, which has one of the formulae shown below:

49
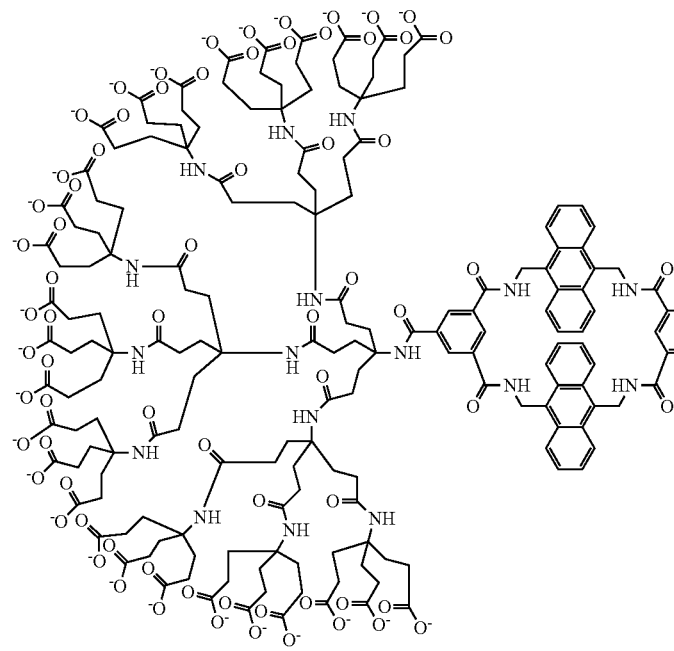
50
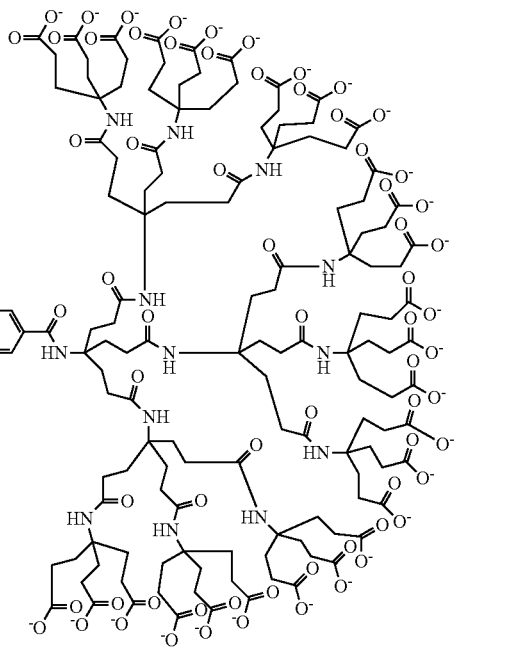
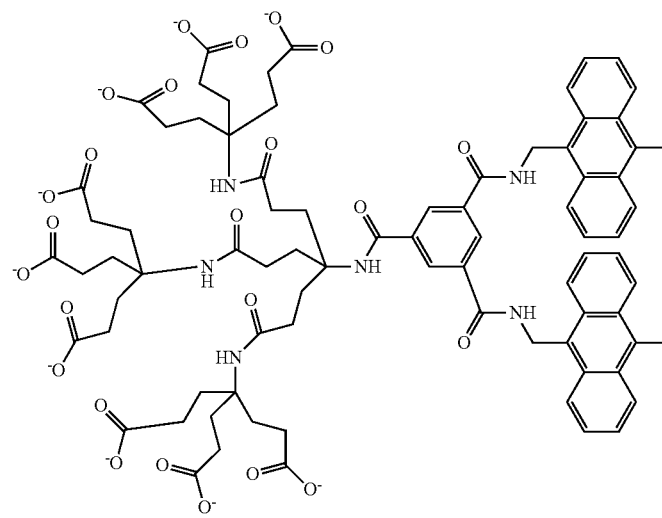
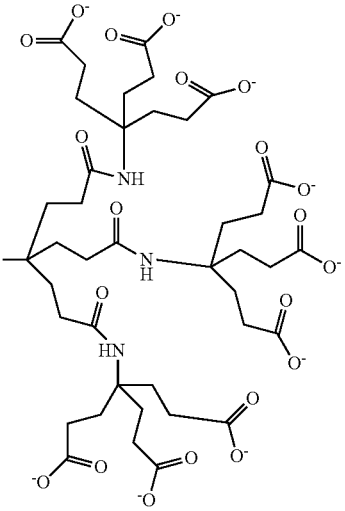
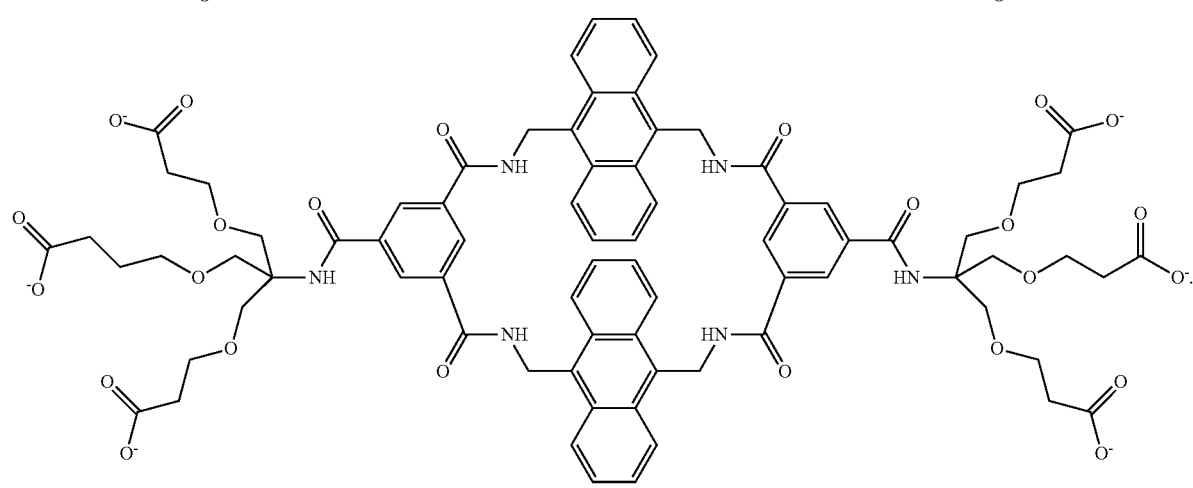

7. A compound according to claim 1, which has the formula:

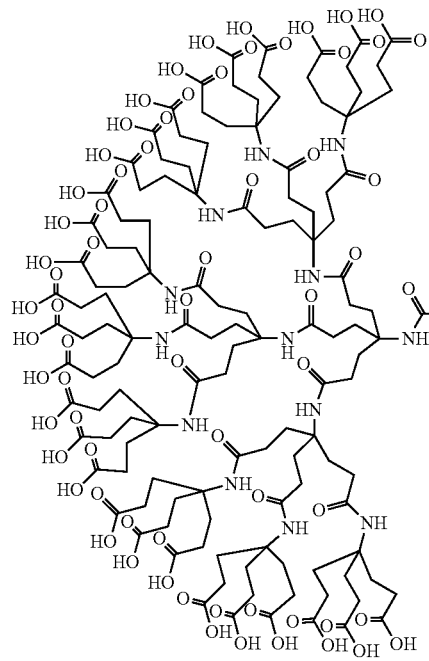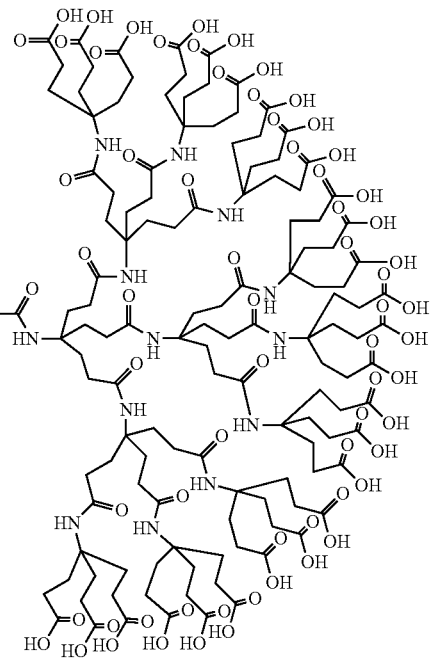

or a salt or protected form thereof.

8. A compound according to claim 1, which exhibits a spectroscopic response on complexing with a target saccharide, in particular glucose, which spectroscopic response is preferably detectable in the visible and/or near-infrared region of the electromagnetic spectrum.

9. A compound according to claim 1, which is immobilised on or in a solid or semi-solid support.

10. A compound according to claim 9, wherein the solid or semi-solid support is a polymeric matrix and/or a gel, such as a hydrogel.

11. A compound according to claim 10, wherein the polymeric matrix and/or gel is a polymer selected from cross-linked polyethylene glycol and/or polyacrylamide.

12. A compound according to claim 10 or 11, wherein the compounds are chemically linked to the polymeric matrix and/or gel.

13. A compound according to claim 10 or 11, wherein the compounds are physically incorporated within the polymeric matrix and/or gel via non-covalent interactions.

* * * * *